(12) United States Patent
Danek et al.

(10) Patent No.: US 9,033,976 B2
(45) Date of Patent: *May 19, 2015

(54) MODIFICATION OF AIRWAYS BY APPLICATION OF ENERGY

(71) Applicant: Asthmatx, Inc., Sunnyvale, CA (US)

(72) Inventors: Christopher J. Danek, San Carlos, CA (US); Michael Biggs, San Francisco, CA (US); Keith M. Burger, San Francisco, CA (US); Bryan Loomas, Los Gatos, CA (US); Thomas Keast, Mountain View, CA (US); Dave Haugaard, San Jose, CA (US)

(73) Assignee: Asthmatx, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/895,735

(22) Filed: May 16, 2013

(65) Prior Publication Data

US 2013/0253623 A1 Sep. 26, 2013

Related U.S. Application Data

(63) Continuation of application No. 13/557,485, filed on Jul. 25, 2012, now Pat. No. 8,465,486, which is a continuation of application No. 11/534,621, filed on Sep. 22, 2006, now Pat. No. 8,257,413, which is a (Continued)

(51) Int. Cl.
*A61B 18/14* (2006.01)
*A61N 5/00* (2006.01)

(Continued)

(52) U.S. Cl.
CPC . *A61N 5/00* (2013.01); *A61B 18/08* (2013.01); *A61B 18/1477* (2013.01); *A61B 18/1492* (2013.01); *A61B 2017/00084* (2013.01);

(Continued)

(58) Field of Classification Search
USPC ........ 606/41, 48–50; 607/101, 102, 115, 116, 607/122
See application file for complete search history.

(56) References Cited

U.S. PATENT DOCUMENTS

| 612,724 A | 10/1898 | Hamilton |
| 1,155,169 A | 9/1915 | Starkweather |

(Continued)

FOREIGN PATENT DOCUMENTS

| DE | 19529634 A1 | 2/1997 |
| EP | 189329 A3 | 6/1987 |

(Continued)

OTHER PUBLICATIONS

An S.S., et al., "Airway Smooth Muscle Dynamics: A Common Pathway of Airway Obstruction in Asthma," European Respiratory Journal, 2007, 29 (5), 834-860.

(Continued)

*Primary Examiner* — Michael Peffley
(74) *Attorney, Agent, or Firm* — Bookoff McAndrews, PLLC

(57) ABSTRACT

This relates to treating reversible chronic obstructive pulmonary disease, and more particularly, to exchanging energy with airway tissue such as that found in human lungs. This exchange of energy reduces the ability of the airways to constrict, reduces the resistance within the airway to the flow of air through the airway, reduces mucus plugging of the airways, and/or increases the airway diameter. This energy exchange also may reduce the ability of the lung to produce at least one of the symptoms of reversible obstructive pulmonary disease.

18 Claims, 24 Drawing Sheets

Related U.S. Application Data continuation of application No. 10/414,253, filed on Apr. 14, 2003, now Pat. No. 7,198,635, which is a continuation of application No. PCT/US00/28745, filed on Oct. 17, 2000.

(51) Int. Cl.
  *A61N 1/06* (2006.01)
  *A61B 18/08* (2006.01)
  *A61B 17/00* (2006.01)
  *A61B 18/00* (2006.01)
  *A61B 18/04* (2006.01)
  *A61B 19/00* (2006.01)

(52) U.S. Cl.
  CPC .......... *A61B2017/00123* (2013.01); *A61B 2018/00214* (2013.01); *A61B 2018/0022* (2013.01); *A61B 2018/00267* (2013.01); *A61B 2018/00541* (2013.01); *A61B 2018/00982* (2013.01); *A61B 2018/046* (2013.01); *A61B 2019/5217* (2013.01); *A61N 1/06* (2013.01)

(56) References Cited

U.S. PATENT DOCUMENTS

| | | |
|---|---|---|
| 1,207,479 A | 12/1916 | Bisgaard |
| 1,216,183 A | 2/1917 | Swingle |
| 2,072,346 A | 3/1937 | Smith |
| 3,320,957 A | 5/1967 | Sokolik |
| 3,568,659 A | 3/1971 | Karnegis |
| 3,667,476 A | 6/1972 | Muller |
| 3,692,029 A | 9/1972 | Adair |
| 3,995,617 A | 12/1976 | Watkins et al. |
| 4,095,602 A | 6/1978 | LeVeen |
| 4,116,589 A | 9/1978 | Rishton |
| 4,129,129 A | 12/1978 | Amrine |
| 4,154,246 A | 5/1979 | LeVeen |
| 4,461,283 A | 7/1984 | Doi |
| 4,502,490 A | 3/1985 | Evans et al. |
| 4,503,855 A | 3/1985 | Maslanka |
| 4,512,762 A | 4/1985 | Spears |
| 4,522,212 A | 6/1985 | Gelinas et al. |
| 4,557,272 A | 12/1985 | Carr |
| 4,565,200 A | 1/1986 | Cosman |
| 4,567,882 A | 2/1986 | Heller |
| 4,584,998 A | 4/1986 | McGrail |
| 4,612,934 A | 9/1986 | Borkan |
| 4,621,642 A | 11/1986 | Chen |
| 4,621,882 A | 11/1986 | Krumme |
| 4,625,712 A | 12/1986 | Wampler |
| 4,643,186 A | 2/1987 | Rosen et al. |
| 4,646,737 A | 3/1987 | Hussein et al. |
| 4,674,497 A | 6/1987 | Ogasawara |
| 4,683,890 A | 8/1987 | Hewson |
| 4,704,121 A | 11/1987 | Moise |
| 4,706,688 A | 11/1987 | Don Michael et al. |
| 4,709,698 A | 12/1987 | Johnston et al. |
| 4,739,759 A | 4/1988 | Rexroth et al. |
| 4,754,065 A | 6/1988 | Levenson et al. |
| 4,754,752 A | 7/1988 | Ginsburg et al. |
| 4,765,959 A | 8/1988 | Fukasawa |
| 4,772,112 A | 9/1988 | Zider et al. |
| 4,773,899 A | 9/1988 | Spears |
| 4,779,614 A | 10/1988 | Moise |
| 4,784,135 A | 11/1988 | Blum et al. |
| 4,790,305 A | 12/1988 | Zoltan et al. |
| 4,799,479 A | 1/1989 | Spears |
| 4,802,492 A | 2/1989 | Grunstein |
| 4,817,586 A | 4/1989 | Wampler |
| 4,825,871 A | 5/1989 | Cansell |
| 4,827,935 A | 5/1989 | Geddes et al. |
| 4,846,152 A | 7/1989 | Wampler et al. |
| 4,862,886 A | 9/1989 | Clarke et al. |
| 4,895,557 A | 1/1990 | Moise et al. |
| 4,906,229 A | 3/1990 | Wampler |
| 4,907,589 A | 3/1990 | Cosman |
| 4,908,012 A | 3/1990 | Moise et al. |
| 4,920,978 A | 5/1990 | Colvin |
| 4,944,722 A | 7/1990 | Carriker et al. |
| 4,955,377 A | 9/1990 | Lennox et al. |
| 4,967,765 A | 11/1990 | Turner et al. |
| 4,969,865 A | 11/1990 | Hwang et al. |
| 4,976,709 A | 12/1990 | Sand |
| 4,985,014 A | 1/1991 | Orejola |
| 4,991,603 A | 2/1991 | Cohen et al. |
| 5,009,636 A | 4/1991 | Wortley et al. |
| 5,009,936 A | 4/1991 | Yamanaka et al. |
| 5,010,892 A | 4/1991 | Colvin et al. |
| 5,019,075 A | 5/1991 | Spears et al. |
| 5,027,829 A | 7/1991 | Larsen |
| 5,030,645 A | 7/1991 | Kollonitsch |
| 5,036,848 A | 8/1991 | Hewson |
| 5,053,033 A | 10/1991 | Clarke |
| 5,056,519 A | 10/1991 | Vince |
| 5,074,860 A | 12/1991 | Gregory et al. |
| 5,078,716 A | 1/1992 | Doll |
| 5,084,044 A | 1/1992 | Quint |
| 5,096,916 A | 3/1992 | Skupin |
| 5,100,388 A | 3/1992 | Behl et al. |
| 5,100,423 A | 3/1992 | Fearnot |
| 5,103,804 A | 4/1992 | Abele et al. |
| 5,105,826 A | 4/1992 | Smits et al. |
| 5,106,360 A | 4/1992 | Ishiwara et al. |
| 5,107,830 A | 4/1992 | Younes |
| 5,114,423 A | 5/1992 | Kasprzyk et al. |
| 5,116,864 A | 5/1992 | March et al. |
| 5,117,828 A | 6/1992 | Metzger et al. |
| 5,135,517 A | 8/1992 | McCoy |
| 5,152,286 A | 10/1992 | Sitko et al. |
| 5,165,420 A | 11/1992 | Strickland |
| 5,167,223 A | 12/1992 | Koros et al. |
| 5,170,803 A | 12/1992 | Hewson et al. |
| 5,174,288 A | 12/1992 | Bardy et al. |
| 5,188,602 A | 2/1993 | Nichols |
| 5,191,883 A | 3/1993 | Lennox et al. |
| 5,213,576 A | 5/1993 | Abiuso et al. |
| 5,215,103 A | 6/1993 | Desai |
| 5,231,996 A | 8/1993 | Bardy et al. |
| 5,232,444 A | 8/1993 | Just et al. |
| 5,234,456 A | 8/1993 | Silvestrini |
| 5,254,088 A | 10/1993 | Lundquist et al. |
| 5,255,678 A | 10/1993 | Deslauriers et al. |
| 5,255,679 A | 10/1993 | Imran |
| 5,265,604 A | 11/1993 | Vince |
| 5,269,758 A | 12/1993 | Taheri |
| 5,281,218 A | 1/1994 | Imran |
| 5,292,331 A | 3/1994 | Boneau |
| 5,293,869 A | 3/1994 | Edwards et al. |
| 5,309,910 A | 5/1994 | Edwards et al. |
| 5,311,866 A | 5/1994 | Kagan et al. |
| 5,313,943 A | 5/1994 | Houser et al. |
| 5,324,284 A | 6/1994 | Imran |
| 5,343,936 A | 9/1994 | Beatenbough et al. |
| 5,345,936 A | 9/1994 | Pomeranz et al. |
| 5,366,443 A | 11/1994 | Eggers et al. |
| 5,368,591 A | 11/1994 | Lennox et al. |
| 5,370,644 A | 12/1994 | Langberg |
| 5,370,679 A | 12/1994 | Atlee, III |
| 5,374,287 A | 12/1994 | Rubin |
| 5,383,917 A | 1/1995 | Desai et al. |
| 5,393,207 A | 2/1995 | Maher et al. |
| 5,394,880 A | 3/1995 | Atlee, III |
| 5,396,887 A | 3/1995 | Imran |
| 5,400,778 A | 3/1995 | Jonson et al. |
| 5,400,783 A | 3/1995 | Pomeranz et al. |
| 5,411,025 A | 5/1995 | Webster, Jr. |
| 5,415,166 A | 5/1995 | Imran |
| 5,415,656 A | 5/1995 | Tihon et al. |
| 5,417,687 A | 5/1995 | Nardella et al. |
| 5,422,362 A | 6/1995 | Vincent et al. |
| 5,423,744 A | 6/1995 | Gencheff et al. |
| 5,423,811 A | 6/1995 | Imran et al. |
| 5,425,023 A | 6/1995 | Haraguchi et al. |

(56) References Cited

U.S. PATENT DOCUMENTS

| | | |
|---|---|---|
| 5,425,703 A | 6/1995 | Feiring |
| 5,425,811 A | 6/1995 | Mashita |
| 5,431,696 A | 7/1995 | Atlee, III |
| 5,433,730 A | 7/1995 | Alt |
| 5,437,665 A | 8/1995 | Munro |
| 5,443,470 A | 8/1995 | Stern et al. |
| 5,454,782 A | 10/1995 | Perkins |
| 5,456,667 A | 10/1995 | Ham et al. |
| 5,458,596 A | 10/1995 | Lax et al. |
| 5,465,717 A | 11/1995 | Imran et al. |
| 5,471,982 A | 12/1995 | Edwards et al. |
| 5,474,530 A | 12/1995 | Passafaro et al. |
| 5,478,309 A | 12/1995 | Sweezer et al. |
| 5,496,271 A | 3/1996 | Burton et al. |
| 5,496,311 A | 3/1996 | Abele et al. |
| 5,496,312 A | 3/1996 | Klicek |
| 5,500,011 A | 3/1996 | Desai |
| 5,505,728 A | 4/1996 | Ellman et al. |
| 5,505,730 A | 4/1996 | Edwards |
| 5,507,791 A | 4/1996 | Sit'ko |
| 5,509,419 A | 4/1996 | Edwards et al. |
| 5,522,862 A | 6/1996 | Testerman et al. |
| 5,531,779 A | 7/1996 | Dahl et al. |
| 5,540,681 A | 7/1996 | Strul et al. |
| 5,545,161 A | 8/1996 | Imran |
| 5,545,193 A | 8/1996 | Fleischman et al. |
| 5,547,469 A | 8/1996 | Rowland et al. |
| 5,549,559 A | 8/1996 | Eshel |
| 5,549,655 A | 8/1996 | Erickson |
| 5,549,661 A | 8/1996 | Kordis et al. |
| RE35,330 E | 9/1996 | Malone et al. |
| 5,558,073 A | 9/1996 | Pomeranz et al. |
| 5,562,608 A | 10/1996 | Sekins et al. |
| 5,571,074 A | 11/1996 | Buckman, Jr. et al. |
| 5,571,088 A | 11/1996 | Lennox et al. |
| 5,574,059 A | 11/1996 | Regunathan et al. |
| 5,575,810 A * | 11/1996 | Swanson et al. ............ 607/99 |
| 5,578,072 A | 11/1996 | Barone et al. |
| 5,582,609 A | 12/1996 | Swanson et al. |
| 5,588,432 A | 12/1996 | Crowley |
| 5,588,812 A | 12/1996 | Taylor et al. |
| 5,595,183 A | 1/1997 | Swanson et al. |
| 5,598,848 A | 2/1997 | Swanson et al. |
| 5,599,345 A | 2/1997 | Edwards et al. |
| 5,601,088 A | 2/1997 | Swanson et al. |
| 5,605,157 A | 2/1997 | Panescu et al. |
| 5,607,419 A | 3/1997 | Amplatz et al. |
| 5,607,462 A | 3/1997 | Imran |
| 5,620,438 A | 4/1997 | Amplatz et al. |
| 5,623,940 A | 4/1997 | Daikuzono |
| 5,624,439 A | 4/1997 | Edwards et al. |
| 5,626,618 A | 5/1997 | Ward et al. |
| 5,630,425 A | 5/1997 | Panescu et al. |
| 5,630,794 A | 5/1997 | Lax et al. |
| 5,634,471 A | 6/1997 | Fairfax et al. |
| 5,641,326 A | 6/1997 | Adams |
| 5,647,870 A | 7/1997 | Kordis et al. |
| 5,660,175 A | 8/1997 | Dayal |
| 5,678,535 A | 10/1997 | DiMarco |
| 5,680,860 A | 10/1997 | Imran |
| 5,681,280 A | 10/1997 | Rusk et al. |
| 5,681,308 A | 10/1997 | Edwards et al. |
| 5,687,723 A | 11/1997 | Avitall |
| 5,688,267 A | 11/1997 | Panescu et al. |
| 5,693,078 A | 12/1997 | Desai et al. |
| 5,694,934 A | 12/1997 | Edelman |
| 5,695,471 A | 12/1997 | Wampler |
| 5,699,799 A | 12/1997 | Xu et al. |
| 5,702,386 A | 12/1997 | Stern et al. |
| 5,707,218 A | 1/1998 | Maher et al. |
| 5,707,336 A | 1/1998 | Rubin |
| 5,707,352 A | 1/1998 | Sekins et al. |
| 5,722,401 A | 3/1998 | Pietroski et al. |
| 5,722,403 A | 3/1998 | McGee et al. |
| 5,722,416 A | 3/1998 | Swanson et al. |
| 5,725,525 A | 3/1998 | Kordis |
| 5,727,569 A | 3/1998 | Benetti et al. |
| 5,728,094 A | 3/1998 | Edwards |
| 5,730,128 A | 3/1998 | Pomeranz et al. |
| 5,730,704 A | 3/1998 | Avitall |
| 5,730,726 A | 3/1998 | Klingenstein |
| 5,730,741 A | 3/1998 | Horzewski et al. |
| 5,735,846 A | 4/1998 | Panescu et al. |
| 5,740,808 A | 4/1998 | Panescu et al. |
| 5,741,248 A | 4/1998 | Stern et al. |
| 5,752,518 A | 5/1998 | McGee et al. |
| 5,755,714 A | 5/1998 | Murphy-Chutorian |
| 5,755,715 A | 5/1998 | Stern et al. |
| 5,755,753 A | 5/1998 | Knowlton |
| 5,759,158 A | 6/1998 | Swanson |
| 5,765,568 A | 6/1998 | Sweezer, Jr. et al. |
| 5,769,846 A | 6/1998 | Edwards et al. |
| 5,772,590 A | 6/1998 | Webster, Jr. |
| 5,779,669 A | 7/1998 | Haissaguerre et al. |
| 5,779,698 A | 7/1998 | Clayman et al. |
| 5,782,239 A | 7/1998 | Webster, Jr. |
| 5,782,797 A | 7/1998 | Schweich, Jr. et al. |
| 5,782,827 A | 7/1998 | Gough et al. |
| 5,782,848 A | 7/1998 | Lennox |
| 5,782,899 A | 7/1998 | Imran |
| 5,792,064 A | 8/1998 | Panescu et al. |
| 5,795,303 A | 8/1998 | Swanson et al. |
| 5,800,375 A | 9/1998 | Sweezer et al. |
| 5,807,306 A | 9/1998 | Shapland et al. |
| 5,810,757 A | 9/1998 | Sweezer, Jr. et al. |
| 5,810,807 A | 9/1998 | Ganz et al. |
| 5,817,028 A | 10/1998 | Anderson |
| 5,817,073 A | 10/1998 | Krespi |
| 5,820,554 A | 10/1998 | Davis et al. |
| 5,823,189 A | 10/1998 | Kordis |
| 5,827,277 A | 10/1998 | Edwards |
| 5,833,651 A | 11/1998 | Donovan et al. |
| 5,836,905 A | 11/1998 | Lemelson et al. |
| 5,836,947 A | 11/1998 | Fleischman et al. |
| 5,837,001 A | 11/1998 | Mackey |
| 5,843,075 A | 12/1998 | Taylor |
| 5,843,077 A | 12/1998 | Edwards |
| 5,846,238 A | 12/1998 | Jackson et al. |
| 5,848,969 A | 12/1998 | Panescu et al. |
| 5,848,972 A | 12/1998 | Triedman et al. |
| 5,849,026 A | 12/1998 | Zhou et al. |
| 5,855,577 A | 1/1999 | Murphy-Chutorian et al. |
| 5,860,974 A | 1/1999 | Abele |
| 5,863,291 A | 1/1999 | Schaer |
| 5,865,791 A | 2/1999 | Whayne et al. |
| 5,868,740 A | 2/1999 | LeVeen et al. |
| 5,871,443 A | 2/1999 | Edwards et al. |
| 5,871,523 A | 2/1999 | Fleischman et al. |
| 5,873,852 A | 2/1999 | Vigil et al. |
| 5,873,865 A | 2/1999 | Horzewski et al. |
| 5,876,340 A | 3/1999 | Tu et al. |
| 5,876,399 A | 3/1999 | Chia et al. |
| 5,881,727 A | 3/1999 | Edwards |
| 5,882,346 A | 3/1999 | Pomeranz et al. |
| 5,891,135 A | 4/1999 | Jackson et al. |
| 5,891,136 A | 4/1999 | McGee et al. |
| 5,891,138 A | 4/1999 | Tu et al. |
| 5,893,847 A | 4/1999 | Kordis |
| 5,897,554 A | 4/1999 | Chia et al. |
| 5,899,882 A | 5/1999 | Waksman et al. |
| 5,904,651 A | 5/1999 | Swanson et al. |
| 5,904,711 A | 5/1999 | Flom et al. |
| 5,906,636 A | 5/1999 | Casscells, III et al. |
| 5,908,445 A | 6/1999 | Whayne et al. |
| 5,908,446 A | 6/1999 | Imran |
| 5,908,839 A | 6/1999 | Levitt et al. |
| 5,911,218 A | 6/1999 | DiMarco |
| 5,916,235 A | 6/1999 | Guglielmi |
| 5,919,147 A | 7/1999 | Jain |
| 5,919,172 A | 7/1999 | Golba, Jr. |
| 5,924,424 A | 7/1999 | Stevens et al. |
| 5,928,228 A | 7/1999 | Kordis et al. |
| 5,931,835 A | 8/1999 | Mackey |
| 5,935,079 A | 8/1999 | Swanson et al. |

(56) References Cited

U.S. PATENT DOCUMENTS

| | | |
|---|---|---|
| 5,941,869 A | 8/1999 | Patterson et al. |
| 5,951,494 A | 9/1999 | Wang et al. |
| 5,951,546 A | 9/1999 | Lorentzen |
| 5,954,661 A | 9/1999 | Greenspon et al. |
| 5,954,662 A | 9/1999 | Swanson et al. |
| 5,954,717 A | 9/1999 | Behl et al. |
| 5,957,961 A | 9/1999 | Maguire et al. |
| 5,964,753 A | 10/1999 | Edwards |
| 5,964,796 A | 10/1999 | Imran |
| 5,971,983 A | 10/1999 | Lesh |
| 5,972,026 A | 10/1999 | Laufer et al. |
| 5,976,175 A | 11/1999 | Hirano et al. |
| 5,976,709 A | 11/1999 | Kageyama et al. |
| 5,979,456 A | 11/1999 | Magovern |
| 5,980,563 A | 11/1999 | Tu et al. |
| 5,984,917 A | 11/1999 | Fleischman et al. |
| 5,984,971 A | 11/1999 | Faccioli et al. |
| 5,991,650 A | 11/1999 | Swanson et al. |
| 5,992,419 A | 11/1999 | Sterzer et al. |
| 5,993,462 A | 11/1999 | Pomeranz et al. |
| 5,997,534 A | 12/1999 | Tu et al. |
| 5,999,855 A | 12/1999 | DiMarco |
| 6,001,054 A | 12/1999 | Regulla et al. |
| 6,003,517 A | 12/1999 | Sheffield et al. |
| 6,004,269 A | 12/1999 | Crowley et al. |
| 6,006,755 A | 12/1999 | Edwards |
| 6,008,211 A | 12/1999 | Robinson et al. |
| 6,009,877 A | 1/2000 | Edwards |
| 6,010,500 A | 1/2000 | Sherman et al. |
| 6,014,579 A | 1/2000 | Pomeranz et al. |
| 6,016,437 A | 1/2000 | Tu et al. |
| 6,023,638 A | 2/2000 | Swanson |
| 6,024,740 A | 2/2000 | Lesh et al. |
| 6,029,091 A | 2/2000 | de la Rama et al. |
| 6,033,397 A | 3/2000 | Laufer et al. |
| 6,036,687 A | 3/2000 | Laufer et al. |
| 6,036,689 A | 3/2000 | Tu et al. |
| 6,039,731 A | 3/2000 | Taylor et al. |
| 6,042,580 A * | 3/2000 | Simpson .................... 606/32 |
| 6,045,549 A | 4/2000 | Smethers et al. |
| 6,045,550 A | 4/2000 | Simpson et al. |
| 6,050,992 A | 4/2000 | Nichols |
| 6,053,172 A | 4/2000 | Hovda et al. |
| 6,053,909 A | 4/2000 | Shadduck |
| 6,056,744 A | 5/2000 | Edwards |
| 6,056,769 A | 5/2000 | Epstein et al. |
| 6,063,078 A | 5/2000 | Wittkampf |
| 6,071,280 A | 6/2000 | Edwards et al. |
| 6,071,281 A | 6/2000 | Burnside et al. |
| 6,071,282 A | 6/2000 | Fleischman |
| 6,083,255 A | 7/2000 | Laufer et al. |
| 6,090,104 A | 7/2000 | Webster, Jr. |
| 6,092,528 A | 7/2000 | Edwards |
| 6,102,886 A | 8/2000 | Lundquist et al. |
| 6,106,522 A | 8/2000 | Fleischman et al. |
| 6,106,524 A | 8/2000 | Eggers et al. |
| 6,123,702 A | 9/2000 | Swanson et al. |
| 6,123,703 A | 9/2000 | Tu et al. |
| 6,129,725 A | 10/2000 | Tu et al. |
| 6,139,527 A | 10/2000 | Laufer et al. |
| 6,139,571 A | 10/2000 | Fuller et al. |
| 6,142,993 A | 11/2000 | Whayne et al. |
| 6,143,013 A | 11/2000 | Samson et al. |
| 6,149,647 A | 11/2000 | Tu et al. |
| 6,152,143 A | 11/2000 | Edwards |
| 6,152,899 A | 11/2000 | Farley et al. |
| 6,159,194 A | 12/2000 | Eggers et al. |
| 6,179,833 B1 | 1/2001 | Taylor |
| 6,183,468 B1 | 2/2001 | Swanson et al. |
| 6,198,970 B1 | 3/2001 | Freed et al. |
| 6,200,311 B1 | 3/2001 | Danek et al. |
| 6,200,332 B1 | 3/2001 | Del Giglio |
| 6,200,333 B1 | 3/2001 | Laufer |
| 6,210,367 B1 | 4/2001 | Carr |
| 6,212,433 B1 | 4/2001 | Behl |
| 6,214,002 B1 | 4/2001 | Fleischman et al. |
| 6,216,043 B1 | 4/2001 | Swanson et al. |
| 6,216,044 B1 | 4/2001 | Kordis |
| 6,217,576 B1 | 4/2001 | Tu et al. |
| 6,235,024 B1 | 5/2001 | Tu |
| 6,241,727 B1 | 6/2001 | Tu et al. |
| 6,245,065 B1 | 6/2001 | Panescu et al. |
| 6,254,598 B1 | 7/2001 | Edwards et al. |
| 6,258,087 B1 | 7/2001 | Edwards et al. |
| 6,264,653 B1 | 7/2001 | Falwell |
| 6,269,813 B1 | 8/2001 | Fitzgerald et al. |
| 6,270,476 B1 | 8/2001 | Santoianni et al. |
| 6,273,907 B1 | 8/2001 | Laufer |
| 6,283,988 B1 | 9/2001 | Laufer et al. |
| 6,283,989 B1 | 9/2001 | Laufer et al. |
| 6,287,304 B1 | 9/2001 | Eggers et al. |
| 6,296,639 B1 | 10/2001 | Truckai et al. |
| 6,319,251 B1 * | 11/2001 | Tu et al. .................... 606/41 |
| 6,322,559 B1 | 11/2001 | Daulton et al. |
| 6,322,584 B2 | 11/2001 | Ingle et al. |
| 6,338,727 B1 | 1/2002 | Noda et al. |
| 6,338,836 B1 | 1/2002 | Kuth et al. |
| 6,346,104 B2 | 2/2002 | Daly et al. |
| 6,355,031 B1 | 3/2002 | Edwards et al. |
| 6,379,352 B1 | 4/2002 | Reynolds et al. |
| 6,409,723 B1 | 6/2002 | Edwards |
| 6,411,852 B1 | 6/2002 | Danek et al. |
| 6,416,511 B1 | 7/2002 | Lesh et al. |
| 6,416,740 B1 | 7/2002 | Unger |
| 6,423,105 B1 | 7/2002 | Iijima et al. |
| 6,425,895 B1 | 7/2002 | Swanson et al. |
| 6,440,129 B1 | 8/2002 | Simpson |
| 6,442,435 B2 | 8/2002 | King et al. |
| 6,458,121 B1 | 10/2002 | Rosenstock et al. |
| 6,460,545 B2 | 10/2002 | Kordis |
| 6,488,673 B1 | 12/2002 | Laufer et al. |
| 6,488,679 B1 | 12/2002 | Swanson et al. |
| 6,493,589 B1 | 12/2002 | Medhkour et al. |
| 6,494,880 B1 | 12/2002 | Swanson et al. |
| 6,496,738 B2 | 12/2002 | Carr |
| 6,514,246 B1 | 2/2003 | Swanson et al. |
| 6,526,320 B2 | 2/2003 | Mitchell |
| 6,529,756 B1 | 3/2003 | Phan et al. |
| 6,544,226 B1 | 4/2003 | Gaiser et al. |
| 6,544,262 B2 | 4/2003 | Fleischman |
| 6,547,788 B1 | 4/2003 | Maguire et al. |
| 6,558,378 B2 | 5/2003 | Sherman et al. |
| 6,572,612 B2 | 6/2003 | Stewart et al. |
| 6,575,623 B2 | 6/2003 | Werneth |
| 6,575,969 B1 | 6/2003 | Rittman, III et al. |
| 6,582,427 B1 | 6/2003 | Goble et al. |
| 6,582,430 B2 | 6/2003 | Hall |
| 6,589,235 B2 | 7/2003 | Wong et al. |
| 6,610,054 B1 | 8/2003 | Edwards et al. |
| 6,620,159 B2 | 9/2003 | Hegde |
| 6,626,903 B2 | 9/2003 | McGuckin, Jr. et al. |
| 6,634,363 B1 | 10/2003 | Danek et al. |
| 6,635,056 B2 | 10/2003 | Kadhiresan et al. |
| 6,638,273 B1 | 10/2003 | Farley et al. |
| 6,640,120 B1 | 10/2003 | Swanson et al. |
| 6,645,200 B1 | 11/2003 | Koblish et al. |
| 6,652,548 B2 | 11/2003 | Evans et al. |
| 6,669,693 B2 | 12/2003 | Friedman |
| 6,673,068 B1 | 1/2004 | Berube |
| 6,692,492 B2 | 2/2004 | Simpson et al. |
| 6,699,243 B2 | 3/2004 | West et al. |
| 6,714,822 B2 | 3/2004 | King et al. |
| 6,723,091 B2 | 4/2004 | Goble et al. |
| 6,743,197 B1 | 6/2004 | Edwards |
| 6,749,604 B1 | 6/2004 | Eggers et al. |
| 6,749,606 B2 | 6/2004 | Keast et al. |
| 6,767,347 B2 | 7/2004 | Sharkey et al. |
| 6,770,070 B1 | 8/2004 | Balbierz |
| 6,802,843 B2 | 10/2004 | Truckai et al. |
| 6,805,131 B2 | 10/2004 | Kordis |
| 6,837,888 B2 | 1/2005 | Ciarrocca et al. |
| 6,840,243 B2 | 1/2005 | Deem et al. |
| 6,849,073 B2 | 2/2005 | Hoey et al. |
| 6,852,091 B2 | 2/2005 | Edwards et al. |

(56) References Cited

U.S. PATENT DOCUMENTS

| | | |
|---|---|---|
| 6,852,110 B2 | 2/2005 | Roy et al. |
| 6,866,662 B2 | 3/2005 | Fuimaono et al. |
| 6,881,213 B2 | 4/2005 | Ryan et al. |
| 6,893,436 B2 | 5/2005 | Woodard et al. |
| 6,893,439 B2 | 5/2005 | Fleischman |
| 6,895,267 B2 | 5/2005 | Panescu et al. |
| 6,904,303 B2 | 6/2005 | Phan et al. |
| 6,917,834 B2 | 7/2005 | Koblish et al. |
| 6,939,346 B2 | 9/2005 | Kannenberg et al. |
| 6,954,977 B2 | 10/2005 | Maguire et al. |
| 7,027,869 B2 | 4/2006 | Danek et al. |
| 7,043,307 B1 | 5/2006 | Zelickson et al. |
| 7,104,987 B2 | 9/2006 | Biggs et al. |
| 7,104,990 B2 | 9/2006 | Jenkins et al. |
| 7,118,568 B2 | 10/2006 | Hassett et al. |
| 7,122,033 B2 | 10/2006 | Wood |
| 7,131,445 B2 | 11/2006 | Amoah |
| 7,186,251 B2 | 3/2007 | Malecki et al. |
| 7,198,635 B2 | 4/2007 | Danek et al. |
| 7,200,445 B1 | 4/2007 | Dalbec et al. |
| 7,241,295 B2 | 7/2007 | Maguire |
| 7,255,693 B1 | 8/2007 | Johnston et al. |
| 7,264,002 B2 | 9/2007 | Danek et al. |
| 7,266,414 B2 | 9/2007 | Cornelius et al. |
| 7,273,055 B2 | 9/2007 | Danek et al. |
| 7,425,212 B1 | 9/2008 | Danek et al. |
| 7,542,802 B2 | 6/2009 | Biggs et al. |
| 7,556,624 B2 | 7/2009 | Laufer et al. |
| 7,740,017 B2 | 6/2010 | Danek et al. |
| 2002/0091379 A1 | 7/2002 | Danek et al. |
| 2003/0050631 A1 | 3/2003 | Mody et al. |
| 2003/0065371 A1 | 4/2003 | Satake |
| 2003/0069570 A1 | 4/2003 | Witzel et al. |
| 2003/0187430 A1 | 10/2003 | Vorisek |
| 2003/0236455 A1 | 12/2003 | Swanson et al. |
| 2004/0010289 A1 | 1/2004 | Biggs et al. |
| 2004/0031494 A1 | 2/2004 | Danek et al. |
| 2004/0153056 A1 | 8/2004 | Muller et al. |
| 2004/0182399 A1 | 9/2004 | Danek et al. |
| 2004/0249401 A1 | 12/2004 | Rabiner et al. |
| 2005/0010270 A1 | 1/2005 | Laufer |
| 2005/0096644 A1 | 5/2005 | Hall et al. |
| 2005/0171396 A1 | 8/2005 | Pankratov et al. |
| 2005/0193279 A1 | 9/2005 | Daners |
| 2005/0203503 A1 | 9/2005 | Edwards et al. |
| 2005/0240176 A1 | 10/2005 | Oral et al. |
| 2005/0251128 A1 | 11/2005 | Amoah |
| 2006/0062808 A1 | 3/2006 | Laufer et al. |
| 2006/0079887 A1 | 4/2006 | Buysse et al. |
| 2006/0089637 A1 | 4/2006 | Werneth et al. |
| 2006/0135953 A1 | 6/2006 | Kania et al. |
| 2006/0137698 A1 | 6/2006 | Danek et al. |
| 2006/0247617 A1 | 11/2006 | Danek et al. |
| 2006/0247618 A1 | 11/2006 | Kaplan et al. |
| 2006/0247619 A1 | 11/2006 | Kaplan et al. |
| 2006/0247726 A1 | 11/2006 | Biggs et al. |
| 2006/0247727 A1 | 11/2006 | Biggs et al. |
| 2006/0247746 A1 | 11/2006 | Danek et al. |
| 2006/0254600 A1 | 11/2006 | Danek et al. |
| 2006/0278243 A1 | 12/2006 | Danek et al. |
| 2006/0278244 A1 | 12/2006 | Danek et al. |
| 2006/0282071 A1 | 12/2006 | Utley et al. |
| 2007/0074719 A1 | 4/2007 | Danek et al. |
| 2007/0083194 A1 | 4/2007 | Kunis et al. |
| 2007/0083197 A1 | 4/2007 | Danek et al. |
| 2007/0102011 A1 | 5/2007 | Danek et al. |
| 2007/0106292 A1 | 5/2007 | Kaplan et al. |
| 2007/0106296 A1 | 5/2007 | Laufer et al. |
| 2007/0106348 A1 | 5/2007 | Laufer |
| 2007/0118184 A1 | 5/2007 | Danek et al. |
| 2007/0118190 A1 | 5/2007 | Danek et al. |
| 2007/0123958 A1 | 5/2007 | Laufer |
| 2007/0123961 A1 | 5/2007 | Danek et al. |
| 2007/0129720 A1 | 6/2007 | Demarais et al. |
| 2008/0004596 A1 | 1/2008 | Yun et al. |
| 2008/0097424 A1 | 4/2008 | Wizeman et al. |
| 2008/0255642 A1 | 10/2008 | Zarins et al. |
| 2009/0018538 A1 | 1/2009 | Webster et al. |
| 2009/0030477 A1 | 1/2009 | Jarrard |
| 2009/0043301 A1 | 2/2009 | Jarrard et al. |
| 2009/0069797 A1 | 3/2009 | Danek et al. |
| 2009/0112203 A1 | 4/2009 | Danek et al. |
| 2009/0143705 A1 | 6/2009 | Danek et al. |
| 2009/0143776 A1 | 6/2009 | Danek et al. |
| 2009/0192505 A1 | 7/2009 | Askew et al. |
| 2009/0192508 A1 | 7/2009 | Laufer et al. |
| 2009/0306644 A1 | 12/2009 | Mayse et al. |

FOREIGN PATENT DOCUMENTS

| | | |
|---|---|---|
| EP | 286145 A2 | 10/1988 |
| EP | 280225 A3 | 3/1989 |
| EP | 286145 A3 | 10/1990 |
| EP | 282225 B1 | 6/1992 |
| EP | 908713 A1 | 4/1999 |
| EP | 908150 B1 | 5/2003 |
| EP | 768091 B1 | 7/2003 |
| EP | 1297795 B1 | 8/2005 |
| FR | 2659240 B1 | 7/1997 |
| GB | 2233293 A | 1/1991 |
| GB | 2233293 B | 2/1994 |
| JP | 59167707 A2 | 9/1984 |
| JP | 7289557 A | 11/1995 |
| JP | 9047518 A2 | 2/1997 |
| JP | 9243837 A2 | 9/1997 |
| JP | 10026709 A2 | 1/1998 |
| RU | 2053814 C1 | 2/1996 |
| RU | 2091054 C1 | 9/1997 |
| SU | 545358 T | 2/1977 |
| WO | 8911311 A1 | 11/1989 |
| WO | 9304734 A1 | 3/1993 |
| WO | 9502370 A3 | 3/1995 |
| WO | 9510322 A1 | 4/1995 |
| WO | 9604860 A1 | 2/1996 |
| WO | 9610961 A1 | 4/1996 |
| WO | 9732532 A1 | 9/1997 |
| WO | 9733715 A1 | 9/1997 |
| WO | 9737715 A1 | 10/1997 |
| WO | 9740751 A1 | 11/1997 |
| WO | 9844854 A1 | 10/1998 |
| WO | 9852480 A1 | 11/1998 |
| WO | 9856234 A1 | 12/1998 |
| WO | 9856324 A1 | 12/1998 |
| WO | 9903413 A1 | 1/1999 |
| WO | 9858681 A3 | 3/1999 |
| WO | 9913779 A2 | 3/1999 |
| WO | 9932040 A1 | 7/1999 |
| WO | 9934741 A1 | 7/1999 |
| WO | 9944506 A1 | 9/1999 |
| WO | 9945855 A1 | 9/1999 |
| WO | 9964109 A1 | 12/1999 |
| WO | 0051510 A1 | 9/2000 |
| WO | 0062699 A3 | 10/2000 |
| WO | 0103642 A1 | 1/2001 |
| WO | 0232333 A1 | 4/2002 |
| WO | 0232334 A1 | 4/2002 |
| WO | 2009082433 A2 | 7/2009 |
| WO | 2009137819 A1 | 11/2009 |

OTHER PUBLICATIONS

Bel E.H., ""Hot stuff": Bronchial Thermoplasty for Asthma," American Journal of Respiratory and Critical Care Medicine, 2006, 173 (9), 941-943.

Brown R.H., et al., "Effect of Bronchial Thermoplasty on Airway Distensibility," European Respiratory Journal, 2005, 26 (2), 277-282.

Brown R.H., et al., "In Vivo evaluation of the Effectiveness of Bronchial Thermoplasty with Computed Tomography," Journal of Applied Physiology, 2005, 98 (5), 1603-1606.

Chhajed P.N., et al., "Will there be a Role for Bronchoscopic Radiofrequency Ablation", Journal of Bronchology, 2005, 12 (3), 184-186.

Co-pending U.S. Appl. No. 09/095,323, filed Jun. 10, 1998.

(56) References Cited

OTHER PUBLICATIONS

Co-pending U.S. Appl. No. 09/244,173, filed Feb. 4, 1999.
Co-pending U.S. Appl. No. 12/640,644, filed Dec. 17, 2009.
Co-pending U.S. Appl. No. 12/727,156, filed Mar. 18, 2010.
Co-pending U.S. Appl. No. 12/765,704, filed Apr. 22, 2010.
Cox G., et al., "Asthma Control during the Year after Bronchial Thermoplasty," New England journal of medicine, 2007, 356 (13), 1327-1337.
Cox G., et al., "Asthma Intervention Research (AIR) Trial Evaluating Bronchial Thermoplasty: Early Results," American Thoracic Society Annual Meeting, 2002, 1 page.
Cox G., et al., "Bronchial Thermoplasty for Asthma," American Journal of Respiratory and Critical Care Medicine, 2006, 173 (9), 965-969.
Cox G., et al., "Bronchial Thermoplasty: Long-Term Follow-Up and Patient Satisfaction," Chest, 2004, 126 (4), 822s.
Cox G., et al., "Bronchial Thermoplasty: One-Year Update, American Thoracic Society Annual Meeting," American Journal of Respiratory and Critical Care Medicine, 2004, 169, A313.
Cox G., et al., "Clinical Experience with Bronchial Thermoplasty for the Treatment of Asthma," Chest, 2003, 124, 106S.
Cox G., et al., "Development of a Novel Bronchoscopic Therapy for Asthma," Journal of Allergy and Clinical Immunology, 2003, 113 (2), S33.
Cox G., et al., "Early Clinical Experience with Bronchial Thermoplasty for the Treatment of Asthma," American Thoracic Society Annual Meeting, 2002, 1068.
Cox G., et al., "Impact of Bronchial Thermoplasty on Asthma Status: Interim Results from the AIR Trial," 2006, 1 page.
Cox G., et al., "Radiofrequency Ablation of Airway Smooth Muscle for Sustained Treatment of Asthma: Preliminary Investigations," European Respiratory Journal, 2004, 24 (4), 659-663.
Danek C.J., et al., "Bronchial Thermoplasty Reduces Canine Airway Responsiveness to Local Methacholine Challenge," American Thoracic Society Annual Meeting, 2002, 1 page.
Danek C.J., et al., "Reduction in Airway Hyperresponsiveness to Methacholine by the Application of RF Energy in Dogs," Journal of Applied Physiology, 2004, 97 (5), 1946-1953.
Dierkesmann R., "Indication and Results of Endobronchial Laser Therapy," Lung, 1990, 168, 1095-1102.
Hogg J. C., "The Pathology of Asthma," APMIS, 1997, 105 (10), 735-745.
International Search Report for Application No. PCT/US00/05412, mailed on Jun. 20, 2000, 2 pages.
International Search Report for Application No. PCT/US00/18197, mailed on Oct. 3, 2000, 1 page.
International Search Report for Application No. PCT/US00/28745, mailed on Mar. 28, 2001, 6 pages.
International Search Report for Application No. PCT/US01/32321, mailed on Jan. 18, 2002, 2 pages.
International Search Report for Application No. PCT/US98/03759, mailed on Jul. 30, 1998, 1 page.
International Search Report for Application No. PCT/US98/26227, mailed on Mar. 25, 1999, 1 page.
International Search Report for Application No. PCT/US99/00232, mailed on Mar. 4, 1999, 1 page.
International Search Report for Application No. PCT/US99/12986, mailed on Sep. 29, 1999, 1 page.
Ivanyuta O.M., et al., "Effect of Low-Power Laser Irradiation of Bronchial Mucosa on the State of Systemic and Local Immunity in Patients with Chronic Bronchitis," Problemy Tuberkuleza, 1991, 6, 26-29.
James A.L., et al., "The Mechanics of Airway Narrowing in Asthma," American Review of Respiratory Diseases, 1989, 139 (1), 242-246.
Johnson S. R., et al., "Synthetic Functions of Airway Smooth Muscle in Asthma," Trends Pharmacol. Sci., 1997, 18 (8), 288-292.
Kitamura S., "Color Atlas of Clinical Application of Fiberoptic Bronchoscopy," 1990, Year Book Medical Publishers, 2 pages.
Laviolette M., et al., "Asthma Intervention Research (AIR) Trial: Early Safety Assessment of Bronchial Thermoplasty," American Journal of Respiratory and Critical Care Medicine, 2004, 169, A314.
Leff A., et al., "Bronchial Thermoplasty Alters Airway Smooth Muscle and Reduces Responsiveness in Dogs: A Possible Procedure for the Treatment of Asthma," American Thoracic Society Annual Meeting, 2002, 1 page.
Lim E.C., et al., "Botulinum Toxin: A Novel Therapeutic Option for Bronchial Asthma", Medical Hypotheses, 2006, 66 (5), 915-919.
Lombard C.M., et al., "Histologic Effects of Bronchial Thermoplasty of Canine and Human Airways,"American Thoracic Society Annual Meeting, 2002, 1 page.
Macklem P. T., "Mechanical Factors Determining Maximum Bronchoconstriction," European Respiratory Journal, 1989, 6, 516s-519s.
Mayse M.L., et al., "Clinical Pearls for Bronchial Thermoplasty," Journal of Bronchology, 2007, 14 (2), 115-123.
Miller J.D., et al., "A Prospective Feasibility Study of Bronchial Thermoplasty in the Human Airway," Chest, 2005, 127 (6), 1999-2006.
Miller J.D., et al., "Bronchial Thermoplasty is Well Tolerated by Non-Asthmatic Patients Requiring Lobectomy," American Thoracic Society Annual Meeting, 2002, 1 page.
Mitzner W., "Airway Smooth Muscle the Appendix of the Lung," American Journal of Respiratory and Critical Care Medicine, 2004, 169 (7), 787-790.
Netter F.H., "Respiratory System: A Compilation of Paintings Depicting Anatomy and Embryology, Physiology, Pathology, Pathophysiology, and Clinical Features and Treatment of Diseases,in the CIBA Collection of Medical Illustrations M.B. Divertie, ed., Summit: New Jerse," 1979, 7, 119-135.
Notice of final Rejection, Japanese Patent Application No. 2000-553172, dated Sep. 2, 2008, 5 pages.
Provotorov V.M., et al., "The Clinical Efficacy of Treating Patients with Nonspecific Lung Diseases Using Low-energy Laser Irradiation and Intrapulmonary Drug Administration," Terapevticheskii Arkhiv, 1991, 62 (12), 18-23.
Rubin A., et al., "Bronchial Thermoplasty Improves Asthma Status of Moderate to Severe Perisstent Asthmatics Over and Above Current Standard-of-Care," American College of Chest Physicians, 2006, 2 pages.
Shesterina M.V., et al., "Effect of Laser Therapy on Immunity in Patients with Bronchial Asthma and Pulmonary Tuberculosis," Problemy Tuberkuleza, 1994, 5, 23-26.
Solway J., et al., "Airway Smooth Muscle as a Target for Asthma Therapy," New England Journal of medicine, 2007, 356 (13), 1367-1369.
Sterk P.J., et al., "Heterogeneity of Airway Hyperresponsiveness: Time for Unconventional, But Traditional, Studies," Journal of Applied Physiology, 2004, 96 (6), 2017-2018.
Toma T.P., et al., "Brave New World for Interventional Bronchoscopy," Thorax, 2005, 60 (3), 180-181.
Trow T.K., "Clinical Year in Review I: Diagnostic Imaging, Asthma, Lung Transplantation, and Interventional Pulmonology," Proceedings of the American Thoracic Society, 2006, 3 (7), 553-556.
Vasilotta P.L., et al., "I-R Laser: A New Therapy in Rhino-Sino-Nasal Bronchial Syndrome with Asthmatic Component," American Society for Laser Medicine and Surgery Abstracts, 74. 1993.
Vorotnev A.I., et al., "The Treatment of Patients with Chronic Obstructive Bronchitis by Using a Low-power Laser at a General Rehabilitation Center," Terapevticheskii Arkhiv, 1997, 69 (3), 17-19.
Wiggs B.R., et al., "On the Mechanism of Mucosal Folding in Normal and Asthmatic Airways," Journal of Applied Physiology, 1997, 83 (6), 1814-1821.
Wilson S.R., et al., "Global Assessment after Bronchial Thermoplasty: The Patients Perspective," Journal of Outcomes Research, 2006, 10, 37-46.
Wizeman W., et al., "A Computer Model of Thermal Treatment of Airways by Radiofrequency (RF) Energy Delivery," American Thoracic Society Annual Meeting, 2007, 1 page.

* cited by examiner

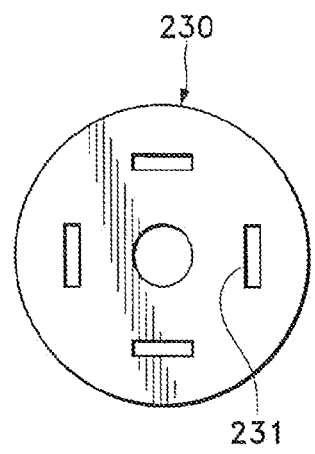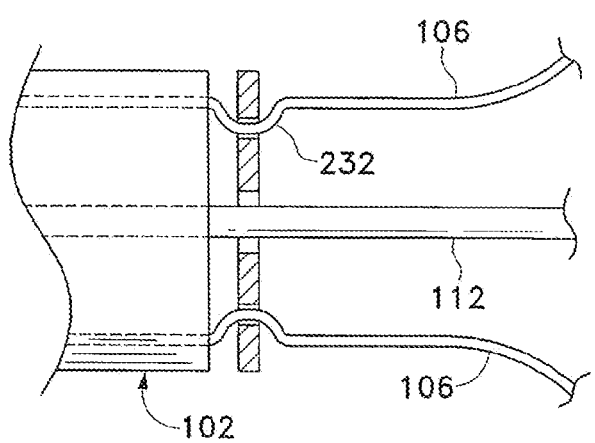
FIG. 6F    FIG. 6G
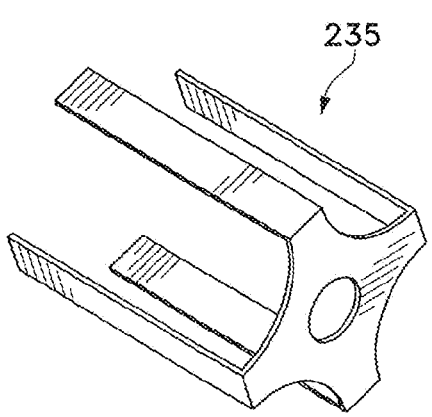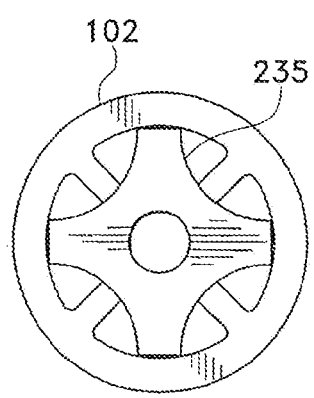
FIG. 6H    FIG. 6I

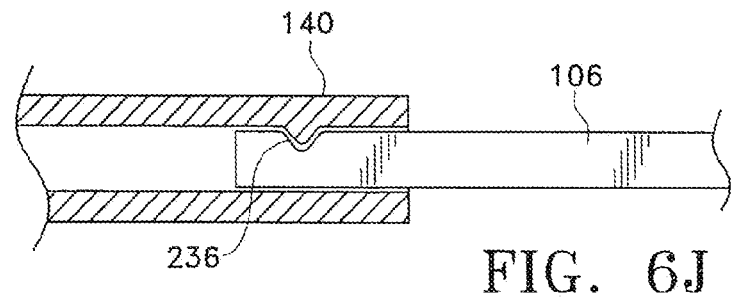
FIG. 6J
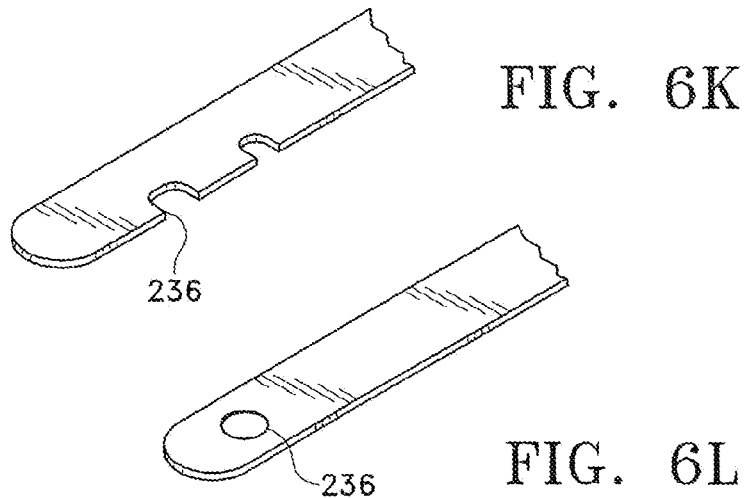
FIG. 6K
FIG. 6L
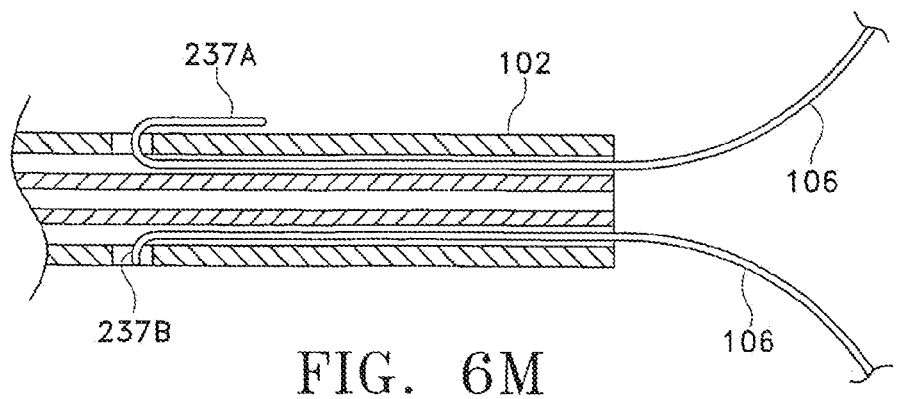
FIG. 6M

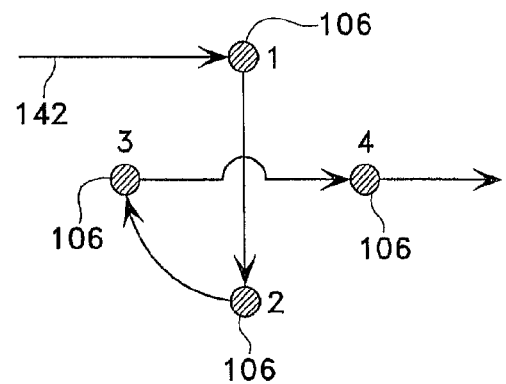
FIG. 7A
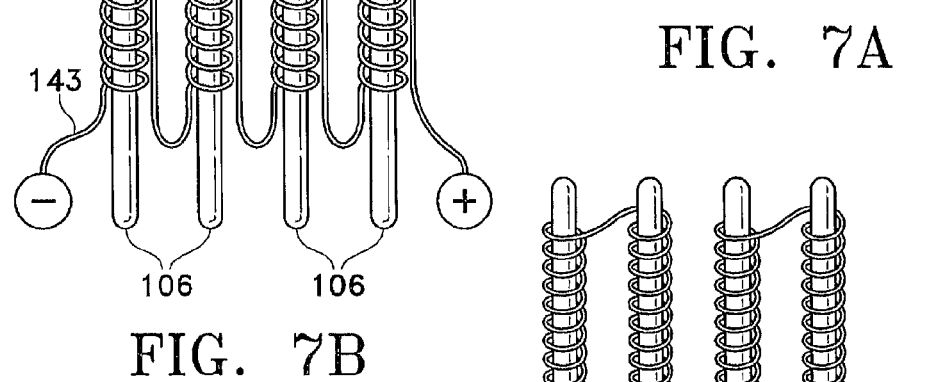
FIG. 7B
FIG. 7C
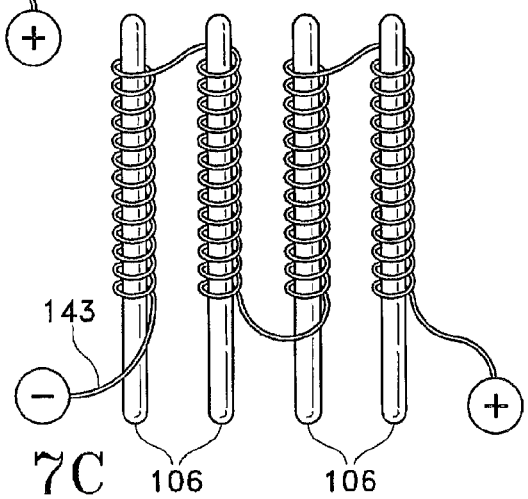
FIG. 7D
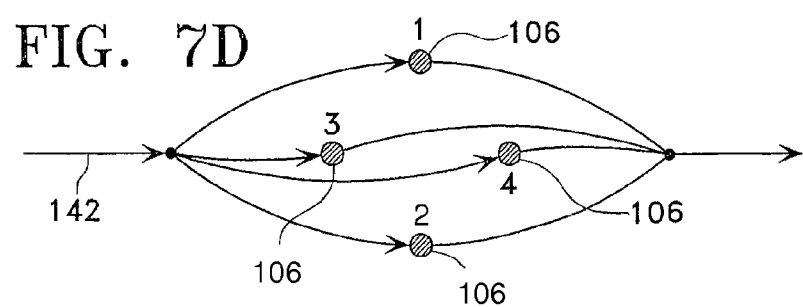

MODIFICATION OF AIRWAYS BY APPLICATION OF ENERGY

CROSS REFERENCE TO RELATED APPLICATIONS

This application is a continuation of U.S. patent application Ser. No. 13/557,485, filed Jul. 25, 2012, now U.S. Pat. No. 8,465,486, which is a continuation of U.S. patent application Ser. No. 11/534,621, filed Sep. 22, 2006, now U.S. Pat. No. 8,257,413, which is a continuation of U.S. patent application Ser. No. 10/414,253, filed Apr. 14, 2003, now U.S. Pat. No. 7,198,635, which is a continuation of International Application No. PCT/US00/28745, filed Oct. 17, 2000. All the above applications are incorporated by reference herein in their entirety.

BACKGROUND OF THE INVENTION

1. Field of the Invention

The invention relates to methods of treating a lung having at least one symptom of reversible obstructive pulmonary disease, and more particularly, the invention relates to devices for transferring energy into airway tissue to at least reduce the ability of the lung to produce at least one of the symptoms of reversible obstructive pulmonary disease. The invention includes additional steps that reduce the ability of the lung to produce at least one of the symptoms of reversible obstructive pulmonary disease and to reduce the resistance to the flow of air through a lung.

2. Brief Description of the Related Art

Reversible obstructive pulmonary disease includes asthma and reversible aspects of chronic obstructive pulmonary disease (COPD). Asthma is a disease in which (i) bronchoconstriction, (ii) excessive mucus production, and (iii) inflammation and swelling of airways occur, causing widespread but variable airflow obstruction thereby making it difficult for the asthma sufferer to breathe. Asthma is a chronic disorder, primarily characterized by persistent airway inflammation. Asthma is further characterized by acute episodes of additional airway narrowing via contraction of hyper-responsive airway smooth muscle.

The reversible aspects of COPD generally describe excessive mucus production in the bronchial tree. Usually, there is a general increase in bulk (hypertrophy) of the large bronchi and chronic inflammatory changes in the small airways. Excessive amounts of mucus are found in the airways and semisolid plugs of mucus may occlude some small bronchi. Also, the small airways are narrowed and show inflammatory changes. The reversible aspects of COPD include partial airway occlusion by excess secretions and airway narrowing secondary to smooth muscle contraction, bronchial wall edema and inflation of the airways In asthma, chronic inflammatory processes in the airway play a central role in increasing the resistance to airflow within the lungs. Many cells and cellular elements are involved in the inflammatory process, particularly mast cells, eosinophils T lymphocytes, neutrophils, epithelial cells, and even airway smooth muscle itself. The reactions of these cells result in an associated increase in the existing sensitivity and hyper-responsiveness of the airway smooth muscle cells that line the airways to the particular stimuli involved.

The chronic nature of asthma can also lead to remodeling of the airway wall (i.e., structural changes such as thickening or edema) which can further affect the function of the airway wall and influence airway hyper-responsiveness. Other physiologic changes associated with asthma include excess mucus production, and if the asthma is severe, mucus plugging, as well as ongoing epithelial denudation and repair. Epithelial denudation exposes the underlying tissue to substances that would not normally come in contact with them, further reinforcing the cycle of cellular damage and inflammatory response.

In susceptible individuals, asthma symptoms include recurrent episodes of shortness of breath (dyspnea), wheezing, chest tightness, and cough. Currently, asthma is managed by a combination of stimulus avoidance and pharmacology.

Stimulus avoidance is accomplished via systematic identification and minimization of contact with each type of stimuli. It may, however, be impractical and not always helpful to avoid all potential stimuli.

Asthma is managed pharmacologically by: (1) long term control through use of anti-inflammatories and long-acting bronchodilators and (2) short term management of acute exacerbations through use of short-acting bronchodilators. Both of these approaches require repeated and regular use of the prescribed drugs. High doses of corticosteroid anti-inflammatory drugs can have serious side effects that require careful management. In addition, some patients are resistant to steroid treatment. The difficulty involved in patient compliance with pharmacologic management and the difficulty of avoiding stimulus that triggers asthma are common barriers to successful asthma management.

Asthma is a serious disease with growing numbers of sufferers. Current management techniques are neither completely successful nor free from side effects.

Accordingly, it would be desirable to provide an asthma treatment which improves airflow without the need for patient compliance.

In addition to the airways of the lungs, other body conduits such as the esophagus, ureter, urethra, and coronary arteries, are also subject to periodic reversible spasms that produce obstruction to flow.

SUMMARY OF THE INVENTION

The present invention relates to a device for treating airway tissue within the lungs by transfer of energy into the walls of the airway to reduce plugging of the airway, to prevent the airway from being able to constrict, to increase the inner airway diameter, or to reduce resistance to flow through the airway. The invention is particularly directed to the treatment of the airways in the lungs to reduce the effects of asthma and other lung disease. One variation of the invention includes the transfer of energy to the airway wall via the application of heat.

The present invention provides devices to decrease airway responsiveness and airway resistance to flow which may augment or replace current management techniques. In accordance with one variation of the present invention, an energy transfer apparatus for treating conditions of the lungs by decreasing airway responsiveness includes transferring energy into an airway wall to alter the airway wall in such a manner that the responsiveness of the airway is reduced.

In particular, the inventive device is an energy transfer apparatus which facilitates energy transfer with a mass of tissue within the airways of a lung. The inventive device is sized to enter the bronchus or bronchiole of a human lung to conduct energy transfer with the airway tissue therein. The inventive device may also be sized to fit within a bronchoscope. The bronchoscope may have a channel with a diameter of preferably 2 mm or less.

A variation of the inventive device includes a flexible elongated body having a proximal portion and a distal portion with a lumen extending between the proximal and distal portions. The flexible elongated body may be of sufficient stiffness to pass through a seal of a working channel of a bronchoscope and allow operation of the device through the working channel seal. The device may include an expandable portion that is adjacent to a distal portion of the elongated body. The expandable portion has a first state, e.g., a size, and a second state where the second state is radially expanded in size from the elongated body. The device may include a temperature detecting element which is placed near to the expandable portion. The device also includes at least one energy transfer element at an exterior of the expandable portion, where the energy transfer elements are configured to contact the wall of the bronchus or bronchiole when the expanded portion is in an expanded state. The device may also include a deployment member that is configured to move the expandable portion between the first and second radially expanded states. The deployment member may extend between the expandable portion and the proximal portion of the elongated body. The inventive device may further include a distal tip located at a distal end of the apparatus. One variation of the inventive device includes an expandable portion that has a diameter of less than 15 mm when in a second expanded state.

Another variation of the invention includes an expandable portion which includes pre-shaped tines. Such tines are configured to be in a first state within an elongated body and, when advanced out of the elongated body, to expand into a second expanded state. The tines may be connected to each other with an expanding element to prevent the tines from entering multiple airways at a bifurcation within the lung.

Another variation of the invention includes an expandable portion comprised of a balloon. This variation of the invention may include the use of a fluid which may expand the balloon into the second state. Yet another variation of this invention includes the use of a heat generating element in the balloon which conducts heat to the fluid to heat an exterior of the balloon. In this variation, the exterior of the balloon serves as the energy transfer element.

A further variation of the inventive device includes an expandable portion which comprises a plurality of legs which forms a basket. The legs of this variation may extend from a proximal joint that is found at an intersection of a distal portion of the elongated body to a distal joint that is adjacent to a distal tip. Each leg may have a center that is substantially parallel to the elongated body so that there is sufficient contact between the airway walls and the parallel portion of the leg. The center that is substantially parallel is usually referred to as the energy delivery or active region of the leg.

The legs of this variation may be spaced around a circumference of the elongated body to form a basket. The legs of this variation may have a circular cross section or a rectangular cross section, or a non-axisymmetric cross section. The cross sections may be chosen to allow ready deployment from a first state to a second expanded state while resisting out-of-plane bending which may distort the spacing of the legs or the contact of electrodes with the airway surface. One variation of the invention includes a basket in which the distance between the proximal and distal joint is less than 35 mm when the basket is not expanded. Another variation of this invention includes a basket that comprises four or five legs. In this case, the legs may be placed evenly around a circumference of the elongated body. In this case the legs may be found at intervals of 90 or 72 degrees. Other variations of the invention include devices having less than four legs or more than five legs. Another variation of this inventive device includes placing a temperature detecting element on one or on more legs. In this variation, the temperature of one leg may be monitored or the temperature of several legs may be independently monitored to control the energy delivery. In a further variation, multiple temperature sensing elements may be combined with independent control of energy to each leg. Both of these variations may also apply to a variation of the device having pre-shaped tines. The legs may be soldered or made to adhere using adhesives to the elongated body at the proximal and distal ends. Another variation of the invention includes a multi-lumen elongated body into which a portion of each leg is inserted. It is also contemplated that an elongated member may be reinforced via a reinforcing member. Such a reinforcing member may include a coiled or braided wire, polymeric insert, or any other similar reinforcing member.

The energy transfer element of the invention may include an element that directly heats tissue by delivering current such as an RF based electrode. The RF electrode may be either bipolar or monopolar or a heated element that conductively heats tissue. In variations of the invention using RF energy, the frequency of the RF may be selected to be in the 400 kHz range or any other standard medical range used in electro-surgical applications.

When the electrode directly heats the tissue, the heated element may use AC or DC current to resistively heat the element. RF energy may also be used to inductively or resistively heat the element. An indirect method of heating includes a resistively heated element that conducts heat to the expandable portion or directly to the airway. The invention may also include a combination of the types of electrodes mentioned above.

In the variation of the invention in which the expandable portion comprises a basket, each of the energy transfer elements may be a RF electrode that is attached to each leg. The electrode may be fastened by a heat shrink fastener. In such a case, a temperature detecting element may be placed on the leg and underneath the fastener. A resistance heating element may be coiled around a portion of the leg. In this case, a temperature detecting element may be placed underneath the coil. Other examples of the energy transfer element include a polymeric heating element, an electrically conductive paint, or a printed flex circuit which are on a portion of the leg. Another variation employs the basket leg itself as either a RF electrode or a heated element. In such cases, the temperature sensing element may be attached directly to a basket leg by soldering, welding, adhesive bonding, or other means or member.

Another variation of the invention includes a sheath slidably coupled to and exterior to the expandable portion. The expandable portion may be resilient and self-expand into the second state when no longer confined by the sheath. For example, the sheath may be withdrawn in a proximal direction or the expandable portion may be advanced out of the sheath.

Yet another variation of the invention includes a deployment member comprising a handle adjacent to a proximal end of the elongated body. The elongated body may be slidably attached to the handle. The deployment member may also comprise a wire that extends from the handle through the lumen of the elongated body and is fixedly attached to the distal tip. This wire may also provide a current to the energy transfer members. The elongated body, the wire, and the distal tip may be slidably moveable in a distal and proximal direction. This variation of the deployment member may also include a stop configured to prevent distal movement of the wire beyond a deployment point. In this variation, beyond the deployment point, movement of the elongated body against the non-moving distal tip causes the expansion member to expand from a first state into a second expanded state.

Another variation of the invention includes a deployment member comprising a sheath that covers the elongated member and expandable portion and a handle at a proximal end of the sheath. The sheath may be slidably attached to the handle while the elongated member is rigidly attached to the handle. A wire may extend from said handle to a distal tip through a lumen of the elongated member. The variation may include a first control member attached to the sheath and slidably attached to the handle where proximal movement of the first control member causes the sheath to retract on the elongated member and uncover the expandable portion. This variation may also include a second control member which is attached to the wire where proximal movement of the second control member causes the distal tip and the expandable portion to retract against the non-moving elongated member and causes the expandable portion to radially expand into a second state.

Another variation of the invention includes a deployment member having force compensation or deflection limiting stops to prevent over-expansion of the expandable member when deployed within the body.

A variation of the invention includes placing a sheath exterior to the elongated body and expandable portion such that the expandable portion is placed within the sheath in a first unexpanded state. When the expandable portion is no longer restrained by the sheath, the expandable portion expands into its second state. The invention may also include a control member moveably secured to the handle where the member is configured to advance the elongated body and the wire in the distal and proximal directions. Another variation of the invention includes a detent means for maintaining the elongated body distally of the deployment point. The control member may also be configured to frictionally maintain the elongated body distally of the deployment point. In these cases, the expandable portion will be in the second expanded state. Other variations of the inventive device may include use of levers, control wheels, or screw mechanisms in place of a control member.

Another variation of the inventive device includes an atraumatic distal tip that may be configured to prevent gouging of the airway tissue. The distal tip may have a redundant joint to prevent separation of the tip from the apparatus. The distal tip may also be sized to fit within or through a bronchoscope.

Another variation of the invention includes a central wire extending from the distal tip to the proximal portion of the device. The wire may be configured to provide a current to the energy transfer elements. A temperature detecting element may also be attached to the wire.

The inventive device may also be radiopaque or may have radiopaque elements.

Another variation of the invention includes providing a steering member in the device to deflect the distal tip of the apparatus in a desired direction.

Another variation of the invention includes placing a vision system on the apparatus. The vision system may include a fiber-optic cable or a CCD chip.

Another variation of the invention includes providing a power supply configured to deliver energy through the energy transfer elements to the airway walls. The power supply may be configured to include a high temperature shut off or one which shuts down if a minimum temperature is not detected within a predetermined time or if a minimum temperature slope is not detected during a predetermined time.

The invention further includes a kit comprising an energy transfer apparatus for facilitating energy transfer into a mass of airway tissue and a generator configured to delivery energy to the energy transfer apparatus. The kit may further include a bronchoscope as may any of the other inventive variations.

The invention further includes an energy transfer apparatus for facilitating energy transfer into a mass of airway tissue within a lung, the energy transfer apparatus having been rendered sterile for the purposes of prevention of infection of the lung.

The present invention may be used for a treatment of asthma or other constriction or spasm of a bodily conduit by application of energy. The treatment reduces the ability or propensity of the airway to contract, reduces plugging of the airway, increases the inner airway diameter, and/or reduces resistance to flow through the airway.

The present invention relates to a method for treating bodily conduits by transfer of energy to or from the conduit walls to prevent the conduit from being able to constrict, to enlarge the conduit, or to reduce resistance to flow through the conduit. The invention is particularly directed to the treatment of the airways in the lungs to reduce the effects of asthma and other lung disease.

The present invention provides methods to decrease airway responsiveness and airway resistance to flow which may augment or replace current management techniques.

In accordance with a variation of the present invention, a method for treating conditions of the lungs by decreasing airway responsiveness includes energy use as energy is transferred to or from an airway wall to alter the airway wall in such a manner that the responsiveness of the airway is reduced.

In accordance with an additional variation of the present invention, the energy transferred to or from the airway wall alters the structure of the airway wall.

In accordance with a further variation of the present invention, the energy transferred to or from the airway wall alters the function of the airway wall.

In accordance with another variation of the present invention, a method for treating conditions of the lungs by decreasing airway resistance to airflow includes transferring energy to or from an airway wall to alter the airway wall in such a manner that a resistance to airflow of the airway is decreased.

The present invention provides advantages of a treatment for asthma or other constriction or spasm of a bodily conduit by application of energy. The treatment reduces the ability of the airway to contract, reduces plugging of the airway, and/or increases the inner airway diameter.

The present invention relates to methods for treating a lung, preferably having at least one symptom of reversible obstructive pulmonary disease, comprising the steps of advancing a treatment device into the lung and treating the lung with the device to at least reduce the ability of the lung to produce at least one symptom of reversible obstructive pulmonary disease and to decrease the resistance to the flow of air through the lung.

A variation of the invention includes the method described above further comprising the step of locating one or more treatment sites within an airway of the lung, selecting at least one of the treatment sites and treating at least one of the treatment sites selected in the selecting step. The invention may further include performing the steps while the lung is experiencing at least one symptom of either natural or artificially induced reversible obstructive pulmonary disease.

A further variation of the invention includes the method described above and further includes the steps of testing the lung for at least one pre-treatment pulmonary function value prior to the treating step, and re-testing the lung for at least one post-treatment pulmonary function value subsequent to the treating step.

A further variation of the invention includes the method described above further comprising identifying treatment sites within the airway being highly susceptible to either airway inflammation, airway constriction, excessive mucus secretion, or any other symptom of reversible obstructive pulmonary disease.

Another variation of the invention includes the method described above and the additional step of stimulating the lung to produce at least one artificially induced symptom of reversible obstructive pulmonary disease. The invention may further comprise the step of evaluating the results of the stimulating step.

Another variation of the invention includes the method described above where treating at least airway tissue within the lung further comprises the step of determining the effect of the treatment by visually observing the airway for blanching of airway tissue.

Another variation of the invention includes the method described above where treating at least airway tissue at a treatment site within the lung further comprises the step of monitoring electrical impedance of tissue at one or more points.

Another variation of the invention includes the method described above where treating the lung includes sub-mucosal treatment of at least airway tissue in the lung.

Another variation of the invention includes the method described above where the treating step includes treating the lung by depositing a radioactive substance in at least one treatment site within the lung.

Another variation of the invention include the method described above further including the step of scraping tissue from a wall of an airway within the lung prior to the treating step. The invention may further comprise depositing a substance on the scraped wall of the airway.

Another variation of the invention includes the method described above further comprising pre-treating the lung to at least reduce the ability of the lung to produce at least one symptom of reversible obstructive pulmonary disease prior to the treating step, where at least one parameter of the pre-treating step is lesser than at least one parameter of the treating step.

Another variation of the invention comprises the method described above where the treating step includes separating the treating step into stages to reduce the healing load on the lung. The separating step may comprise treating different regions of the lung at different times or dividing the number of treatment sites into a plurality of groups of treatment sites and treating each group at a different time.

Another variation of the invention includes the method described above further comprising sensing movement of the lung and repositioning the treatment device in response to said sensing step.

Another variation of the invention includes the method described above further comprising reducing the temperature of lung tissue adjacent to a treatment site.

Another variation of the invention includes the method described above further comprising the step of providing drug therapy, exercise therapy, respiratory therapy, and/or education on disease management techniques to further reduce the effects of reversible obstructive pulmonary disease.

The invention further includes the method for reversing a treatment to reduce the ability of the lung to produce at least one symptom of reversible obstructive pulmonary disease comprising the step of stimulating re-growth of smooth muscle tissue in the lung.

The invention further includes the method of evaluating an individual having reversible obstructive pulmonary disease as a candidate for a procedure to reduce the ability of the individual's lung to produce at least one reversible obstructive pulmonary disease symptom by treating an airway within the lung of the individual, the method comprising the steps of assessing the pulmonary condition of the individual, comparing the pulmonary condition to a corresponding predetermined state; and evaluating the individual based upon the comparing step. The method may additionally comprise the steps of performing pulmonary function tests on the individual to obtain at least one pulmonary function value, comparing the at least one pulmonary function value to a corresponding predetermined pulmonary function value, and evaluating the individual based upon the comparing step.

The invention further comprises a method of evaluating the effectiveness of a procedure to reduce the ability of lung to produce at least one symptom of reversible obstructive pulmonary disease previously performed on an individual having reversible obstructive pulmonary disease, the method comprising the steps of assessing the pulmonary condition of the individual, comparing the pulmonary condition to a corresponding predetermined state, and evaluating the effectiveness of the procedure based upon the comparing step. The method may additionally comprise the steps of performing pulmonary function tests on the individual to obtain at least one pulmonary function value, treating the lung to at least reduce the ability of the lung to produce at least one symptom of reversible obstructive pulmonary disease, performing post-procedure pulmonary function tests on the individual to obtain at least one post-procedure pulmonary function value; and comparing the pulmonary function value with the post-procedure pulmonary function value to determine the effect of the treating step.

BRIEF DESCRIPTION OF THE DRAWINGS

The invention will now be described in greater detail with reference to the various embodiments illustrated in the accompanying drawings:

FIGS. 6E-6O illustrate a proximal joint of the invention.

FIGS. 7A-7D illustrate a series and parallel wiring of legs of the basket.

FIGS. 5A-8C illustrate examples of variable thicknesses of legs of the basket.

DETAILED DESCRIPTION

Figure 1:
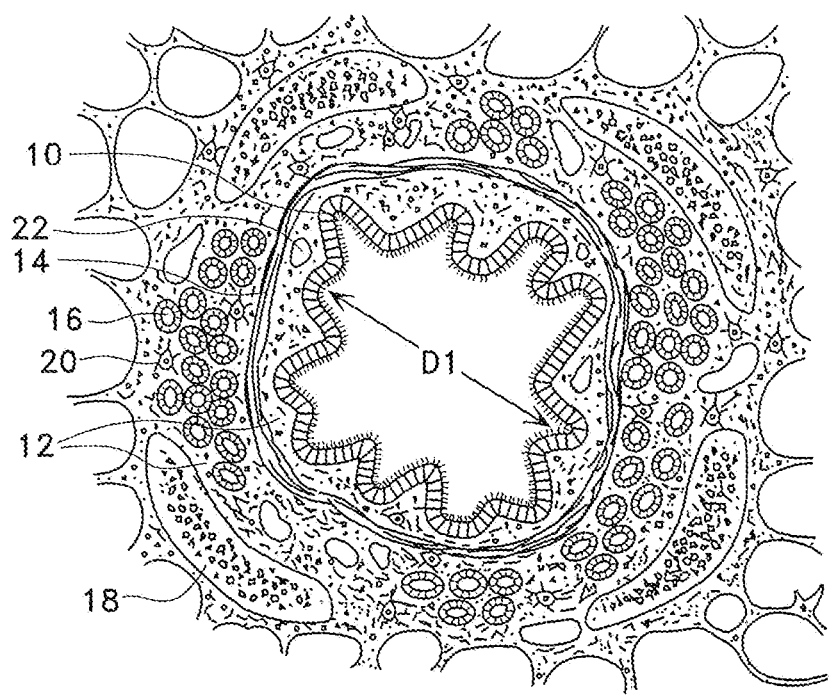
FIG. 1 is a cross sectional view of a medium sized bronchus in a healthy patient.

The invention relates to methods for improving airflow through the airways of a lung having reversible obstructive pulmonary disease. It is intended that the invention is applicable to any aspect of reversible obstructive pulmonary disease, including but not limited to asthma. One way of improving airflow is to decrease the resistance to airflow within the lungs. There are several approaches to reducing this resistance, including but not limited to reducing the ability of the airway to contract, increasing the airway diameter, reducing the inflammation of airway tissues, and/or reducing the amount of mucus plugging of the airway. The present invention includes advancing a treatment device into the lung and treating the lung and using energy to at least reduce the ability of the lung to produce at least one symptom of reversible obstructive pulmonary disease. The following is a brief discussion of some causes of increased resistance to airflow within the lungs and the inventive treatment of the invention described herein. As such, the following discussion is not intended to limit the aspects or objective of the inventive method as the inventive method may cause physiological changes not described below but such changes still contributing to reducing or eliminating at least one of the symptoms of reversible obstructive pulmonary disease.

Reducing the Ability of the Airway to Contract

The inventive energy treatment reduces the ability of the airways to narrow or to reduce in diameter due to airway smooth muscle contraction. This treatment reduces the ability of the smooth muscle to contract thereby lessening the severity of an asthma attack. The reduction in the ability of the smooth muscle to contract may be achieved by treating the smooth muscle itself or by treating other tissues which in turn influence smooth muscle contraction or the response of the airway to the smooth muscle contraction. Treatment may also reduce airway responsiveness or the tendency of the airway to narrow or to constrict in response to a stimulus.

The amount of smooth muscle surrounding the airway can be reduced by exposing the smooth muscle to energy which either kills the muscle cells or prevents these cells from replicating. The reduction in smooth muscle reduces the ability of the smooth muscle to contract and to narrow the airway during a spasm. The reduction in smooth muscle and surrounding tissue has the added potential benefit of increasing the caliber or diameter of the airways, this benefit reduces the resistance to airflow through the airways. In addition to the use of debulking smooth muscle tissue to open up the airways, the device used in the present invention may also eliminate smooth muscle altogether by damaging or destroying the muscle. The elimination of the smooth muscle prevents the contraction or spasms of hyper-reactive airways of a patient having reversible obstructive pulmonary disease. By doing so, the elimination of the smooth muscle may reduce some symptoms of reversible obstructive pulmonary disease.

The ability of the airway to contract can also be altered by treatment of the smooth muscle in particular patterns. The smooth muscle is arranged around the airways in a generally helical pattern with pitch angles ranging from about −38 to about +38 degrees. Thus, the treatment of the smooth muscle in appropriate patterns interrupts or cuts through the helical pattern of the smooth muscle at a proper pitch and prevents the airway from constricting. This procedure of patterned treatment application eliminates contraction of the airways without completely eradicating smooth muscle and other airway tissue. A pattern for treatment may be chosen from a variety of patterns including longitudinal or axial stripes, circumferential bands, helical stripes, and the like as well as spot patterns having rectangular, elliptical, circular or other shapes. The size, number, and spacing of the treatment bands, stripes, or spots are chosen to provide a desired clinical effect of reduced airway responsiveness while limiting insult to the airway to a clinically acceptable level.

The patterned treatment of the tissues surrounding the airways with energy provides various advantages. The careful selection of the portion of the airway to be treated allows desired results to be achieved while reducing the total healing load. Patterned treatment can also achieve desired results with decreased morbidity, preservation of epithelium, and preservation of a continuous or near continuous ciliated inner surface of the airway for mucociliary clearance. The pattern of treatment may also be chosen to achieve desired results while limiting total treatment area and/or the number of airways treated, thereby improving speed and ease of treatment.

Application of energy to the tissue surrounding the airways may also cause the DNA of the cells to become cross linked. The treated cells with cross linked DNA are incapable of replicating. Accordingly, over time, as the smooth muscle cells die, the total thickness of smooth muscle decreases because of the inability of the cells to replicate. The programmed cell death causing a reduction in the volume of tissue is called apoptosis. This treatment does not cause an immediate effect but causes shrinking of the smooth muscle and opening of the airway over time and substantially prevents re-growth. The application of energy to the walls of the airway may also be used to cause a cross linking of the DNA of the mucus gland cells thereby preventing them from replicating and reducing excess mucus plugging or production over time.

The ability of the airways to contract may also be reduced by altering mechanical properties of the airway wall, such as by increasing stiffness of the wall or by increasing parenchymal tethering of the airway wall. Both of these methods increase the strength of the airway wall and further oppose contraction and narrowing of the airway.

There are several ways to increase the stiffness of the airway wall. One way to increase stiffness is to induce fibrosis or a wound healing response by causing trauma to the airway wall by delivery of therapeutic energy to the tissue in the airway wall. The energy is preferably delivered in such a way that it minimizes or limits the intra-luminal thickening that may occur.

Another way to increase the effective stiffness of the airway wall is to alter the submucosal folding of the airway upon narrowing. The mucosal layer includes the epithelium, its basement membrane, and the lamina propria, a subepithelial collagen layer. The submucosal layer may also play a role in airway folding. As an airway narrows, its perimeter remains relatively constant, with the mucosal layer folding upon itself. As the airway narrows further, the mucosal folds mechanically interfere with each other, effectively stiffening the airway. In asthmatic patients, the number of folds is fewer and the size of the folds is larger, and thus, the airway is free to narrow with less mechanical interference of mucosal folds than in a healthy patient. Thus, asthmatic patients have a decrease in airway stiffness and the airways have less resistance to narrowing.

The mucosal folding in asthmatic patients can be improved by treatment of the airway in a manner which encourages folding. Preferably, a treatment will increase the number of folds and/or decrease the size of the folds in the mucosal layer. For example, treatment of the airway wall in a pattern such as longitudinal stripes can encourage greater number of smaller mucosal folds and increase airway stiffness.

The mucosal folding can also be increased by encouraging a greater number of smaller folds by reducing the thickness of the mucosa and/or submucosal layer. The decreased thickness of the mucosa or submucosa may be achieved by application of energy which either reduces the number of cells in the mucosa or submucosal layer or which prevents replication of the cells in the mucosa or submucosal layer. A thinner mucosa or submucosal layer will have an increased tendency to fold and increased mechanical stiffening caused by the folds.

Another way to reduce the ability of the airways to contract is to improve parenchymal tethering. The parenchyma surrounds airways and includes the alveolus and tissue connected to and surrounding the outer portion of the airway wall. The parenchyma includes the alveolus and tissue connected to and surrounding the cartilage that supports the larger airways. In a healthy patient, the parenchyma provides a tissue network which connects to and helps to support the airway. Edema or accumulation of fluid in lung tissue in patients with asthma or COPD is believed to decouple the airway from the parenchyma reducing the restraining force of the parenchyma which opposes airway constriction. Energy can be used to treat the parenchyma to reduce edema and/or improve parenchymal tethering.

In addition, the applied energy may be used to improve connection between the airway smooth muscle and submucosal layer to the surrounding cartilage, and to encourage wound healing, collagen deposition, and/or fibrosis in the tissue surrounding the airway to help support the airway and prevent airway contraction.

Increasing the Airway Diameter

Hypertrophy of smooth muscle, chronic inflammation of airway tissues, and general thickening of all parts of the airway wall can reduce the airway diameter in patients with reversible obstructive pulmonary disease. Increasing the overall airway diameter using a variety of techniques can improve the passage of air through the airways. Application of energy to the airway smooth muscle of an asthmatic patient can debulk or reduce the volume of smooth muscle. This reduced volume of smooth muscle increases the airway diameter for improved air exchange.

Reducing inflammation and edema of the tissue surrounding the airway can also increase the diameter of an airway. Inflammation and edema (accumulation of fluid) of the airway are chronic features of asthma. The inflammation and edema can be reduced by application of energy to stimulate wound healing and regenerate normal tissue. Healing of the epithelium or sections of the epithelium experiencing ongoing denudation and renewal allows regeneration of healthy epithelium with less associated airway inflammation. The less inflamed airway has an increased airway diameter both at a resting state and in constriction. The wound healing can also deposit collagen which improves parenchymal tethering.

Inflammatory mediators released by tissue in the airway wall may serve as a stimulus for airway smooth muscle contraction. Therapy that reduces the production and release of inflammatory mediator can reduce smooth muscle contraction, inflammation of the airways, and edema. Examples of inflammatory mediators are cytokines, chemokines, and histamine. The tissues which produce and release inflammatory mediators include airway smooth muscle, epithelium, and mast cells. Treatment of these structures with energy can reduce the ability of the airway structures to produce or release inflammatory mediators. The reduction in released inflammatory mediators will reduce chronic inflammation, thereby increasing the airway inner diameter, and may also reduce hyper-responsiveness of the airway smooth muscle.

A further process for increasing the airway diameter is by denervation. A resting tone of smooth muscle is nerve regulated by release of catecholamines. Thus, by damaging or eliminating nerve tissue in the airways the resting tone of the smooth muscle is reduced, and the airway diameter is increased. Resting tone may also be reduced by directly affecting the ability of smooth muscle tissue to contract.

Reducing Plugging of the Airway

Excess mucus production and mucus plugging are common problems during both acute asthma exacerbation and in chronic asthma management. Excess mucus in the airways increases the resistance to airflow through the airways by physically blocking all or part of the airway. Excess mucus may also contribute to increased numbers of leukocytes found in airways of asthmatic patients by trapping leukocytes. Thus, excess mucus can increase chronic inflammation of the airways.

One type of asthma therapy involves treatment of the airways with energy to target and reduce the amount of mucus producing cells and glands and to reduce the effectiveness of the remaining mucus producing cells and glands. The treatment can eliminate all or a portion of the mucus producing cells and glands, can prevent the cells from replicating or can inhibit their ability to secrete mucus. This treatment will have both chronic benefits in increasing airflow through the airways and will lessen the severity of acute exacerbation of the symptoms of reversible obstructive pulmonary disease.

Application of Treatment

The following illustrations are examples of the invention described herein. It is contemplated that combinations of aspects of specific embodiments or combinations of the specific embodiments themselves are within the scope of this disclosure. Likewise, it is intended that the devices described herein may be used to perform the various methods also described herein.

Figure 2:
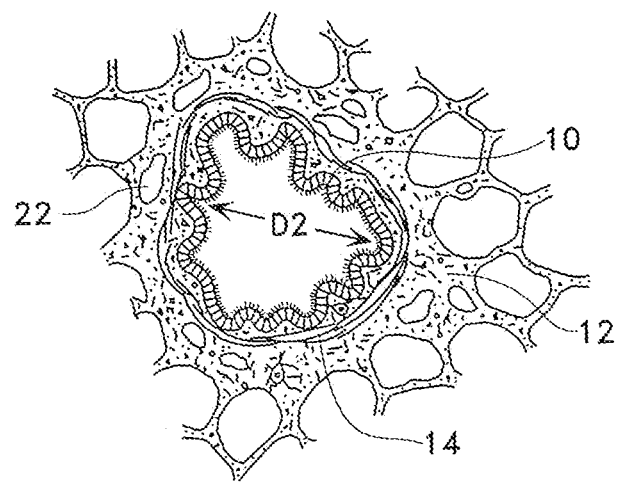
FIG. 2 is a cross sectional view of a bronchiole in a healthy patient.

FIGS. 1 and 2 illustrate cross sections of two different airways in a healthy patient. The airway of FIG. 1 is a medium sized bronchus having an airway diameter D1 of about 3 mm. FIG. 2 shows a section through a bronchiole having an airway diameter D2 of about 1.5 mm. Each airway includes a folded inner surface or epithelium 10 surrounded by stroma 12 and smooth muscle tissue 14. The larger airways including the bronchus shown in FIG. 1 also have mucous glands 16 and cartilage 18 surrounding the smooth muscle tissue 14. Nerve fibers 20 and blood vessels 24 also surround the airway.

Figure 3:
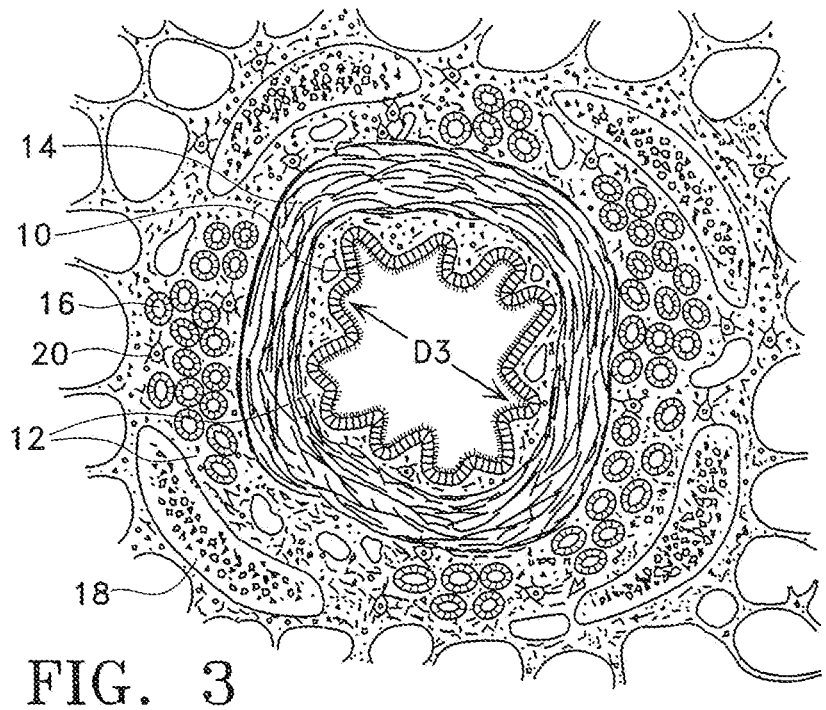
FIG. 3 is a cross sectional view of the bronchus of FIG. 1 showing the remodeling and constriction occurring in an asthma patient.

FIG. 3 illustrates the bronchus of FIG. 1 in which the smooth muscle 14 has hypertrophied and increased in thickness causing the airway diameter to be reduced from the diameter D1 to a diameter D3.

Figure 4:
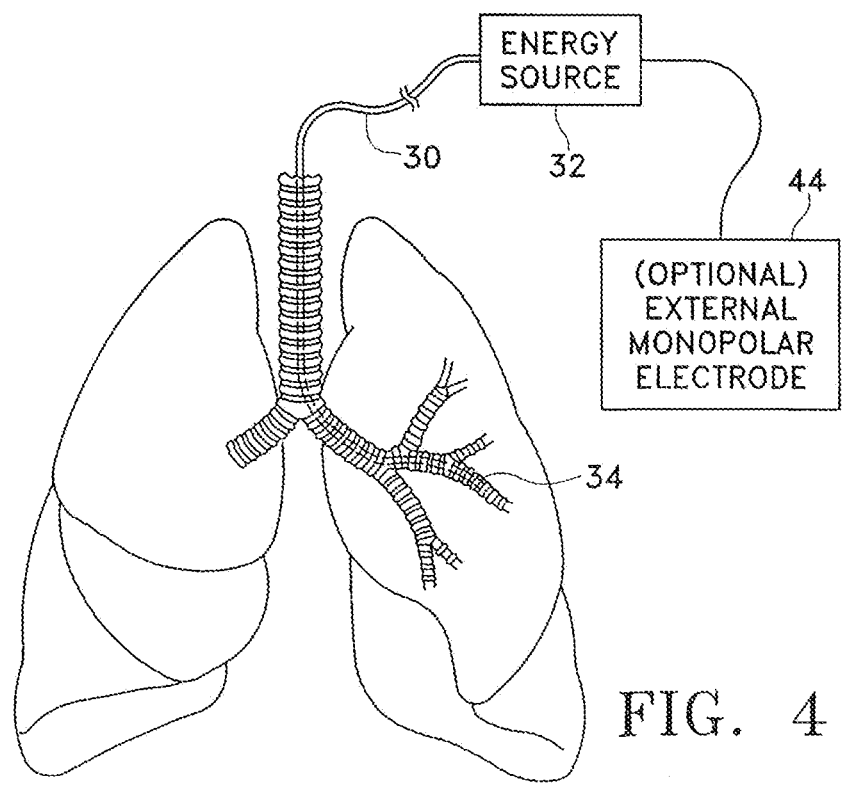
FIG. 4 is an illustration of the lungs being treated with a device according to the present invention.

FIG. 4 is a schematic side view of the lungs being treated with a treatment device 38 according to the present invention. The treatment device 38 may be an elongated member for treating tissue at a treatment site 34 within a lung. Although the invention discusses treatment of tissue at the surface it is also intended that the invention include treatment below an epithelial layer of the lung tissue.

Examples of Decreasing Resistance to Airflow

A device 30 of the present invention must be of a size to access the bronchus or bronchioles of the human lung. The device may be sized to fit within bronchoscopes, preferably, with bronchoscopes having a working channel of 2 mm or less. Also, the device should be of sufficient stiffness to fit and operate through the seal covering the working channel a bronchoscope.

The energy may be delivered by the treatment device 30 in a variety of treatment patterns to achieve a desired response. Examples of patterns are discussed in further detail below. Also, the device may, but is not necessarily, configured to deliver energy in non-intersecting strip patterns which are parallel with a central axis of an airway. For example, other variations of the device may be configured to deliver energy in a torsional pattern, or in a circumferential pattern around a wall of the airway. Such configurations which may be determined to deliver energy to the airway tissue that maximize the ability of the airway to permit airflow are considered to be within the scope of this invention.

The inventive devices include tissue contacting electrodes configured to be placed within the airway. These devices can be used for delivering radio frequency in either a monopolar or a bipolar manner or for delivering other energy to the tissue, such as conducted heat energy from resistively heated elements. As shown in FIG. 4, for monopolar energy delivery, one or more electrodes of the treatment device are connected to a single pole of the energy source 32 and an optional external electrode g is connected to an opposite pole of the energy source. For bipolar energy delivery, multiple electrodes are connected to opposite poles of the energy source 32 and the external electrode 44 is omitted. Naturally, the external electrode 44 depicted in FIG. 4, is not required in the case of bipolar energy delivery. The number and arrangement of the electrodes may vary depending on the pattern of energy delivery desired. The treatment devices of FIGS. 5A-10, and 12-20 are used to deliver radiant or heat energy to the airway. The treatment device of FIG. 11 may also be used to deliver indirect radio frequency, microwave energy, or conductive heat energy to the tissue. In cases of heat energy generated by resistive heating, the current may be AC or DC current or in the case of AC, the current may be delivered in the RF range. The use of RF provides an added safety feature of minimizing the possibility of harm to the patient caused by escaped current. The device may also use a combination of any of the energy transferring element configurations described herein.

The following illustrations are examples of the invention described herein. It is contemplated that combinations of aspects of specific embodiments or combinations of the specific embodiments themselves are within the scope of this disclosure.

Figure 5A:
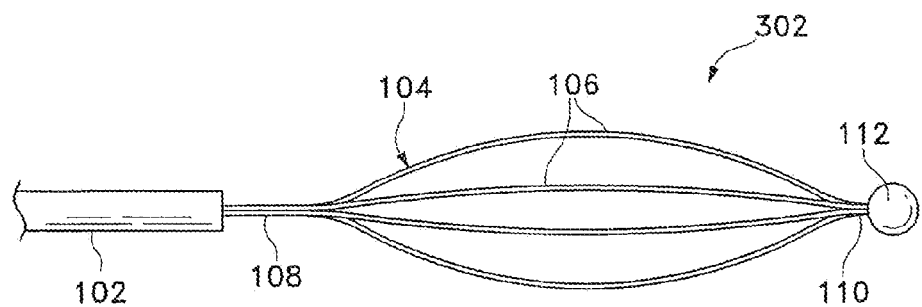
FIG. 5A is a partial side view of a variation of the inventive device having a plurality of wire shaped electrodes.

The treatment device 302 of FIG. 5A includes an elongated member 102 for delivering an expandable member 104 to a treatment site. The expandable member 104 may have a plurality of energy transfer elements (not illustrated) which are placed on a plurality of basket legs 106 to transfer energy at the treatment site. In this variation, the expandable member comprises a basket 104 which is defined by a number of basket legs 106. The basket legs 106 are formed from a plurality of elements which are soldered or otherwise connected together at two connection areas, a proximal joint 108 and a distal joint 110.

A desirable length of the basket 104, or the expandable portion of any variation of the invention, depends upon numerous factors. One consideration in determining a desired length of the expandable member, e.g., the distance between the joints of the basket, of the inventive device is related to the dimension of the target area or treatment region. For instance, some other factors include considerations of minimizing the amount of the expandable portion which is distal to the treatment region for optimized access, minimizing the amount of the expandable portion that is proximal to the treatment region for visualization and access concerns, and setting a desirable length of the expandable portion that will contact a sufficient portion of the treatment region during each application of the device. A compromise of such factors along with other considerations provides a desirable length for the expandable portion of the device. Preferably, the distance between the distal and proximal joints of the basket is less than 35 mm when the basket is in a first unexpanded state.

The legs 106 may be selected from a material that allows the basket to expand without plastic deformation. For example, the legs may comprise a stainless steel, or a shape memory/superelastic alloy such as a nitinol material. The basket legs 106 may have a rectangular cross section in those variations where the legs 106 are formed from ribbons, or the legs 106 may have a circular cross section in those variations where the legs are formed from wires. As discussed below, the legs 106 may also have other cross section as desired. It is also contemplated that the legs 106 need not all have similar cross sections. For instance, the cross section of each of the legs 106 in a basket 104 may be individually chosen to optimize such factors as the resilience of the basket 104, or to optimize energy transfer characteristics. The legs may also have a variable cross section along the length of the basket.

Illustrated are variations of the inventive device 302 having a basket 104 comprising of four legs 106. It is preferred that the legs 106 are spaced at equal intervals around the expandable member or basket 104. For example, in variations of the invention having four legs 106, the legs 106 are preferably, but not necessarily spaced at approximately 90 degree intervals around the basket 104. In variations having five legs 106, the legs 106 may be spaced at approximately 72 degree intervals. Other variations of the invention include devices having less than four legs or more than five legs. It is thought that the most effective number of legs is a compromise based on the size of the target airway, contact surface between the leg 106 and airway wall, and the maximum outer diameter of the elongated member 102.

The proximal 108 and/or distal 110 joints may also contain adhesive to bind the legs 106. The basket legs 106 between the proximal 108 and distal joint 110 are formed into the basket shape 104 so that arch shaped portions of the basket legs 106 will contact the walls of an airway to facilitate energy transfer. Although the figures illustrate the basket legs 106 as having a semi-circular or arc shape the device is not limited to such shapes. For example, the legs 106 may have a more oblong shape or sharper bends to allow for a more parallel leg surface area that contacts the target tissue. Each leg 106 may have a center that is substantially parallel to the elongated body so that there is sufficient contact between the airway walls and the parallel portion of the leg 106. The center that is substantially parallel is usually referred to as the energy delivery or active region of the leg 106.

The length of the basket 104 between the proximal and distal 110 joints may be less than 35 mm when the basket 104 is in a first unexpanded state. The legs 106 may be coated with an insulating material (not shown) except at the tissue contact points. Alternatively, the legs 106 of the basket 104 may be exposed while the proximal 108 and distal joint 110 are insulated. In this variation, the basket 104 is formed of a resilient material which allows the distal end of the inventive device 302 to be confined by a sheath (not shown) for delivery of the device 302 to the treatment site and allows the basket 104 to return to its original basket shape upon deployment. In other words, a variation of the invention is that the basket self-expands from a first state to a second expanded state upon the removal of any constraining or restrictive member such as a sheath (not shown). The inventive device 302 is preferably configured such that the basket legs 106 have sufficient resilience to come into contact with the airway walls for treatment.

FIG. 5A further illustrates a variation of the inventive device 302 in which a distal end of the device 302 is provided with a distal tip 112 that can have a radius to facilitate insertion of the device 302 into the lungs and also to minimize the possibility of causing trauma to surrounding tissue. The tip 112 is preferably sized to prevent the gouging of airway by the sheath. The design of the distal tip is selected to be atraumatic. The size of the tip may be selected to be large enough to prevent the sheath from gouging airways yet small enough to pass in and out of a bronchoscope.

Figure 5B:
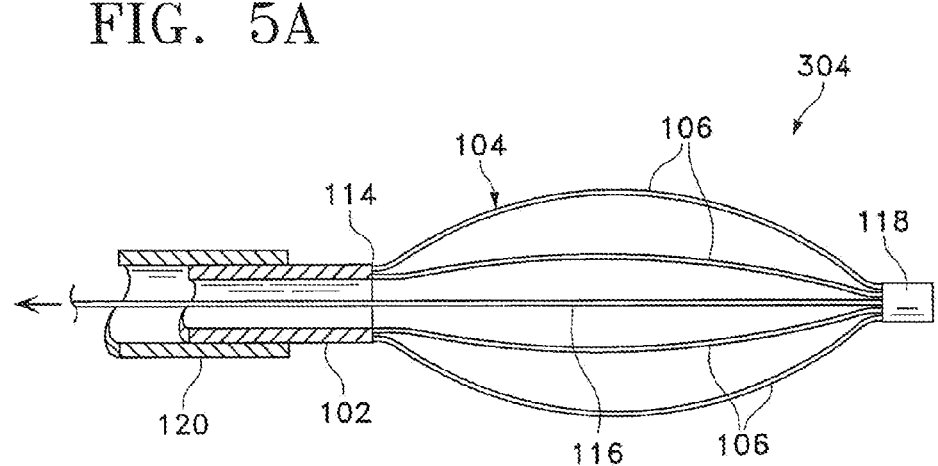
FIG. 5B is a cross sectional side view of another variation of a device having a plurality of wire shaped electrodes with a deployment wire attached to a distal tip of the device.

FIG. 5B illustrates a variation of the inventive device 302 having basket legs 108 connected to a distal end 114 of the elongated member 102 and forming a basket 104. In this variation, a proximal joint is found at the distal end 114 of the elongated member 102. The basket 104 is expanded radially, to its second state, during use to ensure contact between the energy transfer elements (not shown) and the airway walls (not shown) by, for example, pulling on a center pull wire 116 which is connected to a distal tip 118 of the expandable portion 104. The center pull wire 116 may extend through a lumen of the elongated member 102 towards a proximal portion (not shown) of the elongated member 102. It is also contemplated that the center pull wire 116 may be configured to deliver current to the energy transfer elements found on the expandable member 104. The inventive device 302 may be delivered to a treatment site through a delivery sheath 120 and may be drawn along or moved axially along the airway to treat the airway in a pattern of longitudinal or helical stripes.

As noted above, the basket 104 may be resilient or self-expanding (e.g., see FIG. 5A) to expand to a second expanded state or the basket 104 may require an expanding force (e.g., see FIG. 5B). An example of this variation of the inventive device 304 is shown in FIG. 5B. In this variation, the basket 104 may be resilient and the sheath 120 may comprise the deployment member. In this variation, when the elongate body 102 and basket 104 are withdrawn into the sheath 120, the basket 104 contracts within the sheath 120 and assumes a first state. Hereinafter, elongate member, elongated member, elongate body, and elongated body are used interchangeably. In one variation of the invention, upon advancing the basket 104 and elongate body 102 out of the sheath 120, the basket 104 may resiliently assume a second expanded state. In another variation of the invention, the basket 104 may assume a second expanded state with the aid of a wire 116. This wire may also be configured to deliver power to the energy exchange elements 106.

Figure 5C:
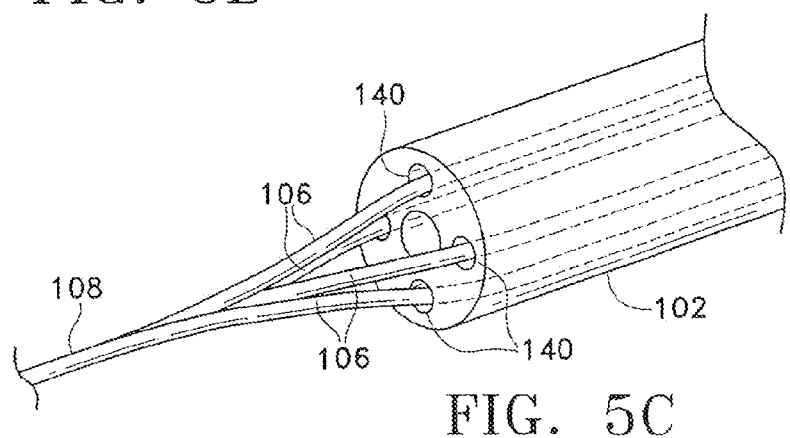
FIG. 5C shows a partial view of a variation of an elongated member of inventive device having a plurality of lumens for nesting the legs of the basket.

FIG. 5C illustrates another variation of the inventive device where an elongated member 102 is configured to have a plurality of lumens 140 so that each of the basket legs 106 are isolated within the lumens 140 of the elongated member 102 until the legs 106 exit the elongated member 102 and connect at a proximal joint 108. The invention may have basket legs 106 selected with a sufficient length such that the ends of each of the legs 106 extend substantially into the lumens 140. As a result of being inserted deeply within the lumen, the ends of the legs 106 would require significant travel before they exited the lumen 140. Preferably, the basket leg is at least twice the length of the basket. This feature provides added safety as it minimizes the risk of the basket legs 106 dislodging from the elongate member 102 even if one of the basket legs sticks to tissue within the lumen.

While extending the legs 106 a substantial distance into the lumens 140 minimizes the risk of the legs becoming dislodged, extending the legs into the lumens also structurally reinforces the lumens, thereby decreasing the flexibility of the distal portion of the elongate member. Consequently, it may be desirable to vary the distance each leg 106 is inserted into the lumens 140 by varying the length of each leg. For example, where maximum flexibility is desired, the distance each leg is inserted into the lumens 140 should be as short as possible such that little or no reinforcement is provided to the elongate member. Where increased stiffness is desired, all of the legs 106 preferably extend a substantial distance into the lumens 140. Where intermediate flexibility is desired, or where a smooth transition is desired between two regions having a different flexibility, a combination of long and short legs can be employed. A smooth transition prevents kinking of the shaft upon bending. Further, the ends of one or more of the legs may be notched, slotted, hinged, or include other patterns which can affect the flexibility of the legs, thereby affecting the flexibility of the elongate member 102.

In another variation of the invention, the elongated member 102 may comprise concentric tubes (not shown) rather than multi-lumen tubes where basket legs are inserted in the annulus between the tubes. It is also contemplated that an elongated member may be reinforced with the use of a reinforcing member. Such a reinforcing member may include a coiled wire or polymeric insert.

Figure 5D:
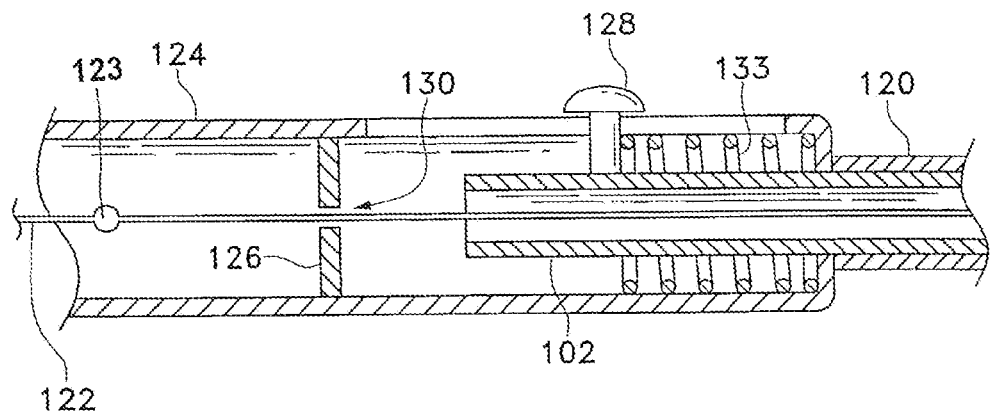
FIGS. 5D-5I illustrate a variation of the invention and a deployment member for deploying the device.
Figure 5E:
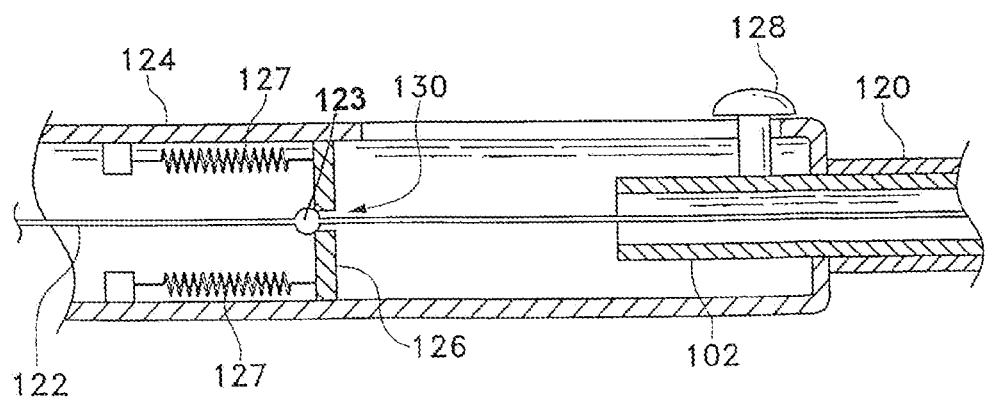
Figure 5F:
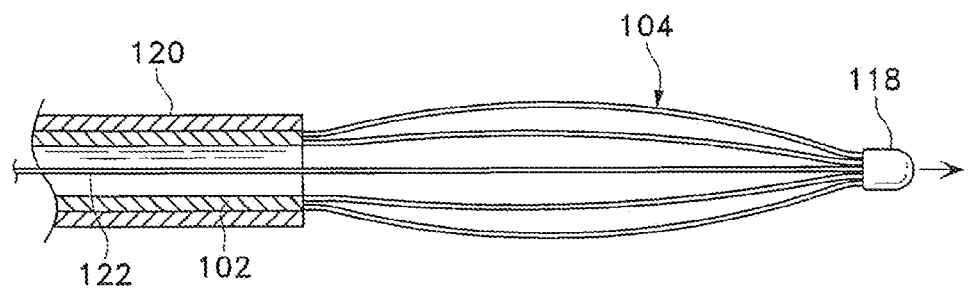
Figure 5G:
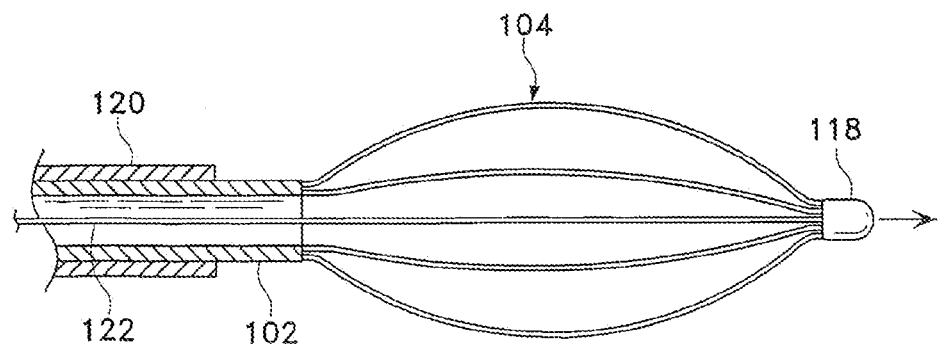

FIG. 5D-5I illustrate variations of the inventive device that use an expanding force to expand the basket. FIG. 5D illustrates a deployment member of the device. FIG. 5E illustrates the device of FIG. 5D when the elongated member is moved in a distal direction to a deployment point. FIG. 5F-5G illustrates the elongated member 102, sheath 120, expandable member 104, distal tip 118, and wire 122 extending through the device. FIG. 5F illustrates the basket 104 in a first unexpanded state when the elongated member 102 and wire 122 are proximal of the deployment point 130. FIG. 5G illustrates the expansion of the basket 104 to a second expanded state as the elongated member 102 moves distally and the wire 122 is restrained at the deployment point 130.

Turning now to FIG. 5D, the deployment member may comprise a handle 124 which is adjacent to a proximal portion of an elongated member 102. The handle may be designed to be operated by a single hand, either right or left. The handle may also have a control switch for operation of the device. Such a switch could control the power supply attached to the device as well. Also, the handle may be configured to determine the position of the device within a human body as the device is advanced to a target site. For example, marks or indicia on the handle or even a readout could provide information to the user as to the relative deployment state of the expandable member. Also, a sensor may be placed on the handle 124, this sensor may be used to determine the position of the expandable member. Such a sensor could also be used to measure the size of the airway, such a measurement could be used as a control variable to determine the amount of energy that the device power supply must deliver. The handle 124 may control the expandable member using force compensation (e.g., a spring, etc.) or deflection limiting stops to control the expansion of the expandable member. Such force compensation or deflection stops provide a limit to the expansion member to avoid over-expansion of a particular airway.

Turning now to the handle 124 of FIG. 5D, an elongated member 102 may be slidably mounted to the handle. The variation of the invention depicted in these Figures may also, but does not necessarily, include a sheath 120 exterior to the elongated body 102.

A wire 122 extends from the handle through the elongated member 102 and may be attached to a distal tip 118 of the device. The wire 122, elongated member 102, and distal tip (not shown) are slidably moveable in both a distal and proximal directions. The handle may also include a stop 126 which prevents the wire 122 from moving distally beyond a deployment point 130.

Wire 122 may also include an obstruct 123. Obstruct 123 prevents wire 122 from moving through stop 126, thereby limiting movement of the distal end of the basket when the elongate member is urged forward, thus expanding the basket. While obstruct is shown in FIG. 5D having a spherical shape such as a welded ball of metal, obstruct can be a variety of materials and shapes such as a metal or plastic sleeve crimped to wire 122. The crimp may be formed into, for example, a sawtooth or serpentine shape, by indenting the sleeve around its perimeter. Alternatively, the sleeve may be crimped axisymmetrically. Axisymmetric shapes include, for example, cylindrical, hexagonal, or octagonal shapes. Wire 122 may also be looped around obstruct 123 to further prevent the obstruct from becoming detached from the wire. The obstruct 123 may also be formed integral with the pull wire 122. For example, the pull wire may be crimped into a sawtooth configuration to form an obstruct. While a saw-tooth pattern is described, the invention is not so limited. Any of a number of patterns may form a suitable obstruct 123 with the stop 126. Examples include loops, knots, hooks, squares, etc. Examples of suitable methods for forming the wire include pressing or crimping the wire into a stable obstruct configuration.

The stop 126 may be connected to a spring (not shown) to limit the expansion of the expandable member upon reaching a pre-determined force. The handle may also include a stiffener 133 to support the elongated member 102 within the handle. The stiffener 133, for example, prevents the elongated member from buckling within the handle 124. Examples of suitable stiffeners include metal and plastic springs and rigid tubes of metal or plastic.

The handle 124 may include a control member 128 that is moveably attached to the handle 124 for moving the elongated member 102 in a distal/proximal direction. In addition, the handle may include a control switch for activating the electrodes when the control member is moved beyond a trigger point. Thus, energy would be delivered once the basket reached a certain size.

Although the handle 124 in the figures is depicted to have a control member 128 as illustrated, other variations of control members are also contemplated to be within the scope of this invention. For example, though not illustrated, a handle 124 may include other configurations, such as lever, thumbwheel, screw-mechanism, ratchet mechanism, etc., which are attached to the handle 124 to provide control actuation for the expandable member.

FIG. 5E illustrates a variation of the inventive device when the elongated member 102 and wire 122 are moved in a distal direction. In this illustrations, a stop 126 prevents the wire 122 from moving distally of a deployment position 130. This illustration further illustrates a variation of the invention where the stop 126 is attached to springs 127 which provide force compensation for the expandable member on the device. Although not shown, a control member 128 may have a stop which limits its travel along a handle 124. Such a stop is an example of a deflection limiting mechanism which controls the movement of the control member 128, thus controlling the extent of the expansion of the expandable member. The stiffener 133 may also provide force compensation to limit expansion of the basket beyond a predetermined size.

FIG. 5F illustrates the invention when the expandable member or basket 104 is in a first unexpanded state. As noted above, the wire 122 is attached to a distal tip 118 of the device and both are prevented from distal movement when the wire 122 is in the deployment position 130. Therefore, as depicted in FIG. 5G, movement of the elongated member 102 in a distal direction against a distal tip 118, that is restrained by a wire 122, causes a basket 104 to compress between the advancing elongated member 102 and the stationary distal end 118. Thus, the basket 104 is forced outward and radially expands into a second expanded state. As noted above, the wire 122 may also be used to transfer energy to or from the energy transfer elements found on the basket 104. Also, it is contemplated that the wire 122 may be a wire, a ribbon, a tube, or of any other equivalent structure. Also contemplated, but not shown, is a detent means for maintaining the elongated member in a distal position to expand the basket 104 against the distal tip 118 without the need for continual applied force by a user of the device. Also contemplated is a ratchet member, or friction member to maintain the basket 104 in the expanded state.

Figure 5H:
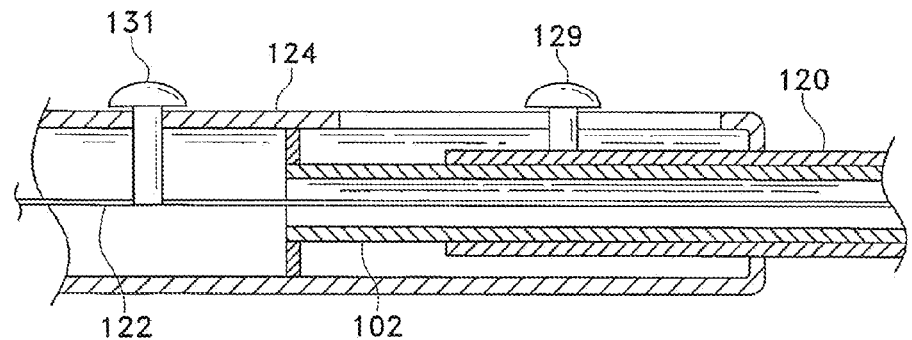
Figure 5I:
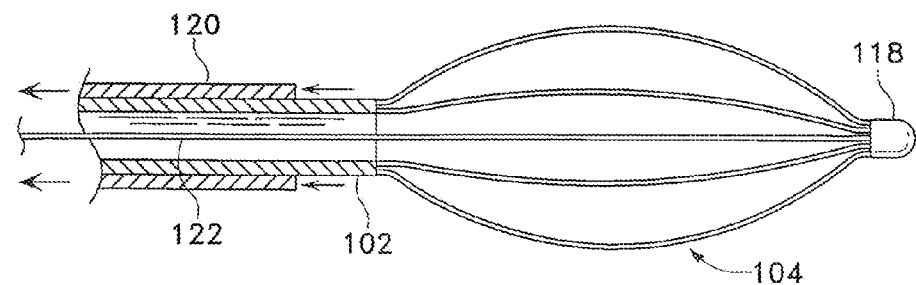

FIG. 5H illustrates another variation of a deployment member. In this variation, a sheath 120 may be slidably attached to a handle 124. In this variation, the elongate member 102 is rigidly attached to the handle 124. The sheath 120 may be attached to a first control member 129. A wire 122 extends through the elongate member 102 and is attached to the distal tip of the device (not shown). The wire 122 may be attached to a second control member 131. As indicated in FIG. 5I, proximal movement of the first control member 129 causes the sheath 120 to proximally retract over the elongate member 102 and uncover the expandable portion (not shown). Proximal movement of the second control member 131 causes the wire 122, distal joint, and expandable member to move against the non-moving elongate member 102 which causes the expandable member to expand into a second state.

Figure 5J:
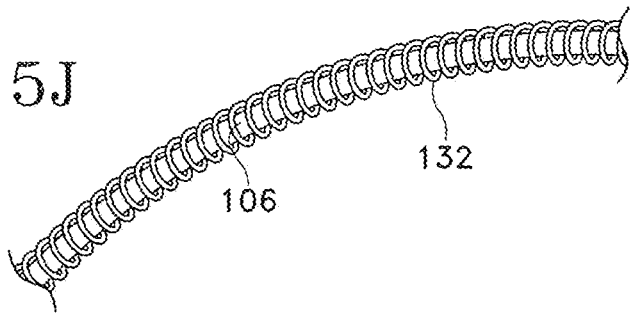
FIGS. 5J-5L illustrate examples of energy transfer elements of the device.
Figure 5K:
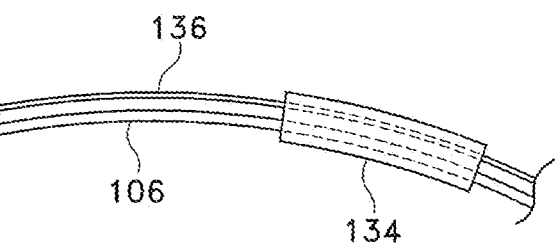
Figure 5L:
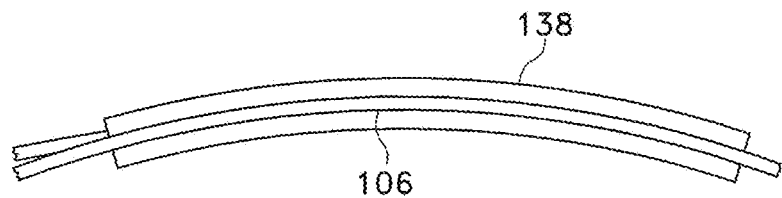

Turning now to the energy transfer elements located on the expandable portion, FIG. 5J-5L illustrate examples of energy transfer elements that may be located on the expandable portion of the device. In the variation of the invention where the expandable portion comprises a basket having basket legs 106, the basket legs 106 may function as heat exchange elements. In other words, the device may be configured so that the leg is an electrode or the conductive heating element. In these variations, the leg 106 may be partially covered with an insulation only leaving an active region exposed for delivery of energy to the airways. Examples of such insulation include a heat shrink sleeve, a dielectric polymeric coating, or other material which may function as an insulator.

FIG. 5J illustrates an example of a basket leg 106 with an energy transferring element 132 coiled around the leg 106. In this example, the energy transferring element uses conductive heating and comprises a resistance heating element 132 coiled around the leg 106. FIG. 5K illustrates a variation of the invention having an RF electrode attached to the basket leg 106. The RF electrode may be attached to the basket leg 106 via the use of a fastener 134. For example, the electrode may be attached via the use of a heat shrink fastener 134, (e.g., polymeric material such as PET or polyethylene tubing).

FIG. 5L illustrates another variation of the invention where the energy transfer element is a printed circuit 138 that is situated around the leg 106 and secured to the leg. Also contemplated, but not shown for use as energy transfer elements are a polymeric heating material, an electrically conductive paint, a resistance element sputtered onto the leg in a pattern or formed on a substrate by photofabrication. Also, the basket leg itself may be chosen of appropriate size and resistivity to alloy dual use as a basket and energy transfer element. Many nickel-chromium alloys have both high specific resistance and significant spring-like properties. In any variation of the invention the use of adhesives or other coatings may also be used to secure the energy transfer element to the basket leg 106. Also, the energy transfer elements are not limited to what is illustrated in the drawings. It is also contemplated that other types of energy transfer elements may be used such as radiant, laser, microwave, and heat energy.

Figure 6A:
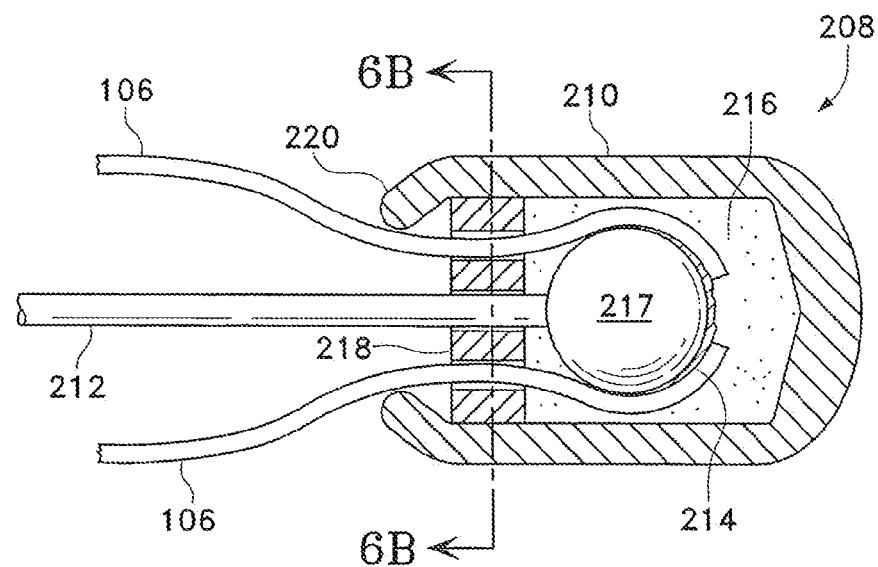
FIGS. 6A-6D illustrate distal joints of the invention.
Figure 6B:
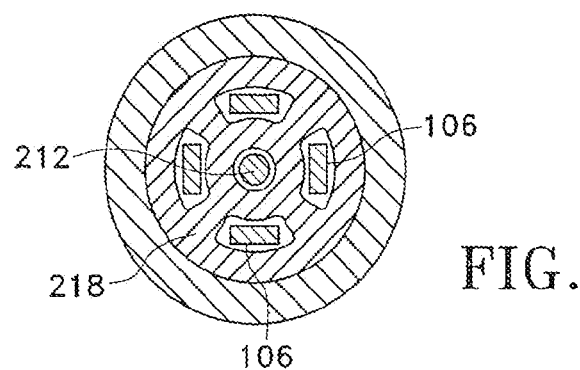

FIG. 6A illustrates a variation of a distal tip 210 having a redundant joint. The distal tip 208 has a polymeric cap 210 covering the distal ends of the basket legs 106 and wire 212. The legs 106 are soldered 214 to the distal end of the wire 212. Also used to maintain the joint is an adhesive 216 substantially filling the polymeric cap 210. A multi-lumen piece 218 separates the legs 106 and wire 212. A side view of the multi-lumen piece 218 is shown in FIG. 6B. A multi-lumen tubing may be used for the multi-lumen piece 218. The ends 220 of the polymeric cap 210 may be heat formed or otherwise tapered down around the legs 106. Although not illustrated, the proximal joint may also be redundant.

Figure 6C:
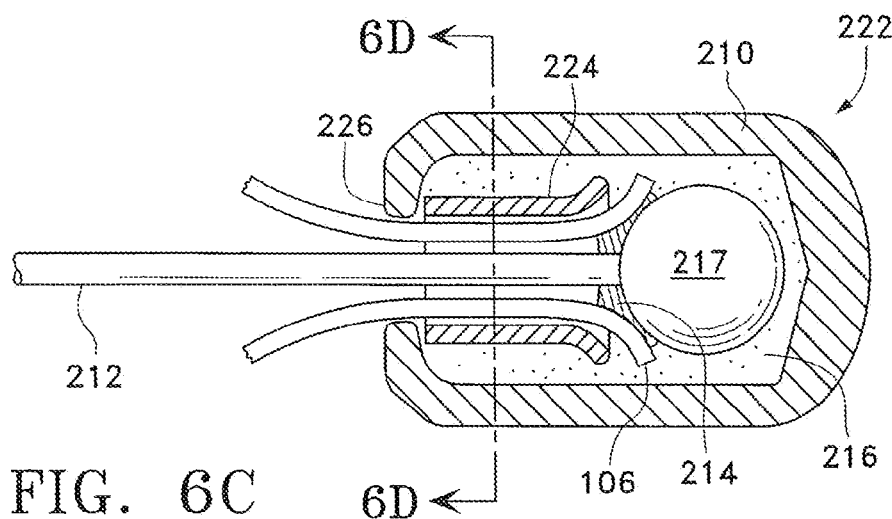
Figure 6D:
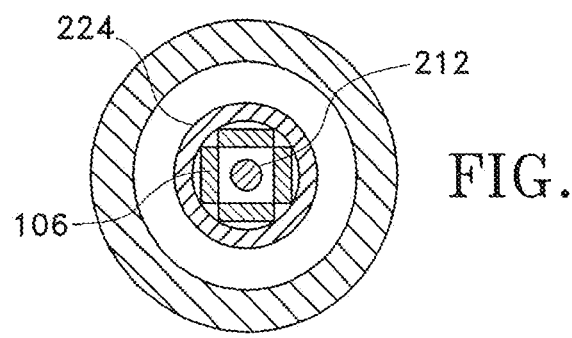

FIG. 6C illustrates another variation of a distal tip 222 having a redundant joint. The distal tip 222 has a polymeric cap 210 covering the distal ends of the basket legs 106 and wire 212. The legs 106 are soldered 214 to the distal end of the wire 212. Also used to maintain the joint is an adhesive 216 substantially filling the polymeric cap 210. A hypo-tube 224 covers the legs 106 and wire 212. A side view of the hypo-tube 224 is shown in FIG. 6D. The distal end of the hypo-tube 224 may be flared to seat a ball 217 located on a distal end of the wire 212 and the legs 106. The ball 217 may be integral with the wire or welded to the wire 212 such that when the wire 212 is put in tension, ball 217 pushes against legs 106, opening the basket. Opening the basket, therefore, reinforces the joint at the distal tip 222. Examples of suitable materials for the wire 212 and ball 217 include stainless steels and alloys. Although ball 217 is shown as spherical for purposes of illustration, the invention is not so limited. Ball 217 may take on other shapes such as a cylinder, box, lip, etc.

A proximal end of the hypo-tube 224 may likewise be flared to provide greater interlock with ends 226 of the polymeric cap 210. As shown in FIG. 6C, the ends of the legs 106 taper outwards from the hypo-tube 224 and form an area with a diameter larger than the end of the cap 226 which may be tapered down around the legs 106 and wire 212. The ends 220 of the polymeric cap 210 may be heat formed or otherwise tapered down.

The present invention also includes applying coatings to the basket legs and pull wire. The coatings accomplish a number of purposes including electrical insulation, lubrication, and energy focusing. For example, when a basket leg acts as an electrode itself, a portion of each leg may be coated with an insulting material, defining an uncovered active region. Well defined active regions deliver focused energy to the airway walls to be treated. Suitable coatings include but are not limited to heat shrinkable polymeric materials such as polyester as well as other non-heat shrinkable polymeric materials. Preferably, the wall or coating thickness is about 0.005 to 0.026 mm when measured in an expanded un-shrunken state. The coating, however, may have another thickness.

The pull wire may also be coated with an insulating coating. Preferably, the pull wire coating has lubricious properties as well. An example of a suitable coating for the pull wire is polytetrafluorethlene (PTFE). The thickness of the pull wire coating preferably ranges from about 0.005 to 0.05 mm. A suitable thickness of the pull wire coating is about 0.013 mm.

In configurations where the pull wire 212 supplies current to the legs 106, the pull wire preferably makes electrical contact with the legs 106 at the distal joint. Preferably, electrical contact is made between the pull wire 212, basket legs 106, and an enlarged member 217 such as a ball. Solder may also be applied to the distal joint to ensure electrical contact between the pull wire 212, basket legs 106, and a ball 217. Although the enlarged member 217 is shown as a spherical ball, the enlarged member need not be spherical-shaped. It may be, for example, cylindrical, square, oval, or otherwise configured.

Figure 6E:
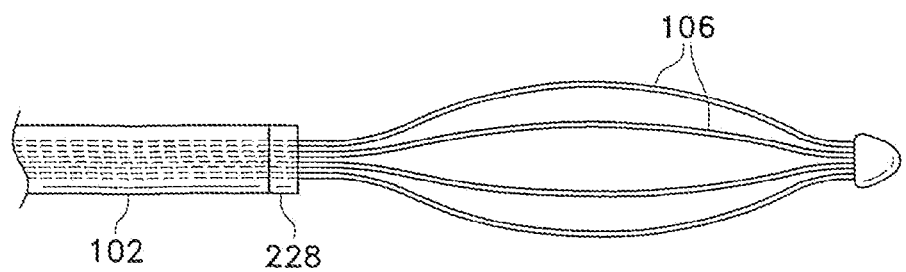

FIG. 6E shows another variation of the invention having a hoop or ring 228 at a proximal joint of the device. The hoop 228 may be soldered or welded to the legs 106 and keeps the legs 106 attached even if a joint fails between the legs and the elongate member 102. Also, the hoop 228 may electrically connect the legs, preventing disconnection of single leg 106 having a temperature sensing element attached.

FIG. 6F shows another variation of the invention having a disk 230. Disk 230 includes openings 231 for receiving each of the basket legs 106. The basket legs 106 are fed through openings 231 and into the elongate member 102. As shown in FIG. 6G, basket legs 106 may include bends 232 to mechanically interlock the disk and the legs. Adhesives may also be used to supplement the lock between the disk 230 and legs 106.

FIG. 6H shows another variation of the invention having a helicopter-shaped retainer 235. Each arm of the retainer 235 can be bonded or welded to an end portion of a leg 106 and the whole inserted into the end of the elongate member 102. Similar to the ring 228 and disk 230 described above, the retainer 235 increases the amount of force required for a basket leg 106 to dislodge from the elongate member.

The strength of the proximal joint may be further improved by adding a notch 236 to each of the legs 106 as shown in FIG. 6J. The notch 236 is located at the proximal end of the leg 106 and interlocks with the lumen of the elongate member when inserted therein. The material surrounding the notch is adhesively bonded, fused, thermoformed, ultrasonically welded, melted, crimped, or otherwise modified to interlock or bind the legs to the elongated body or member 102. Preferably, a redundant proximal joint is formed by adding adhesive, such as UV curable adhesive, to the joint prior to heat treatment. Of course, the notch need not be identical to that shown in FIG. 6J but can be any number of shapes such as those shown in FIGS. 6K and 6L. Additionally, a tab (not shown) may be cut or punched into the end of each of the legs 106. Like the notch 236, the tab interlocks with the lumen of the elongate member. The tab provides additional surfaces upon which interlocking can take place. The tab may also be bent to accommodate a number of interlocking configurations.

When crimping the lumen to the basket legs, care should be taken to ensure the central "pull-wire" lumen is not crushed or substantially modified. In one variation (not shown), a second protective layer of material, or coating, circumferentially surrounds the central lumen. Preferably, the second coating is a material which has a stiffness capable of withstanding the crimping forces used to crimp the outer lumen around the basket legs. Suitable materials for the second coating or protective layer include, for example, polymers and metals which have a higher stiffness than the material used to form the outer lumen. The protective layer need not extend the entire length of the catheter.

Another variation of the present invention is illustrated in FIG. 6M. In FIG. 6M, the basket legs 106 include hooks 237A, 237B which mechanically interlock with the elongate member 102. L-shaped hook 237B works identically to J-shaped hook 237A except that it does not extend beyond the outer surface of the elongate member. Thus, L-shaped hook 237B has less friction during manipulation of the elongate member within a sheath or body lumen.

Figure 6N:
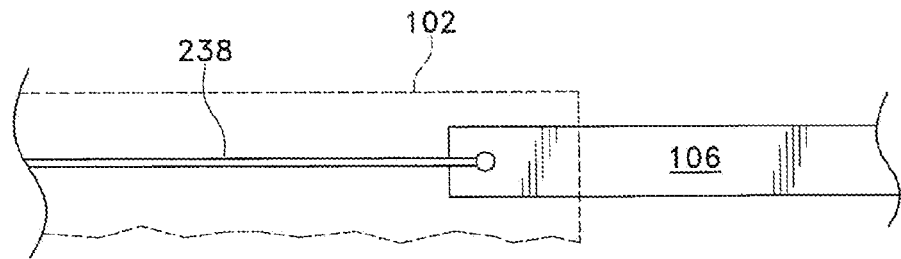

FIG. 6N illustrates yet another variation of the present invention having a safety 238. The safety or tether 238 prevents the basket legs from dislodging from the elongate member without stiffening it. The safety is preferably a thin flexible wire having one end affixed to the proximal end of the basket legs 106 and another end portion affixed to the elongate member 102. The ends may be affixed by, for example, winding, welding or adhesives. The safety 238 provides additional surface area for adhesive bonds to be formed with the elongate member, thereby increasing retention of the legs. Due to the thickness and flexibility of the safety, the stiffness of the elongate member is not significantly increased. Regardless of which variation is employed, it is preferred to use more than one of the above described mechanisms to interlock the basket legs to the elongate member.

Figure 6O:
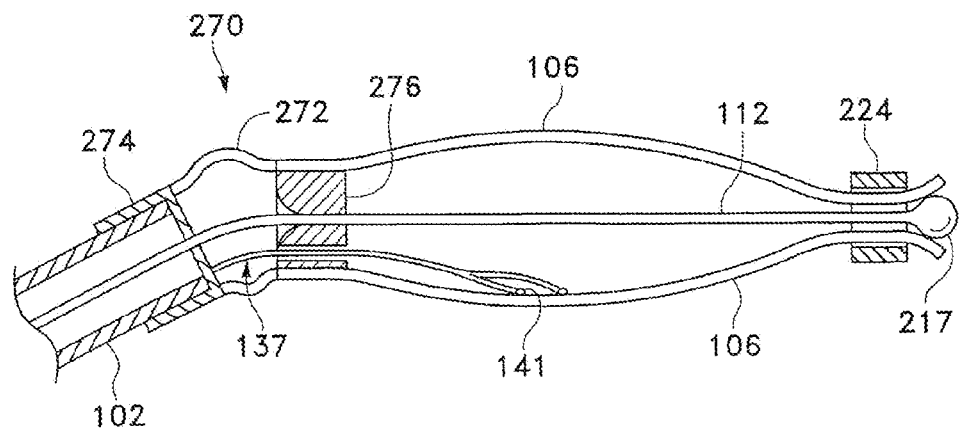

FIG. 6O illustrates another variation of the present invention. The apparatus shown in FIG. 6O includes a swivel joint 270 connecting legs 106 with elongate member 102. The swivel joint 270 rotates with legs 106 thereby reducing stresses which can, for example, cause one of the legs 106 to invert or lock in an undesired position. Inward leg buckling or leg inversion is undesirable because the energy active region of the basket leg may lose contact with the target tissue.

The swivel joint 270 may be integral with the elongate member in the form of a thin or necked down region. Alternatively, the swivel joint may comprise a separate hinge 272. Examples of suitable swivel joints include gimbals-type rings, or partial rings which allow rotation between the connecting legs 106 and the elongate member 102. As shown in FIG. 6O, an end-cap 274 connects hinge 272 with the elongate member. Swivel joint 270 also can include an insert 276 for interlocking the legs 106 with the hinge as well as provide a pathway or groove for the pull wire 112 and thermocouple 137 to slide through. Suitable materials for the swivel joint include but are not limited to injection molded polymers, metals, and alloys.

Inward leg buckling or leg inversion can also be prevented by disposing basket supports (not shown) inside the expandable basket. Basket supports may have a number of shapes or forms including but not limited to springs, cones, balloons, and baskets. Examples of spring basket supports include simple plate springs, compound leaf springs with or without lamination, and helical springs. One end of the spring is coupled to, for example, either the proximal or the distal joint, and the other end of the spring is coupled to a basket leg. Examples of cone basket supports include resilient cones disposed inside the basket at one or both ends of the basket. Expandable foam materials may also be used. The expandable foams may be cone or otherwise shaped. Balloons may also be deployed inside the basket and expanded to prevent inward deflection of the basket legs. The basket supports may also be in the form of a basket. Inner baskets may be made of metals or alloys thereof. A highly flexible inner basket can be made of, for example, nitinol.

The invention also includes a temperature detecting element (not shown). Examples of temperature detecting elements include thermocouples, infrared sensors, thermistors, resistance temperature detectors (RTDs), or any other apparatus capable of detecting temperatures or changes in temperature. The temperature detecting element is preferably placed in proximity to the expandable member. In the variation illustrated in FIG. 5B, a temperature sensor may be mounted along the pull wire 116. For the variations depicted in FIG. 5J-5L, a temperature sensor may be mounted between the energy transfer elements 132, 136, 138 and the leg 106. In one variation of the invention a temperature sensor is placed on a single basket leg 106 to provide a signal to control energy transfer. It is also contemplated that a temperature sensor may be placed on more than one basket leg 106, and/or on a central wire 116 to provide control for multiple areas of energy transfer. The temperature sensor may be placed on the inside of the basket leg 106 to protect the temperature sensor while still providing a position advantageous to determining the device temperature at the energy transfer element.

Figure 5M:
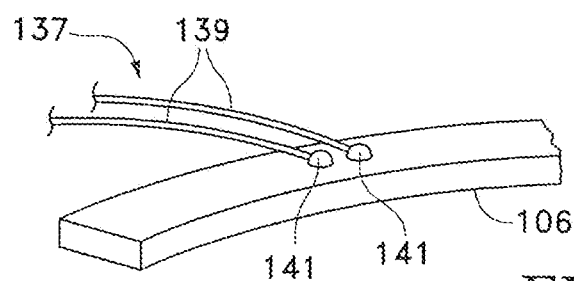
FIGS. 5M-5Q show a partial view of a thermocouple attached to a basket leg.

FIG. 5M illustrates a variation of the invention having thermocouple leads 139 attached to a leg 106 of the device. The leads may be soldered, welded, or otherwise attached to the leg 106. This variation of the invention shows both leads 139 of the thermocouple 137 attached in electrical communication to a leg 106 at separate joints 141. In this case, the temperature sensor is at the surface of the leg. This variation provides in case either joint becomes detached, the circuit will be open and the thermocouple 137 stops reading temperature. The device may also include both of the thermocouple leads as having the same joint.

Figure 5N:
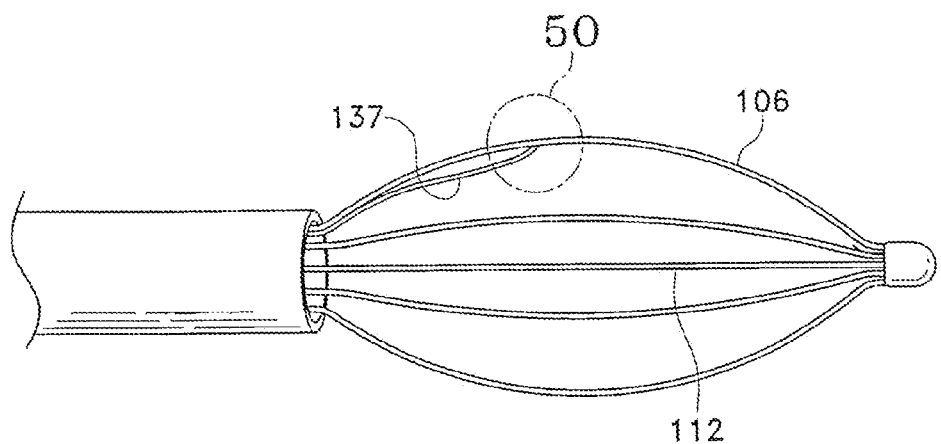
Figure 5O:
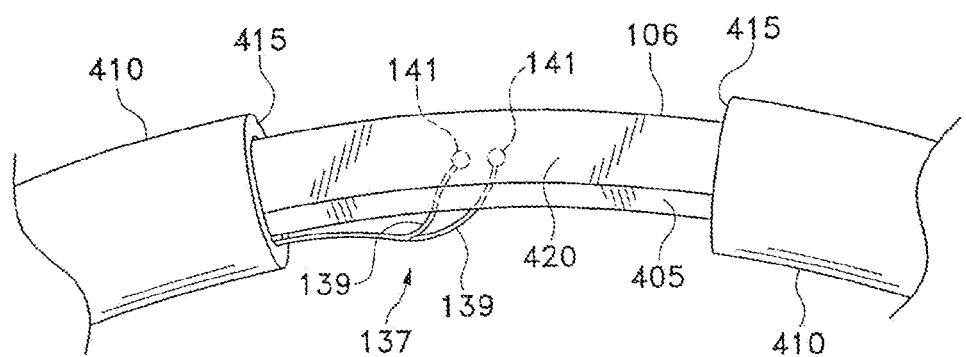

FIG. 5N is a partial view of a variation of the invention having thermocouple 137 positioned about midway along basket leg 106. FIG. 5O is an enlarged partial view of the thermocouple 137 of FIG. 5N showing the leads 139 separately coupled on an inwardly-facing surface of the leg 106. Consequently, the basket leg itself is used as part of the thermocouple junction upon which the temperature measurement is based. In other words, the thermocouple junction is intrinsic to the basket leg. This configuration is preferred because it provides an accurate temperature measurement of tissue contacting the leg 106 in the vicinity of the thermocouple leads. In contrast, typical thermocouple configurations consist of a thermocouple junction offset or extrinsic to the basket leg. We believe that thermocouple junctions having an offset from or extrinsic to the basket leg do not measure temperature as accurately in certain applications as thermocouple junctions which are intrinsic to the basket leg.

The leads 139 may be placed at other locations along the leg 106 including an edge 405. Joining the leads 139 to the edge 405, however, is undesirable because of its relatively small bonding surface.

FIG. 5O also shows basket leg 106 having an outer insulating material or coating 410. The boundaries 415 of the insulating material 410 define an uninsulated, active section of electrode leg 106 which delivers energy to the tissue walls. It follows that by controlling the area of the active section, delivery of the energy can be controlled. Preferably, the insulating coating 410 is heat shrink tubing or a polymeric coating. However, other insulating materials may be used.

Figure 5P:
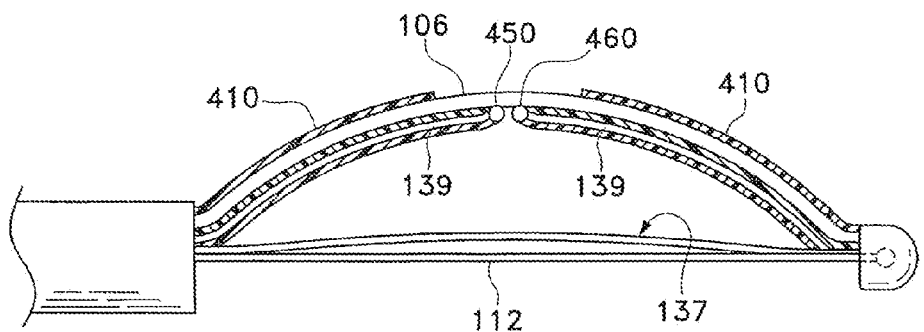
Figure 5Q:
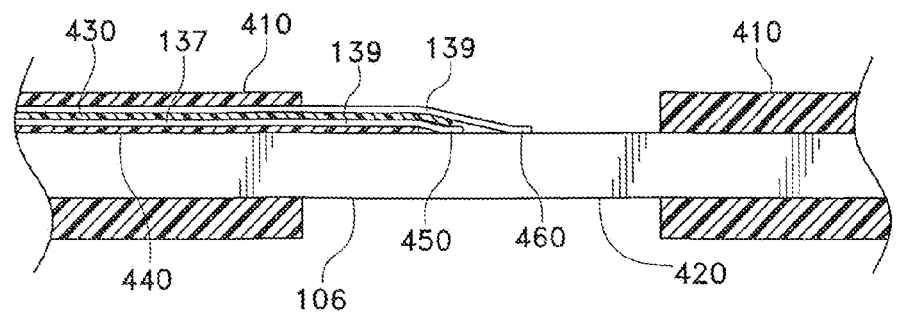

FIGS. 5P-5Q show another variation of the present invention having thin foil or laminated thermocouple leads 139. The thermocouple leads 139 are configured as foils or layers which can be, for example, prefabricated foils or sputtered films. Suitable materials for the thermocouple leads (listed in pairs) include, but are not limited to: Constantan and Copper; Constantan and Nickel-Chromium; Constantan and Iron; and Nickel-Aluminum and Nickel-Chromium. The thermocouple pair, CHROMEL and ALUMEL (both of which are registered trademarks of Hoskins Manufacturing) is preferred. CHROMEL and ALUMEL is a standard thermocouple pair and has shown to be biocompatible and corrosion resistant in our applications. The thermocouple leads 139 may be placed such that each lead approaches the center of the basket leg from an opposite end of the basket leg. The leads 139 then terminate in bond joints 440 and 450. Alternatively, as shown in the configuration of FIG. 5Q, both thermocouple leads 139 may run from the same end of the basket leg 106.

Preferably, insulating layers 430 and 440 are disposed between the thin film leads 139 and the basket leg 106. The insulating layers 430 and 440 electrically separate the leads 139 as well as electrically separate the leads from the leg 106. The insulating layers 430 and 440 limit the thermocouple junction to bond joints 450 and 460, which are optimally positioned on active region 420 of basket leg 106.

FIG. 7A-7D illustrate variations of the device in which impedance may be varied by wiring the basket legs 106 in series or in parallel. FIG. 7A illustrates a series wiring diagram in which a current path 142 flows from a first leg to a second leg 106, a third leg 106, and a fourth leg 106 sequentially. FIG. 7B illustrates the series wiring diagram and shows a single wire 143 connecting the legs 106 in series. The wire 143 may, for example, extend to a distal end of the leg and wrap over itself to the proximal end of the leg 106. A covering (not shown) may be placed over the wire 143 wrapped leg 106 at the proximal end of the device. FIG. 7C illustrates another variation of a series wiring diagram. In this example, a wire 143 extends from the proximal end of a leg 106 to its distal end and then extends to the distal end of an adjacent leg 106 and extends back to the proximal end of the adjacent leg 106.

FIG. 7D illustrates a parallel wiring diagram in which a current path 142 flows to each leg 106. Series wiring has an added advantage in that all current will pass through each energy transfer element. By design, this configuration equalizes the heat dissipated at each leg through construction of legs with equal resistance. In addition, in the event of failure of any electrical connection, no energy is delivered. This provides an additional safety feature over parallel wiring. As mentioned elsewhere, the electrical current may be AC or DC. AC may be delivered in the RF range as a safety measure additional to electrical isolation. DC may be used to allow a portable device powered by a battery pack or provide an energy source within the device itself.

Figure 8A:
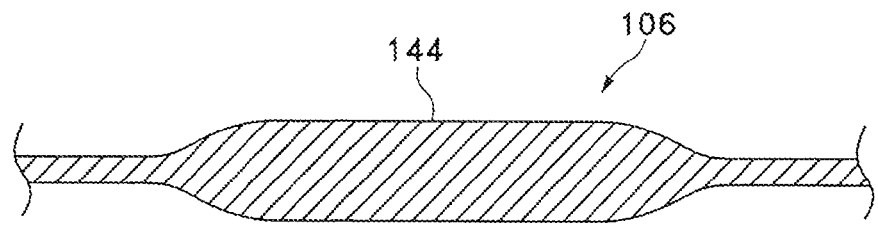
Figure 8B:
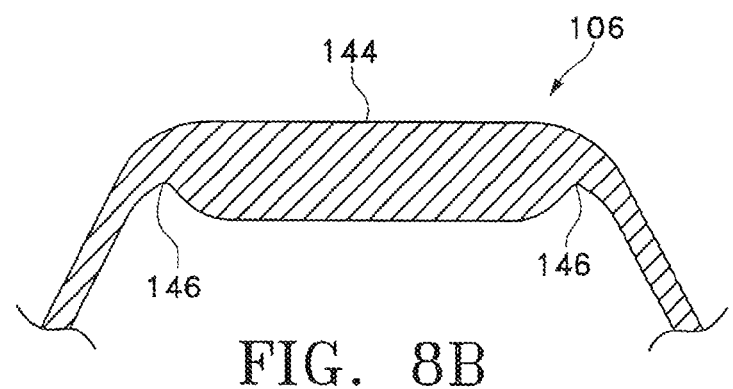
Figure 8C:
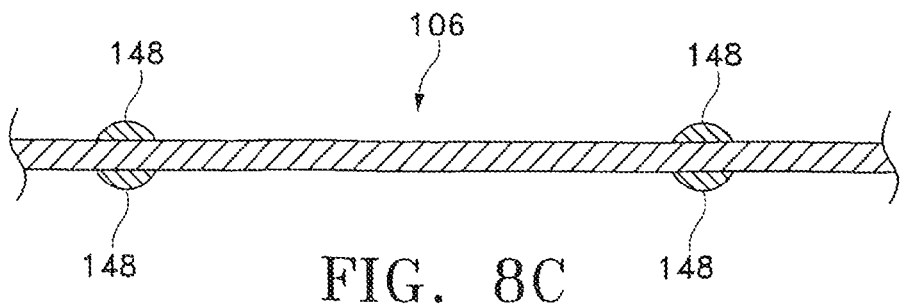

FIG. 8A-8C illustrates variation of the legs 106 of the basket 104. As discussed above, the legs may, for example, comprise a stainless steel, or a shape memory/superelastic alloy such as a nitinol material. The basket legs 106 may have a rectangular cross section in those variations where the legs 106 are formed from ribbons, or the legs 106 may have a circular cross section in variations where the legs 106 are formed from wires. Also, a leg 106 may be configured to have a non-axisymmetric cross-section. Also, the leg may have an oval or flat cross section as well. The legs 106 of a basket 104 need not all have similar cross sections. For instance, the cross section of each of the legs 106 in a basket 104 may be individually chosen to optimize such factors as the resilience of the basket 104, or to optimize energy transfer characteristics. An example of a cross section of a basket leg 106 is seen in FIG. 8A which illustrates a top view of a basket leg 106 that has a contoured shape 144. In this illustration, the energy exchange element is not shown in the figure for clarity. One of the purposes of such a contoured shape 144 is illustrated in FIG. 8B. When the basket (not shown) expands to its second state, leg 106 is configured to bend at or substantially near to points 146. A benefit of such a configuration is to allow a substantially parallel active surface as defined by the contour shape 144. FIG. 8C illustrates another variation of a leg 106. In this variation, the leg 106 has a region of increased diameter 148 in the case of round wire, or increased width or thickness in the case of rectangular or other non-axisymmetric wire. Such a region 106 could also be a flat wire with bumps or protrusions creating areas of increased width of the flat wire. This region 148 may, for example, provide a stop that assists in locating insulation, heat shrink, or other external covering around the leg 106. Also contemplated is a leg 106 that consists of a composite construction. In this variation, the leg 106 may comprise of differing materials in predetermined regions to control the bending of the leg 106 as the basket 104 expands, or the leg may be constructed of different materials to selectively control regions of deliver of energy on the leg.

Figure 9A:
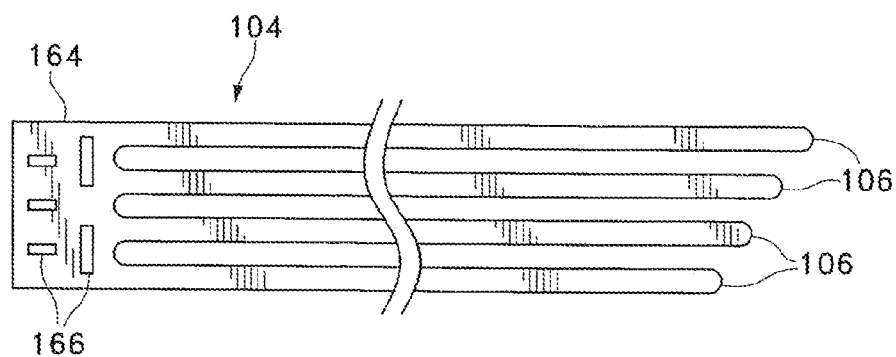
FIGS. 9A-9F illustrate examples of a basket formed from a single sheet or piece of material.
Figure 9B:
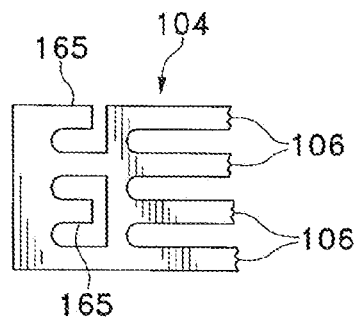
Figure 9C:
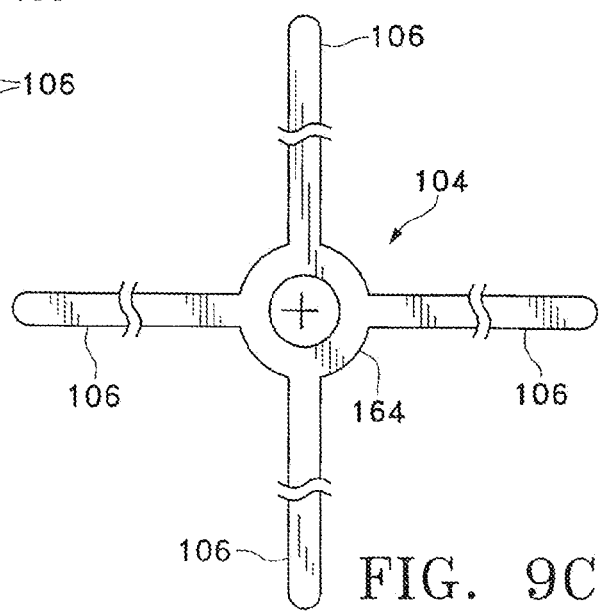
Figure 9D:
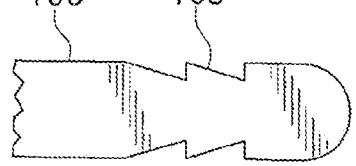

FIG. 9A-9F illustrate additional variations of the inventive device in which the expandable member comprises a basket comprised from a single piece or sheet of material. Such a configuration could comprise an etched, machined, laser cut, or otherwise manufactured piece of metal. FIG. 9A illustrates a partial view of a basket 104 formed from a single piece of material. The thickness of the material is, for example 0.005 inches, but may vary as desired. The illustration of FIG. 9A shows the basket 104 prior to being wrapped about the Z direction as indicated. As shown, the legs 106 may be of varying length or they may be the same length 106 or a combination thereof. The basket 104 may have a distal portion 164 or basket head 164 which may be configured to facilitate construction of the device. For example, the basket head 164 may be notched 166 to obtain a desired shape as the basket is wrapped about the Z direction. FIG. 9B illustrates a variation of the basket head 165 being notched such that sections 165 of the material may be bent from the plane of the material to form tabs 165. Tabs 165 may be used to form mechanical joints with another part, such as a distal tip cap. FIG. 9C illustrates another variation of a basket 104 made from a single piece of material. In this example, the legs 106 of the basket 104 are bent in a direction orthogonal to the plane of the basket head 164. In this example, the distance between the ends of the legs 106 may be, for example, about 2.75 inches. FIG. 9D illustrates a variation of the proximal ends of the legs 106 of the basket 104. In this example, the proximal ends of the legs 106 may have features 168 which promote the structural integrity of the proximal joint (not shown) of the device. As mentioned above, the proximal joint may be redundant. In this variation, the ends of the legs 106 have a saw-tooth design which improve the integrity of the proximal joint connecting the legs 106 to the elongated member. The variation of FIG. 9D also illustrates a proximal end of the leg 106 as having a radius, however, the end of the leg 106 may have other configurations as required. Also, the legs 106 may have a width of, for example, 0.012 inches and a separation of, for example, 0.016 inches. However, these dimensions may vary as needed.

Figure 9E:
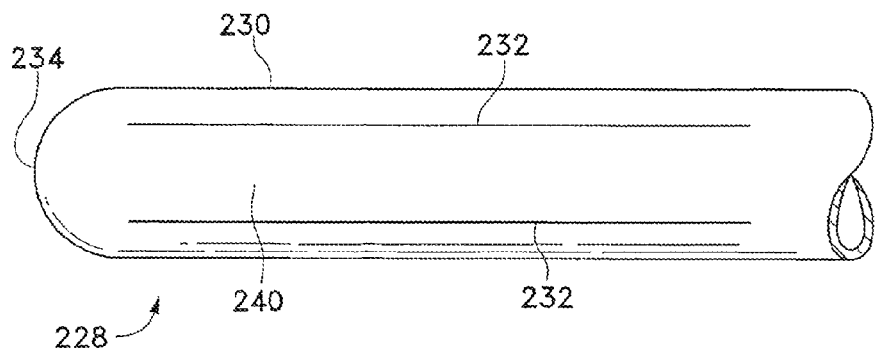
Figure 9F:
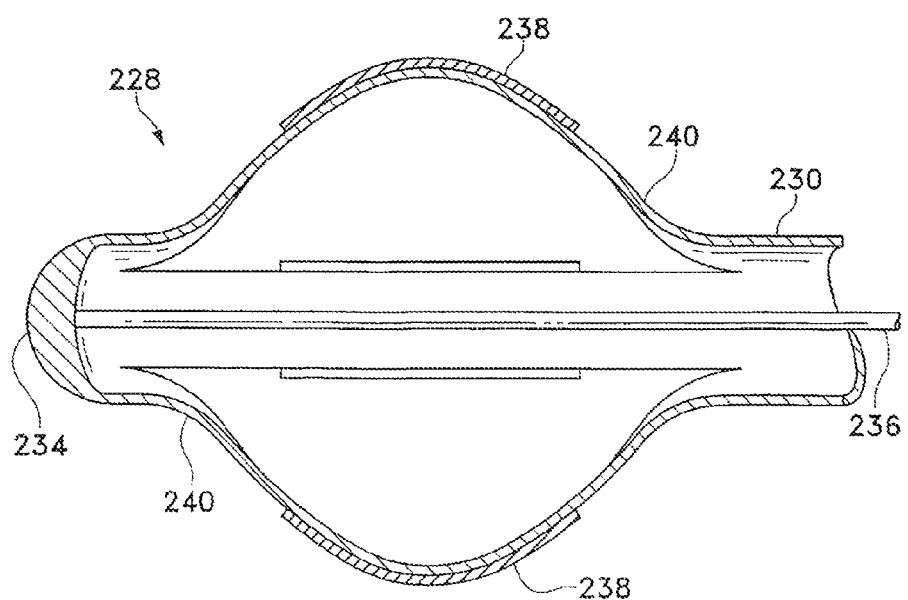

FIG. 9E illustrates a sectional view of a variation of the inventive device in which the expandable member comprises a tube 230 having slits or cuts 232 where the area between the slits or cuts 232 comprise legs 240 of the basket. FIG. 9F illustrates expansion of the basket of FIG. 9E. The legs 240 may be expanded by pulling a wire 236 that is attached to a tip 234 of the device in a proximal direction while the tube 230 remains fixed. As mentioned previously, the wire 236 may be used to conduct energy to the basket. Alternatively, the wire 236 may remain fixed as the tube 230 is advanced in a distal direction causing the legs 240 to bow outwards. The tube 230 may be cut or slit as required to obtain a desired number of legs or legs having a desired width. The tip 234 of the device may be selected to be rounded or atraumatic. The tip 234 may be fused, banded, soldered, welded or otherwise constructed as desired to be closed or rounded. The tube 230 may be selected to be conductive. In such a case, the tube 230 may be coated or covered with an insulator material (not shown) while a portion of the legs 240 will be left exposed or uncovered. This uncovered portion comprising an active surface of the basket which facilitates energy transfer. Alternatively, electrodes 238 may be placed on the legs 240 to provide an active region that facilitates energy transfer. The electrode 238 may be crimped, folded, welded, painted, deposited, or otherwise located on the leg 240. The tube 230 may be selected to have a varying thickness (not shown) to facilitate expansion of the basket, an interior passage, rigidity of the tube and ease of expansion of the basket. This variation provides advantages as the number of components making the device may be minimized and construction of the basket is simple.

Figure 10:
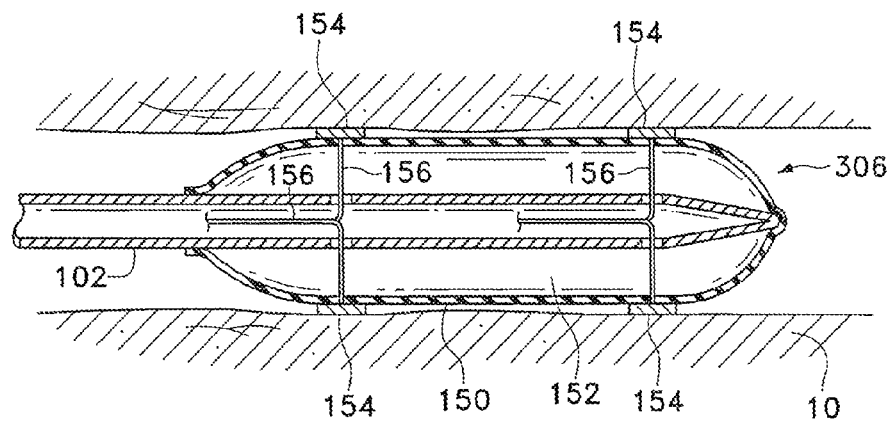
FIG. 10 is a side cross sectional view of a variation of the inventive device having a balloon with electrodes positioned exterior to the balloon.

FIG. 10 illustrates another variation of the inventive device 306 in which the expandable member comprises a balloon member 150. This variation of the device 306 includes electrodes 154 positioned on an exterior surface of the balloon member 150. The electrodes 154 may be connected to an energy source (not shown) by leads 156 extending through the balloon and through the lumen of an elongated member 102. The balloon member 150 may be filled with a fluid 152 such as saline or air to bring the electrodes 154 into contact with the airway wall 10. As noted above, the electrodes may also be resistance heating elements, RF electrodes, or another suitable element for conducting energy transfer with the airway. Also, a single electrode may continuously surround a circumference of a balloon 150, or a plurality of electrodes may be spaced at certain intervals to substantially surround the circumference of a balloon 150.

Figure 11:
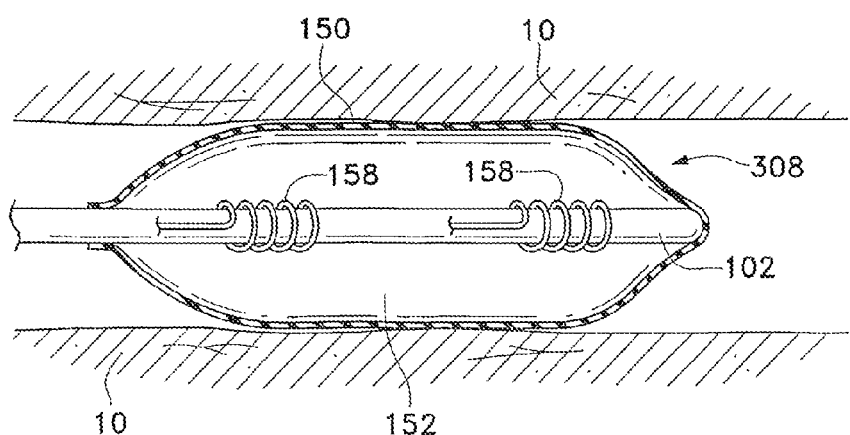
FIG. 11 is a partial side view of a variation of the inventive device having a balloon with heat generating elements positioned within the balloon for indirect heating of the tissue.

FIG. 11 illustrates another variation of the inventive device 308 in which the expandable member comprises a balloon member 150 in which a fluid 152 within the balloon member 150 is heated by a heat generating element 158. The heat generating elements 158 are illustrated in the shape of coils surrounding the shaft of the elongated member 102, however other types of heat generating elements (not shown) shapes may also be used. The heat generating elements 154 may be used as resistance heaters by application of an electric current to the heat generating elements. Alternatively, radio frequency or microwave energy may be applied to the heat generating elements 158 to heat fluid 152 within the balloon member 150. The fluid may be configured to optimize conductive heat transfer from the electrodes 158 to the exterior of the balloon member 150. The heat then passes from an exterior of the balloon 150 to the airway wall 10. Radio frequency or microwave energy may also be applied indirectly to the airway wall through the fluid and the balloon. In addition, hot fluid may be transmitted to the balloon member 150 from an external heating device for conductive heating of the airway tissue.

Figure 12:
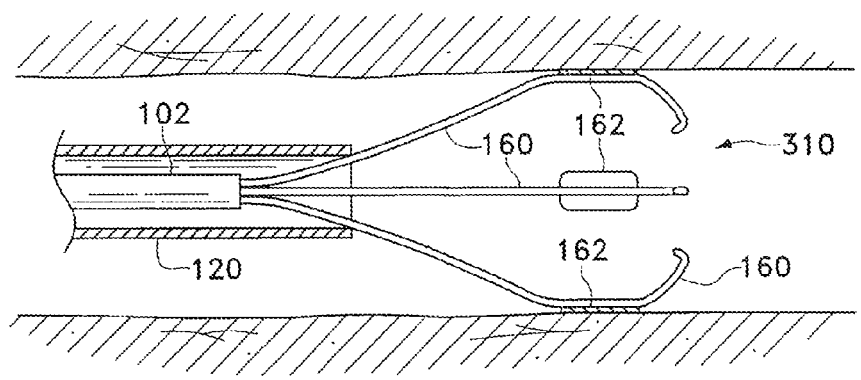
FIG. 12 is cross sectional view of the inventive device with electrodes and pre-shaped tines as the expandable member.

Another variation of the inventive device 310 is illustrated in FIG. 12 includes a plurality of energy transfer elements 162 positioned on pre-shaped tines 160. The pre-shaped tines 160 may be outwardly biased such that they expand from a first shape inside sheath 120 into a second expanded shape once advanced out of sheath 120. The tines 160 may also be configured so that they retract into a first state once withdrawn into a sheath 120. The pre-shaped tines 160 may be connected to an elongate member 102 which is positioned within a sheath 120. The pre-shaped tines 160 and the energy transfer elements 162 may be delivered through a delivery sheath 120 to a treatment site within the airways. When the pre-shaped tines 160 exit a distal end of the sheath 120, the pre-shaped tines 160 may bend outward until the energy transfer elements 162 come into contact with the airway walls for transfer of energy with the airway walls.

Figure 13:
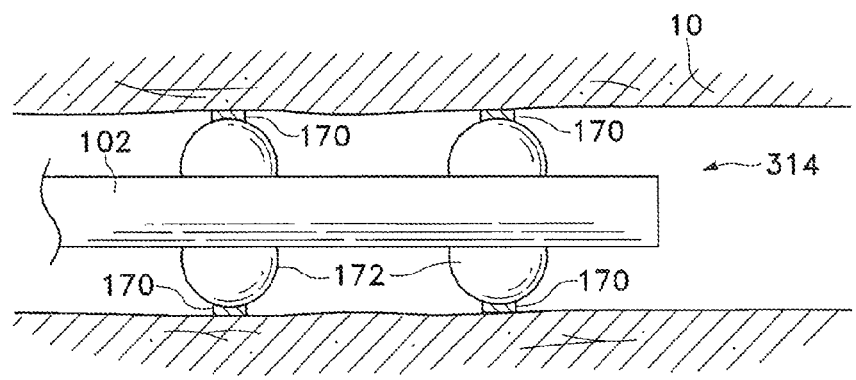
FIG. 13 is a cross sectional view of a variation of the inventive device with energy transfer elements positioned on expandable balloons.

FIG. 13 illustrates a variation of the inventive device 314 in which a elongated member 102 is provided with a plurality of energy transfer elements 170 positioned on at least one inflatable balloon 172. The energy transfer elements 170 may be RF electrodes or resistance heating elements. The balloons 172 are inflated through the elongated member 102 to cause the energy transfer elements 170 to come into contact with the airway walls 10. The energy transfer elements 170 are preferably connected to the energy source (not shown) by conductive wires (not shown) which extend from the energy transfer elements 170 through or along the balloons 172 and through the elongated member 102 to the energy source. In the variation where the energy transfer elements 170 are RF electrodes, the electrodes 170 may be used in a bipolar mode without an external electrode. Alternatively, the inventive device 314 may be operated in a monopolar mode with an external electrode (not shown, see FIG. 4). Another variation of the invention includes using resistance heating elements as the energy transfer elements 170. The energy transfer elements 170 may be a single continuous circular element or there may be a plurality of elements 170 spaced around the balloons 172.

Figure 14:
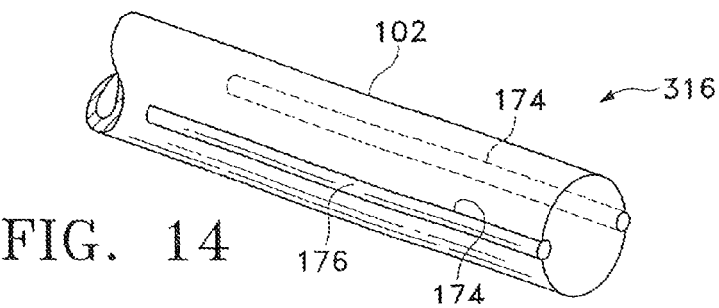
FIG. 14 is an illustration of a variation of the inventive device with electrodes positioned in grooves.

An alternative of the inventive device 316 of FIG. 14 includes an elongated member 102 having one or more grooves 174 in an exterior surface. Positioned within the grooves 174 are electrodes 176 for delivery of energy to the airway walls. Although the grooves 174 have been illustrated in a longitudinal pattern, the grooves may be easily configured in any desired pattern. Preferably, the inventive device 316 of FIG. 14 includes a biasing member (not shown) for biasing the elongated member 102 against an airway wall such that the electrodes 176 contact airway tissue. The biasing member (not shown) may be a spring element, an inflatable balloon element, or other biasing member. Alternatively, the biasing function may be performed by providing a preformed curve in the elongated member 102 which causes the device to curve into contact with the airway wall when extended from a delivery sheath (not shown).

Figure 15:
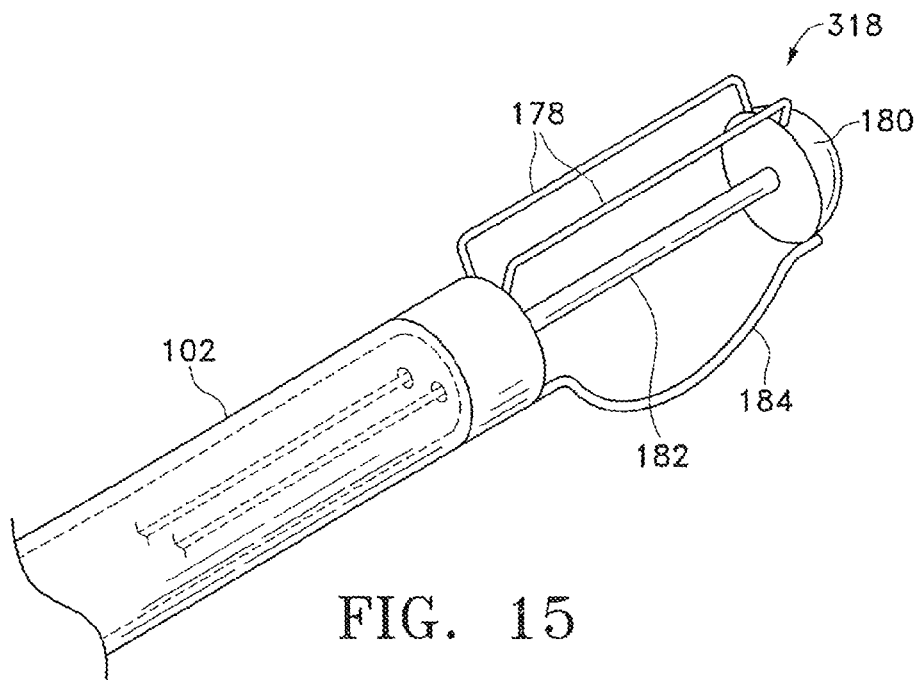
FIG. 15 is an illustration of a variation of the inventive device with electrodes and a biasing element.

FIG. 15 illustrates a variation of the inventive device 318 having one or more electrodes 178 connected to a distal end of an elongated tube 102. The electrodes 178 are supported between the distal end of the elongated tube 102 and a distal tip 180. A connecting shaft 182 supports the tip 180. Also connected between the distal end of the elongated member 102 and the distal tip 180 is a spring element 184 for biasing the electrodes 178 against a wall of the airway. The spring element 184 may have one end which slides in a track or groove in the elongated member 102 such that the spring 184 can flex to a variety of different positions depending on an internal diameter of the airway to be treated.

Figure 16:
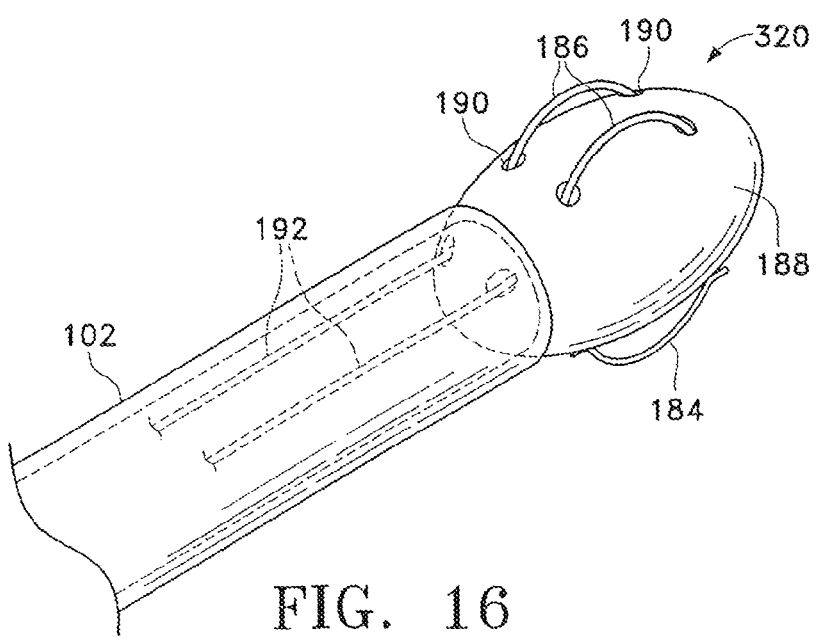
FIG. 16 is an illustration of another variation of the inventive device having electrodes and a biasing element.

FIG. 16 illustrates an alternative of the inventive device 320 in which the one or more electrodes 186 are positioned on a body 188 secured to an end of an elongated member 102. In the FIG. 16 variation, the body 188 is illustrated as egg shaped, however, other body shapes may also be used. The electrodes 186 extend through holes 190 in the body 188 and along the body surface. A biasing member such as a spring element 184 is preferably provided on the body 188 for biasing the body with the electrodes 186 against the airway walls. Leads 192 are connected to the electrodes 186 and extend through the elongated member 102 to the energy source not shown.

Figure 17:
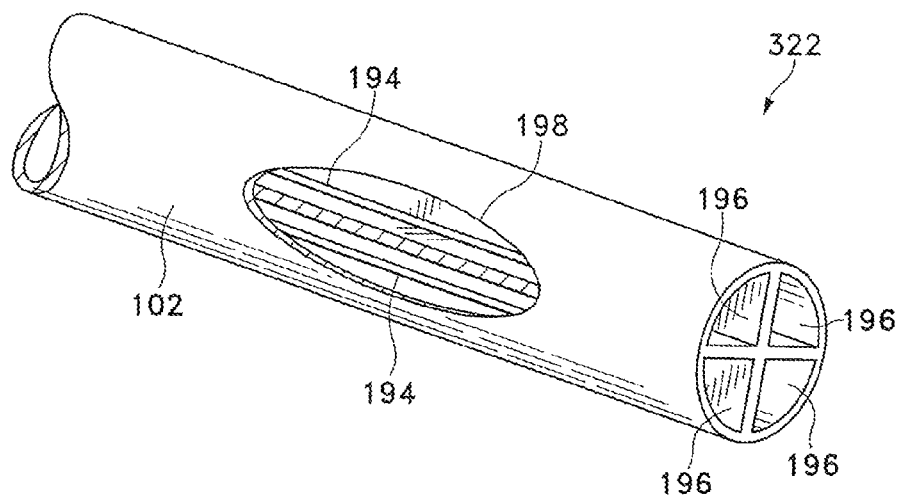
FIG. 17 is a partial side view of a variation of the inventive device having electrodes exposed by cut away sections of an elongated member.
Figure 18:
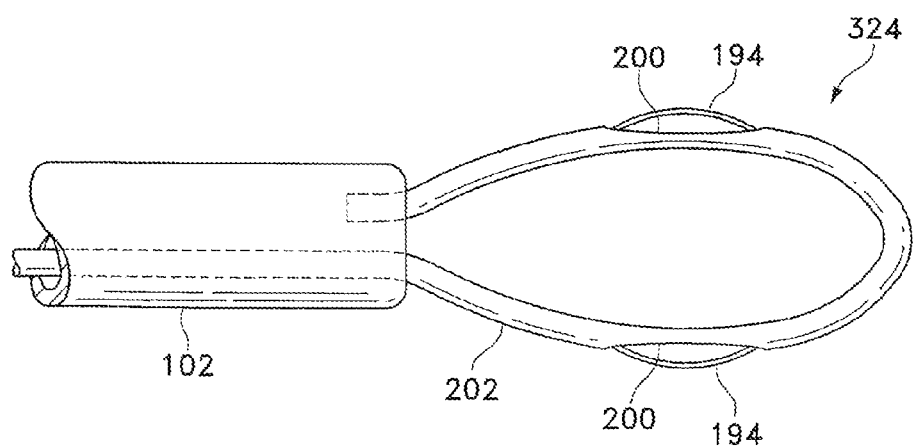
FIG. 18 is a partial side view of the inventive device with electrodes positioned on a loop shaped member.

FIGS. 17 and 18 illustrate embodiments of the invention 322, 324 in which electrodes 194 in the form of wires are positioned in one or more lumens 196 of an elongated member 102. Openings 198 are formed in side walls of the elongated member 102 to expose the electrodes 194 to the surrounding tissue. As shown in FIG. 17, the inventive device 322 may have multiple lumens 196 with electrodes 194 provided in each of the lumens 196. The side wall of the inventive device 322 is cut away to expose one or more of the electrodes 194 through a side wall opening 198. In FIG. 17, the opening 198 exposes two electrodes 194 positioned in adjacent lumens. The inventive device 322 may be provided with a biasing member as discussed above to bring the electrodes 195 of the device into contact with the airway wall.

Another variation of the inventive device 324 as shown in FIG. 18 includes an elongated member 102 which has an expandable loop shaped member 202 to allow the electrodes 194 to be exposed on opposite sides of the device 324 which contacts opposite sides of the airway. The resilience of the loop shaped member 202 causes the electrodes 194 to come into contact with the airway walls.

Figure 19:
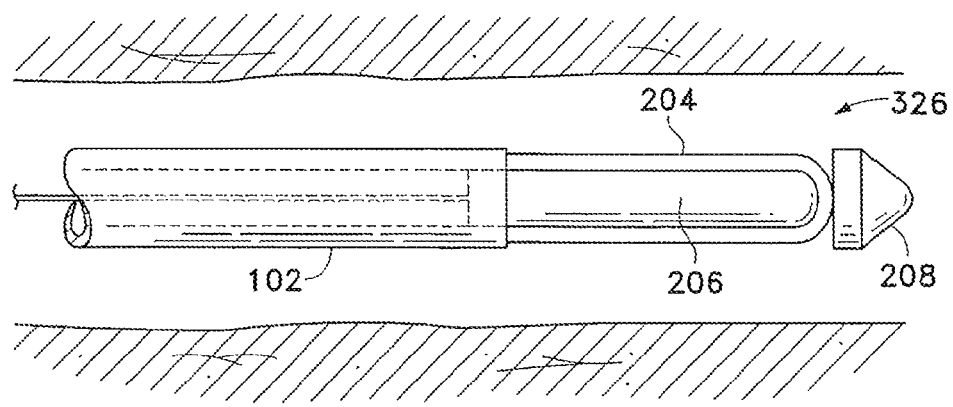
FIG. 19 is a cross sectional view of a variation of the inventive device having a looped shaped electrode in an unexpanded position.
Figure 20:
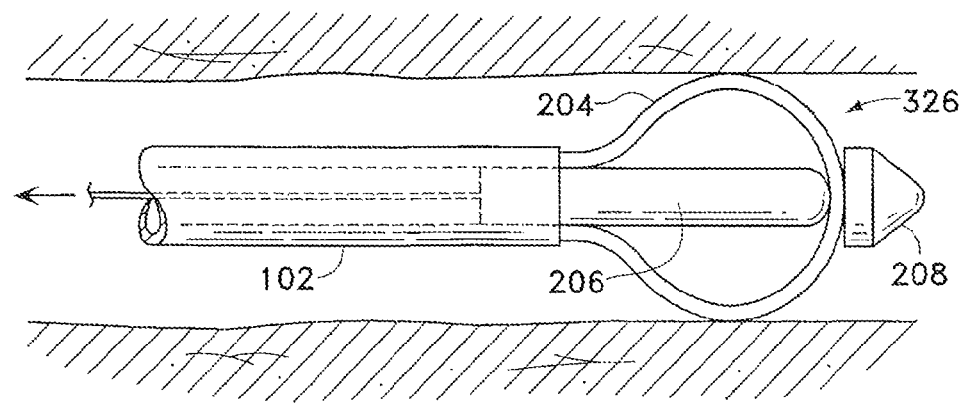
FIG. 20 is a cross sectional view of the variation of FIG. 19 with the looped shape electrode in an expanded position.

FIGS. 19 and 20 illustrate a further variation of the inventive device 326 having an expandable member 204 in a first non-expanded state and in a second expanded state. FIG. 19 illustrates the device as having one or more loop shaped electrodes 204 connected to an elongated member 102. In the unexpanded position shown in FIG. 19, the loop of the electrode 204 lies along the sides of a central core 206. A distal tip of the loop electrode 204 is secured to the core 206 and to a distal tip 208. The core 206 may be slideable in a lumen of the elongated member 102. Once the inventive device 326 has been positioned with the distal end in the airway to be treated, the electrode 204 is expanded by pulling the core 206 proximally with respect to the elongated member 102, as shown in FIG. 20. Alternatively, the electrode 204 or the core 206 may be spring biased to return to a configuration of FIG. 20 when a constraining force is removed. This constraining force may be applied by a delivery sheath or bronchoscope through which the inventive device 326 is inserted or by a releasable catch.

Figure 21:
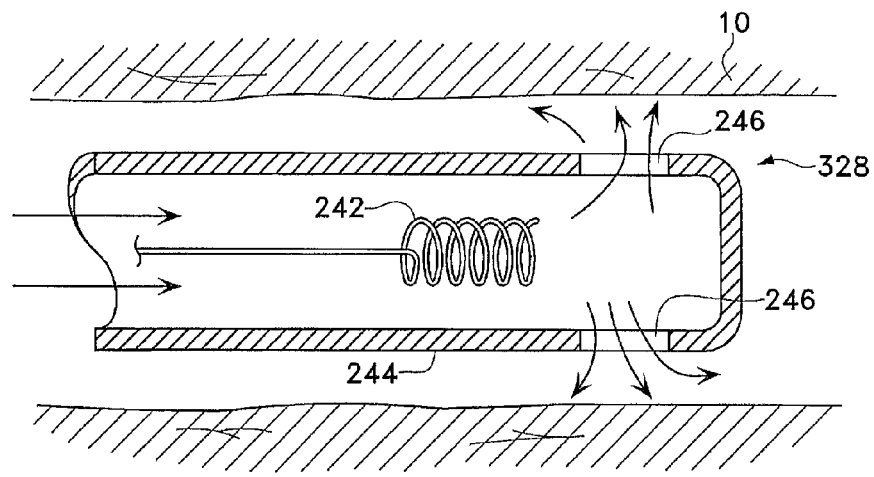
FIG. 21 is a side cross sectional view of a variation of a treatment device for treatment with heated fluid.

FIG. 21 illustrates a treatment device 328 for delivering heated fluid to the airway walls to heat the airway tissue. The device 328 includes a heating element 242 provided within a fluid delivery catheter 244. The fluid passes over the heating element 242 and out of openings 246 in the end of the catheter 244. The openings 246 are arranged to direct the fluid at the airway walls 100. The heating element 242 may be a coiled resistance heating element or any other heating element. The heating element 242 may be positioned anywhere along the body of the catheter 244 or may be an external heating device separate from the catheter.

The heating element 242 may also be replaced with a friction producing heating element which heats fluid passing through the fluid delivery catheter 244. According to one embodiment of a friction producing heating element, a friction element rotates and contacts a stationary element for purposed of heating the fluid.

Figure 22:
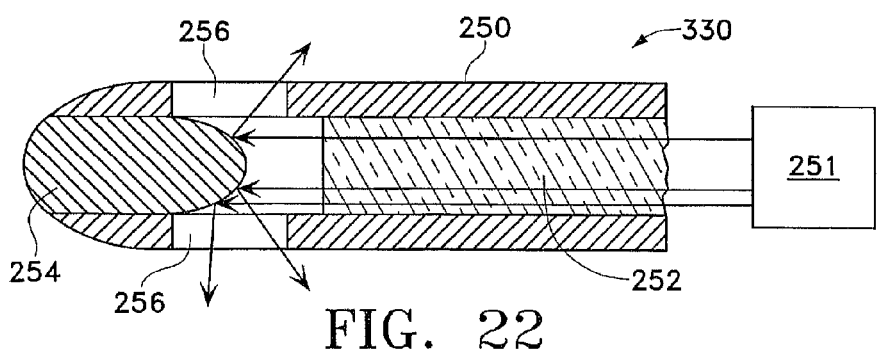
FIG. 22 is a side cross sectional view of a variation of a treatment device for treatment with radiation.

FIG. 22 illustrates a treatment device 330 for delivery of light or other radiant energy to the walls of the airway. The light delivery device 330 includes an outer catheter or sheath 250 surrounding a light transmitting fiber 252. A light directing member 254 is positioned at a distal end of the light delivery device for directing the light to the airway walls. The sheath 250 includes a plurality of windows 256 which allow the light which has been redirected by the light directing member 254 to pass substantially radially out of the sheath. The light delivery device 330 is connected by a conventional optical connection to a light source 251.

The light used may be coherent or incoherent light in the range of infrared, visible, or ultraviolet. The light source 251 may be any known source, such as a UV laser source. The light source 251 may be an ultraviolet light source having a wavelength of about 180-308 nm, a visible light source, or an infrared light source preferably in the range of 800-2200 nm. The intensity of the light may vary depending on the application. The light intensity should be bright enough to penetrate any mucus present in the airway and penetrate the airway walls to a depth necessary to treat the selected tissue. The light intensity may vary depending on the wavelength used, the application, the thickness of the smooth muscle, and other factors. The light or other radiant energy may also be used to heat an absorptive material on the catheter or sheath which in turn conductively heats the airway wall.

Figure 23:
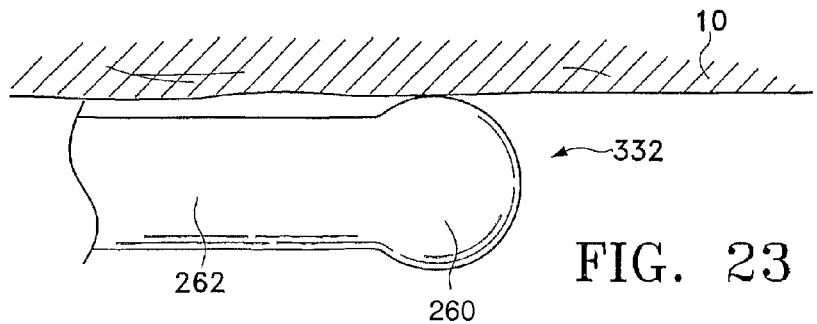
FIG. 23 is a side view of a variation of a treatment device for treatment with a cryoprobe.

FIG. 23 shows an alternative embodiment of a treatment device 332 including a cryoprobe tip 260 for transferring or removing energy in the from of heat from an airway wall 100. The cryoprobe tip 260 is delivered to the treatment site by a cryoprobe shaft 262. Transfer of energy from the tissue structures of the airway wall can be used in the same manner as the delivery of energy with any of the devices discussed above. The particular configuration of the cryoprobe treatment device 30$p$ may vary as is known in the art.

The treatment of the tissue in the airway walls by transfer of energy according to the present invention provides improved long term relief from asthma symptoms for some asthma sufferers. However, over time, some amount of smooth muscle or mucus gland cells which were not affected by an initial treatment may regenerate and treatment may have to be repeated after a period of time such as one or more months or years.

The airways which are treated with the device according to the present invention are preferably 1 mm in diameter or greater, more preferably 3 mm in diameter. The devices are preferably used to treat airways of the second to eighth generation, more preferably airways of the second to sixth generation.

Although the present invention has been described in detail with respect to devices for the treatment of airways in the lungs, it should be understood that the present invention may also be used for treatment of other body conduits. For example, the treatment system may be used for reducing smooth muscle and spasms of the esophagus of patients with achalasia or esophageal spasm, in coronary arteries of patients with Printzmetal's angina variant, for ureteral spasm, for urethral spasm, and irritable bowel disorders.

The devices and method describe herein provide a more effective and/or permanent treatment for asthma than the currently used bronchodilating drugs, drugs for reducing mucus secretion, and drugs for decreasing inflammation.

Moreover, the inventive device may also include a steering member configured to guide the device to a desired target location. For example, this steering member may deflect a distal tip of the device in a desired direction to navigate to a desired bronchi or bronchiole. Also contemplated it the use of the device with a vision system. Such a vision system may comprise a fiber optic cable which allows a user of the device to guide a distal tip of the device to its desired location. The vision system may include a CCD chip.

Also contemplated as the inventive device is the use of a power supply for providing energy as described above. The power supply provides the energy to be delivered to airway tissue via the energy transfer device. While the main goal of the power supply is to deliver enough energy to produce the desired effect, the power supply must also deliver the energy for a sufficient duration such that the effect persists. This is accomplished by a time setting which may be entered into the power supply memory by a user.

The power supply or generator of the present invention can employ a number of algorithms to adjust energy delivery, to compensate for device failures (such as thermocouple detachment), to compensate for improper use (such as poor contact of the electrodes), and to compensate for tissue inhomogeneities which can affect energy delivery such as, for example, subsurface vessels, adjacent airways, or variations in connective tissue.

A power supply may also include circuitry for monitoring parameters of energy transfer: (for example, voltage, current, power, impedance, as well as temperature from the temperature sensing element), and use this information to control the amount of energy delivered. In the case of delivering RF energy, typical frequencies of the RE energy or RF power waveform are from 300 to 1750 kHz with 300 to 500 kHz being preferred. The RF power-level generally ranges from about 0-30 W but depends upon a number of factors such as, size of the electrodes.

A power supply may also include control modes for delivering energy safely and effectively. Energy may be delivered in open loop power control mode for a specific time duration. Energy may also be delivered in temperature control mode, with output power varied to maintain a certain temperature for a specific time duration. In the case of RF energy delivery via RF electrodes, the power supply may operate in impedance control mode.

In temperature control mode with RF electrodes described here, the power supply will operate at up to a 75° C. setting. The duration must be long enough to produce the desired effect, but as short as possible to allow treatment of all of the desired target airways within a lung. For example, 5 to 10 seconds per activation (while the device is stationary) is preferred. Shorter duration with higher temperature will also produce acceptable acute effect.

Using RF electrodes as described above in power control mode, power ranges of 10-15 W with relatively long durations of 3-5 seconds are preferred but may be varied. It should be noted that different device constructions utilize different parameter settings to achieve the desired effect. For example, while direct RF electrodes typically utilize temperatures up to 75° C. in temperature control mode, the resistively heated electrodes may utilize temperatures up to 90° C.

Short bursts or pulses of RE energy may also be delivered to the target tissue. Short pulses of RF energy heat the proximal tissue while the deeper tissue, which is primarily heated by conduction through the proximal tissue, cools between the bursts of energy. Short pulses of energy therefore tend to isolate treatment to the proximal tissue.

The application of short pulses of RF energy may be accomplished by modulating the RF power waveform with a modulation waveform. Modulating the RF power waveform may be performed while employing any of the other control algorithms discussed herein. For example, the RF energy may be modulated while in a temperature control mode.

Examples of modulation waveforms include but are not limited to a pulse train of square waves, sinusoidal, or any other waveform types. In the case of square wave modulation, the modulated RF energy can be characterized in terms of a pulse width (the time of an individual pulse of RF energy) and a duty cycle (the percent of time the RF output is applied). A suitable duty cycle can be up to 100% which is essentially applying RE energy without modulation.

Also, in addition to the control modes specified above, the power supply may include control algorithms to limit excessive thermal damage to the airway tissue. The algorithms can be based on the expectation that the sensed temperature of the tissue will respond upon the application of energy. The temperature response, for example, may be defined as a change in temperature in a specified time or the rate of change of temperature. The expected temperature response can be predicted as a function of the initially sensed temperature, the temperature data for a specified power level as a function of time, or any other variables found to affect tissue properties. The expected temperature response may thus be used as a parameter in a power supply safety algorithm. For example, if the measured temperature response is not within a predefined range of the expected temperature response, the power supply will automatically shut down.

Other control algorithms may also be employed. For example, in order to stop delivery of energy in the event of contact between airway tissue and device legs having temperature sensing capabilities, an algorithm may be employed to shut down energy delivery if the sensed temperature does not rise by a certain number of degrees in a pre-specified amount of time after energy delivery begins. Preferably, if the sensed temperature does not increase more than about 10 degrees Celsius in about 3 seconds, the power supply is shut off. More preferably, if the sensed temperature does not increase more than about 10 degrees Celsius in about 1 second, the power supply is shut off.

Another way to stop energy delivery includes shutting down a power supply if the temperature ramp is not within a predefined range at any time during energy delivery. For example, if the measured rate of temperature change does not reach a predefined value, the power supply will stop delivery of the RF energy. The predefined values are predetermined and based on empirical data. Generally, the predefined values are based on the duration of time RF energy is delivered and the power-level applied.

Other algorithms include shutting down a power supply if a maximum temperature setting is exceeded or shutting down a power supply if the sensed temperature suddenly changes, such a change includes either a drop or rise, this change may indicate failure of the temperature sensing element.

For example, the generator or power supply may be programmed to shut off if the sensed temperature drops more than about 10 degrees Celsius in about 0.2 seconds. While the power supply or generator preferably includes or employs a microprocessor, the invention is not so limited. Other means known in the art may be employed. For example, the generator may be hardwired to run the above discussed algorithms.

Moreover, a variation of the invention includes configuring each energy exchange element independently to provide selective energy transfer radially about the device. As discussed above, another variation of the invention includes providing feedback control to determine the impedance of the airway to determine the power required by a power supply. Again, as discussed above, the feedback control could also be used to determine the size of the airway in which the device is positioned.

The treatment of an airway with the treatment device may involve placing a visualization system such as an endoscope or bronchoscope into the airways. The treatment device is then inserted through or next to the bronchoscope or endoscope while visualizing the airways. Alternatively, the visualization system may be built directly into the treatment device using fiber optic imaging and lenses or a CCD and lens arranged at the distal portion of the treatment device. The treatment device may also be positioned using radiographic visualization such as fluoroscopy or other external visualization means. The treatment device which has been positioned with a distal end within an airway to be treated is energized so that energy is applied to the tissue of the airway walls in a desired pattern and intensity. The distal end of the treatment device may be moved through the airway in a uniform painting like motion to expose the entire length of an airway to be treated to the energy. The treatment device may be passed axially along the airway one or more times to achieve adequate treatment. The "painting-like" motion used to exposed the entire length of an airway to the energy may be performed by moving the entire treatment device from the proximal end either manually or by motor. Alternatively, segments, stripes, rings or other treatment patterns may be used.

According to one variation of the invention, the energy is transferred to or from an airway wall in the opening region of the airway, preferably within a length of approximately two times the airway diameter or less, and to wall regions of airways distal to bifurcations and side branches, preferably within a distance of approximately twice the airway diameter or less. The invention may also be used to treat long segments of un-bifurcated airway.

According to one variation of the invention, the energy is transferred to or from an airway wall in the opening region of the airway, preferably within a length of approximately two times the airway diameter or less, and to wall regions of airways distal to bifurcations and side branches, preferably within a distance of approximately twice the airway diameter or less. The invention may also be used to treat long segments of un-bifurcated airway.

The invention includes a method of advancing a treatment device into a lung and treating the lung with the device to, at least, reduce the ability of the lung to produce at least one symptom of reversible obstructive pulmonary disease. It is contemplated that the treatment may reduce all of the symptoms of reversible obstructive disease. Alternatively, the treatment may be selected to address specific symptoms of the disease. It is also intended that the treatment of the lung may sufficiently reduce the symptoms of reversible obstructive pulmonary disease such that the patient is able to function as those free from the disease. Alternatively, the treatment may be such that the symptoms are reduced to allow the patient to more easily manage the disease. It is also intended that the effects of the treatment may be either long term or short term with repeating treatment necessary to suppress the symptoms.

The methods of the invention described herein may be performed while the lung is experiencing natural symptoms of reversible obstructive pulmonary disease. One such example is where an individual, experiencing an asthma attack, or acute exacerbation of asthma or COPD, undergoes treatment to improve the individual's ability to breath. In such a case, the treatment, called 'rescue,' seeks to provide immediate relief for the patient.

The method may also include the steps of locating one or more treatment sites within an airway of the lung, selecting one of the treatment sites from the locating step and treating at least one of the selected treatment sites. As mentioned above, these steps may be, but are not necessarily, performed while the lung is experiencing symptoms of reversible obstructive pulmonary disease.

The invention may further comprise the step of stimulating the lung to produce at least one artificially induced symptom of reversible obstructive pulmonary disease. For example, stimulation of the lung would preferably increase the resistance to airflow within the lung, constrict airways within the lung, inflame/irritate airway tissues, increase edema and/or increase the amount of mucus plugging of the airway. Stimulation of the lung may occur at any point during the procedure or before the procedure. For example, the lung may be stimulated either prior to or after, the step of locating a treatment site. If the lung is stimulated prior to the step of locating a treatment site, the reaction of the stimulated tissue within the lung may be useful in determining which locations are to be selected as treatment sites. The lung tissue or airway tissue within the lung may be stimulated by a variety of methods including but not limited to pharmacological stimulation, (e.g., histamine, methacholine, or other bronchoconstricting agents, etc.), electrical stimulation, mechanical stimulation, or any other stimuli causing obstructive pulmonary symptoms. For example, electrical stimulation may comprise exposing airway tissue to electrical field stimulation. An example of such parameters include 15 VDC, 0.5 ms pulses, 0.5-16 Hz, and 70 VDC, 2-3 ms pulses, 20 HZ.

The locating step described above may be performed using a non-invasive imaging technique, including but not limited to, a bronchogram, magnetic resonance imaging, computed tomography, radiography (e.g., x-ray), and ventilation perfusion scans.

The invention further includes the steps of testing the lung for at least one pre-treatment pulmonary function value prior to treating the lung with the device. After the lung is treated, the lung is re-tested for at least one post-treatment pulmonary function value. Naturally, the two pulmonary function values may be compared to estimate the effect of the treatment. The invention may also include treating additional sites in the lung after the re-testing step to at least reduce the effect of at least one symptom of reversible obstructive pulmonary disease. The invention may also include stimulating the lung to produce at least one artificially induced symptom of reversible obstructive pulmonary disease. As mentioned above, the stimulation of the lung may occur at any point during, or prior to, the procedure. For example, stimulation of the lung may occur prior to the step of testing the lung for pre-treatment pulmonary values. In this case, the values would be determinative of pulmonary function values of a lung experiencing symptoms of reversible obstructive pulmonary disease. Accordingly, the objective is to treat the lung until acceptable pulmonary function values are obtained. One benefit of such a procedure is that the effect of the treatment on the patient is more readily observed as compared to the situation where a patient, having previously been treated, must wait for an attack of reversible obstructive pulmonary disease to determine the efficacy of the treatment.

Pulmonary function values are well known in the art. The following is an example of pulmonary function values that may be used. Other pulmonary function values, or combinations thereof, are intended to be within the scope of this invention. The values include, but are not limited to, FEV (forced expiratory volume), FVC (forced vital capacity), FEF (forced expiratory flow), Vmax (maximum flow), PEFR (peak expiratory flow rate), FRC (functional residual capacity), RV (residual volume), TLC (total lung capacity).

FEV measures the volume of air exhaled over a pre-determined period of time by a forced expiration immediately after a full inspiration. FVC measures the total volume of air exhaled immediately after a full inspiration. Forced expiratory flow measures the volume of air exhaled during a FVC divided by the time in seconds. Vmax is the maximum flow measured during FVC. PEFR measures the maximum flow rate during a forced exhale starting from full inspiration. RV is the volume of air remaining in the lungs after a full expiration.

The locating step described above may also comprise identifying treatment sites within the airway being susceptible to a symptom of reversible obstructive pulmonary disease. For example, symptoms may include, but are not limited to, airway inflammation, airway constriction, excessive mucous secretion, or any other asthmatic symptom. Stimulation of the lung to produce symptoms of reversible obstructive pulmonary disease may assist in identifying ideal treatment sites.

As noted above, the method of the present invention may include stimulating the lung to produce at least one artificially induced symptom of reversible obstructive pulmonary disease and further include the step of evaluating the result of stimulation of the lung. For example, the evaluating step may include visually evaluating the effect of the stimulating step on the airway using a bronchoscope with a visualization system or by non-invasive imaging techniques, such as those describe herein. The evaluating step may include measuring pressure changes in the airway before and after the stimulating step. Pressure may be measured globally (e.g., within the entire lung), or locally (e.g., within a specific section of the lung such as an airway or alveolar sac.) Also, the evaluating step may comprise measuring the electrical properties of the tissue before and after the stimulating step. The invention may also include evaluating the results of the stimulating step by combining any of the methods previously mentioned. Also, the invention may further comprise the step of selecting at least one treatment parameter based upon the results of the evaluating step. Such treatment parameters may include, but are not limited to, duration of treatment, intensity of treatment, temperature, amount of tissue treated, depth of treatment, etc.

The method may also include the step of determining the effect of the treatment by visually observing lung, airway or other such tissue for blanching of the tissue. The term "blanching" is intended to include any physical change in tissue that is usually, but not necessarily, accompanied by a change in the color of the tissue. One example of such blanching is where the tissue turns to a whitish color after the treatment of application of energy.

The invention may also include the step of monitoring impedance across a treated area of tissue within the lung. Measuring impedance may be performed in cases of monopolar or bipolar energy delivery devices. Additionally, impedance may be monitored at more than one site within the lungs. The measuring of impedance may be, but is not necessarily, performed by the same electrodes used to deliver the energy treatment to the tissue. Furthermore, the invention includes adjusting the treatment parameters based upon the monitoring of the change in impedance after the treatment step. For example, as the energy treatment affects the properties of the treated tissue, measuring changes in impedance may provide information useful in adjusting treatment parameters to obtain a desired result.

Another aspect of the invention includes advancing a treatment device into the lung and treating lung tissue to at least reduce the ability of the lung to produce at least one symptom of reversible obstructive pulmonary disease and further comprising the step of sub-mucosal sensing of the treatment to the lung tissue. The sub-mucosal sensing may be invasive such as when using a probe equipped to monitor temperature, impedance, and/or blood flow. Or, the sub-mucosal sensing may be non-invasive in such cases as infra-red sensing.

The invention may also include using the treatment device to deposit radioactive substances at select treatment sites within the lung. The radioactive substances, including, but not limited to Iridium (e.g. $^{192}$Ir.) either treat the lung tissue over time or provide treatment upon being deposited.

The invention also includes scraping epithelial tissue from the wall of an airway within the lung prior to advancing a treatment device into the lung to treat the lung tissue. The removal of the epithelial tissue allows the device to treat the walls of an airway more effectively. The invention further comprises the step of depositing a substance on the scraped wall of the airway after the device treats the airway wall. The substance may include epithelial tissue, collagen, growth factors, or any other bio-compatible tissue or substance, which promotes healing, prevent infection, and/or assists in the clearing of mucus. Alternatively, the treatment may comprise the act of scraping epithelial tissue to induce yield the desired response.

The invention includes using the treating device to pre-treat the lung to at least reduce the ability of the lung to produce at least one symptom of reversible obstructive pulmonary disease prior to the treating step. At least one of the parameters of the pre-treating step may differ than one of the parameters of the treating step. Such parameters may include time, temperature, amount of tissue over which treatment is applied, amount of energy applied, depth of treatment, etc.

The invention may also include advancing the treatment device into the lung and treating the lung tissue in separate stages. One of the benefits of dividing the treating step into separate stages is that the healing load of the patient is lessened. Dividing of the treating step may be accomplished by treating different regions of the lung at different times. Or, the total number of treatment sites may be divided into a plurality of groups of treatment sites, where each group of treatment sites is treated at a different time. The amount of time between treatments may be chosen such that the healing load placed on the lungs is minimized.

The invention may also include advancing a treatment device into the lung, treating the lung with the device and sensing movement of the lung to reposition the treatment device in response to the movement. This sensing step accounts for the tidal motion of the lung during breathing cycles or other movement. Taking into account the tidal motion allows improved accuracy in repositioning of the device at a desired target.

The invention may also include the additional step of reducing or stabilizing the temperature of lung tissue near to a treatment site. This may be accomplished for example, by injecting a cold fluid into lung parenchyma or into the airway being treated, where the airway is proximal, distal, or circumferentially adjacent to the treatment site. The fluid may be sterile normal saline, or any other bio-compatible fluid. The fluid may be injected into treatment regions within the lung while other regions of the lung normally ventilated by gas. Or, the fluid may be oxygenated to eliminate the need for alternate ventilation of the lung. Upon achieving the desired reduction or stabilization of temperature the fluid may be removed from the lungs. In the case where a gas is used to reduce temperature, the gas may be removed from the lung or allowed to be naturally exhaled. One benefit of reducing or stabilizing the temperature of the lung may be to prevent excessive destruction of the tissue, or to prevent destruction of certain types of tissue such as the epithelium, or to reduce the systemic healing load upon the patient's lung.

Also contemplated as within the scope of the invention is the additional step of providing therapy to further reduce the effects of reversible obstructive pulmonary disease or which aids the healing process after such treatment. Some examples of therapy include, drug therapy, exercise therapy, and respiratory therapy. The invention further includes providing education on reversible obstructive pulmonary disease management techniques to further reduce the effects of the disease. For example, such techniques may be instruction on lifestyle changes, self-monitoring techniques to assess the state of the disease, and/or medication compliance education.

There may be occurrences where it is necessary to reverse the effects of the treatment described herein. Accordingly, the invention further includes a method for reversing a treatment to reduce the ability of the lung to produce at least one symptom of reversible obstructive pulmonary disease comprising the step of stimulating re-growth of smooth muscle tissue. The re-stimulation of the muscle may be accomplished by the use of electro-stimulation, exercising of the muscle and/or drug therapy.

The invention further includes methods of evaluating individuals having reversible obstructive pulmonary disease, or a symptom thereof, as a candidate for a procedure to reduce the ability of the individual's lung to produce at least one symptom of reversible obstructive pulmonary disease. The method comprises the steps of assessing the pulmonary condition of the individual, comparing the pulmonary condition to a corresponding pre-determined state, and evaluate the individual as a candidate based upon the comparison.

In assessing the pulmonary condition, the method may comprise the steps of performing pulmonary function tests on the individual to obtain a pulmonary function value which is compared to a predetermined value. Examples of pre-determined values are found above.

The method of evaluating may further include the step of determining how the individual's tissue will react to treatment allowing the treatment to be tailored to the expected tissue response.

The method of evaluating may further comprises the step of pulmonary function testing using a gas, a mixture of gases, or a composition of several mixtures of gases to ventilate the lung. The difference in properties of the gases may aid in the pulmonary function testing. For example, comparison of one or more pulmonary function test values that are obtained with the patient breathing gas mixtures of varying densities may help to diagnose lung function. Examples of such mixtures include air, at standard atmospheric conditions, and a mixture of helium and oxygen. Additional examples of pulmonary testing include tests that measure capability and evenness of ventilation given diffusion of special gas mixtures. Other examples of gases used in the described tests, include but are not limited to, nitrogen, carbon monoxide, carbon dioxide, and a range of inert gases.

The invention may also comprise the step of stimulating the lung to produce at least one artificially induced symptom of reversible obstructive pulmonary disease. Stimulating the symptoms of the disease in an individual allows the individual to be evaluated as the individual experiences the symptoms thereby allowing appropriate adjustment of the treatment.

The method of evaluating may also comprise the step of obtaining clinical information from the individual and accounting for the clinical information for treatment.

The method may further comprise the selection of a patient for treatment based upon a classification of the subtype of the patient's disease. For example, in asthma there are a number of ways to classify the disease state. One such method is the assessment of the severity of the disease. An example of a classification scheme by severity is found in the *NHLBI Expert Panel 2 Guidelines for the Diagnosis and Treatment of Asthma*. Another selection method may include selecting a patient by the type of trigger that induces the exacerbation. Such triggers may be classified further by comparing allergic versus non-allergic triggers. For instance, an exercise induced bronchospasm (EIB) is an example of a non-allergenic trigger. The allergic sub-type may be further classified according to specific triggers (e.g., dust mites, animal dander, etc.). Another classification of the allergic sub-type may be according to characteristic features of the immune system response such as levels of IgE (a class of antibodies that function in allergic reactions, also called immunoglobulin). Yet another classification of allergic sub-types may be according to the expression of genes controlling certain interleukins (e.g., IL-4, IL-5, etc.) which have been shown to play a key role in certain types of asthma.

The invention further comprises methods to determine the completion of the procedure and the effectiveness of the reduction in the lung's ability to produce at least one symptom of reversible obstructive pulmonary disease. This variation of the invention comprises assessing the pulmonary condition of the individual, comparing the pulmonary condition to a corresponding predetermined state, and evaluating the effectiveness of the procedure based on the comparison. The invention may also comprise the steps of performing pulmonary function tests on the individual to obtain at least one pulmonary function value, treating the lung to at least reduce the ability of the lung to produce at least one symptom of reversible obstructive pulmonary disease, performing a post-procedure pulmonary function tests on the individual to obtain at least one post pulmonary function value and comparing the two values.

This variation of the invention comprises obtaining clinical information, evaluating the clinical information with the results of the test to determine the effectiveness of the procedure. Furthermore, the variation may include stimulating the lung to produce a symptom of reversible obstructive pulmonary disease, assessing the pulmonary condition of the patient, then repeating the stimulation before the post-procedure pulmonary therapy. These steps allow comparison of the lung function when it is experiencing symptoms of reversible obstructive pulmonary disease, before and after the treatment, thereby allowing for an assessment of the improved efficiency of the lung during an attack of the disease.

Further details as to the use or other variation of the apparatus described herein may be drawn from the background which is intended to form part of the present invention. It is noted that this invention has been described and specific examples of the invention have been portrayed to convey a proper understanding of the invention. The use of such examples is not intended to limit the invention in any way. Additionally, to the extent that there are variations of the invention which are within the spirit of the disclosure and are equivalent to features found in the claims, it is the intent that the claims cover those variations as well. All equivalents are considered to be within the scope of the claimed invention, even those which may not have been set forth herein merely for the sake of brevity. Also, the various aspects of the invention described herein may be modified and/or used in combination with such other aspects also described to be part of the invention either explicitly or inherently to form other advantageous variations considered to be part of the invention covered by the claims which follow.

The invention described herein expressly incorporates the following co-pending applications by reference in their entirety: U.S. application Ser. No. 09/095,323; U.S. patent application Ser. No. 09/095,323—Methods and Apparatus for Treating Smooth Muscles in the Walls of Body Conduits; Ser. No. 09/349,715—Method of Increasing Gas Exchange of a Lung; and Ser. No. 09/296,040—Devices for Modification of Airways By Transfer of Energy; Ser. No. 09/436,455 Devices for Modification of Airways by Transfer of Energy.

We claim as our invention:

1. A device for delivering energy to tissue, the device comprising:
    a flexible elongate body having a proximal end and a distal end;
    an expandable electrode assembly disposed adjacent to the distal end of the elongate body, the electrode assembly including a plurality of electrically-conductive electrodes;
    an electrically-conductive member extending from the proximal end of the elongate body to the expandable electrode assembly, for supplying energy to the electrodes; and
    a thermocouple attached to at least one of the plurality of electrodes so that the at least one of the plurality of electrodes and the thermocouple form a thermocouple junction for obtaining a measurement of a temperature of tissue contacting the one of the plurality of electrodes, wherein the thermocouple includes two leads disposed along an outer surface of the at least one electrode, wherein each of the two leads is attached to the at least one of the plurality of electrodes in a spaced relationship.

2. The device of claim 1, wherein the at least one of the plurality of electrodes includes a proximal portion covered with an insulating material, a distal portion covered with an insulating material, and a middle portion between the proximal and distal portions and not covered by an insulating material, and wherein the two leads are attached to the middle portion.

3. The device of claim 1, wherein the plurality of electrodes are bipolar electrodes.

4. The device of claim 1, wherein, when one of the two leads detaches from the at least one of the plurality of electrodes, the thermocouple stops measuring temperature.

5. The device of claim 1, wherein the expandable electrode assembly is a basket, and wherein the plurality of electrodes are spaced radially about a longitudinal axis of the device.

6. The device of claim 1, further including an actuating member extending from a proximal end of the device toward the distal end, wherein longitudinal movement of the actuating member is configured to reciprocally move the expandable electrode assembly between a collapsed configuration and an expanded configuration.

7. A device for delivering energy to tissue, the device comprising:
    a flexible elongate body having a proximal end and a distal end;
    an expandable electrode assembly disposed adjacent to the distal end of the flexible elongate body, the electrode assembly including at least one electrically-conductive electrode; and
    a thermocouple in communication with the at least one electrode so that the at least one electrode and the thermocouple form a thermocouple junction for obtaining a measurement of a temperature of tissue contacting the at least one electrode, wherein the thermocouple includes two leads disposed along an outer surface of the at least one electrode, wherein each of the two leads is attached to the at least one electrode in a spaced relationship.

8. The device of claim 7, wherein the at least one electrode includes a proximal portion covered with an insulating material, a distal portion covered with an insulating material, and a middle portion between the proximal and distal portions and not covered by an insulating material, and wherein the two leads are attached to the middle portion.

9. The device of claim 7, wherein the expandable electrode assembly is a basket, and wherein the basket includes a plurality of electrodes that are spaced radially about a longitudinal axis of the device.

10. The device of claim 7, further including an actuating member extending from a proximal end of the device toward the distal end, wherein longitudinal movement of the actuating member is configured to reciprocally move the expandable electrode assembly between a collapsed configuration and an expanded configuration.

11. The device of claim 7, further including a lumen in the flexible elongate body, and an energizing member disposed through the lumen, wherein the energizing member is configured to deliver current to the at least one electrode.

12. The device of claim 7, wherein the at least one electrode is a radiofrequency electrode.

13. The device of claim 7, wherein the at least one electrode is configured to deliver energy in a monopolar manner.

14. The device of claim 7, wherein the at least one electrode is one of a plurality of electrodes configured to deliver energy in a bipolar manner.

15. The device of claim 7, wherein the at least one electrode has a length that extends along a longitudinal axis of the device.

16. A device for delivering energy to tissue, the device comprising:
    a flexible elongate body having a proximal end and a distal end;
    an expandable electrode assembly disposed adjacent to the distal end of the flexible elongate body, the electrode assembly including at least one electrically-conductive electrode; and
    a thermocouple in communication with the at least one electrode so that the at least one electrode and the thermocouple form a thermocouple junction for obtaining a measurement of a temperature of tissue contacting the at least one electrode, wherein the thermocouple includes two leads disposed along an outer surface of the at least one electrode, each of the two leads is attached to the at least one electrode in a spaced relationship, and when one of the two leads detaches from the electrode, the thermocouple stops measuring temperature.

17. The device of claim 16, wherein the expandable electrode assembly is a basket, and wherein the basket includes a plurality of electrodes that are spaced radially about a longitudinal axis of the device.

18. The device of claim 16, further including an actuating member extending from a proximal end of the device toward the distal end, wherein longitudinal movement of the actuating member is configured to reciprocally move the expandable electrode assembly between a collapsed configuration and an expanded configuration.

\* \* \* \* \*